(12) United States Patent
Kuwabara et al.

(10) Patent No.: US 7,144,906 B2
(45) Date of Patent: Dec. 5, 2006

(54) HETEROCYCLIC COMPOUNDS

(75) Inventors: Kenji Kuwabara, Otsu (JP);
Tomiyoshi Aoki, Mori Yama (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 273 days.

(21) Appl. No.: 10/276,670

(22) PCT Filed: May 25, 2001

(86) PCT No.: PCT/JP01/04400

§ 371 (c)(1),
(2), (4) Date: Nov. 18, 2002

(87) PCT Pub. No.: WO01/90087

PCT Pub. Date: Nov. 29, 2001

(65) Prior Publication Data

US 2003/0166697 A1 Sep. 4, 2003

(30) Foreign Application Priority Data

May 26, 2000 (JP) ........................ 2000-156936

(51) Int. Cl.
*A61K 31/421* (2006.01)
*C07D 263/32* (2006.01)

(52) U.S. Cl. ................. 514/374; 548/235; 548/236
(58) Field of Classification Search ............... 514/374; 548/235, 236
See application file for complete search history.

(56) References Cited

FOREIGN PATENT DOCUMENTS

| EP | 0 220 573 | 5/1987 |
| --- | --- | --- |
| EP | 0 601 930 | 6/1994 |
| EP | 1 067 109 | 1/2001 |
| EP | 1 108 713 | 6/2001 |
| EP | 1 122 255 | 8/2001 |
| WO | WO 99/31056 | 6/1999 |
| WO | WO 99/231056 | 6/1999 |
| WO | WO 02/580048 | 6/2001 |
| WO | WO 02/50048 | 6/2002 |
| WO | WO 02/062774 | 8/2002 |

OTHER PUBLICATIONS

Gigg et al., Journal of the Chemical Society [Section] C: Organic (1968), (15), 1903–1911.*
Elhakmaoui et al., Bioorganic & Medicinal Chemistry Letters, 1994, vol. 4, No. 16, 1937–1940.
Self, S. R. et al., "Romazarit: A Potential Disease–Modifying Antirheumatic Drug", Journal of Medicinal Chemistry, vol. 34, No. 2, 1991.
Yokoyama, M. et al., "Synthesis and Antiviral Activity of 1, 2, 3–Triazole and 8–Azapurine Derivaties Bearing Acyclic Sugars", Heterocycles, vol. 31, No. 9, 1990.
Self, S. R. et al., "Romazarit: A Potential Disease–Modifying Antirheumatic Drug", Journal of Medicinal Chemisty, voly. 34, No. 2, 1991.
Yokoyama, M. et al., "Synthesis and Antiviral Activity of 1,2,3–Triaxole and 8—Azapurine Derivatives Bearing Acyclic Sugars", Heterocycles, vol. 31, N o. 9, 1990.

* cited by examiner

*Primary Examiner*—Fiona T. Powers
(74) *Attorney, Agent, or Firm*—Greenberg Traurig LLP

(57) ABSTRACT

The present invention provides a preventive or therapeutic agent for hyperlipidemia, comprising as an active ingredient a heterocyclic compound of the formula [1], or a pharmaceutically acceptable salt thereof:

$$R^1\text{-Het-D-E} \qquad [1]$$

wherein:

$R^1$ is optionally substituted aryl or aromatic heterocyclic group, Het is a divalent aromatic heterocyclic group, D is alkylene, alkenylene, alkynylene, or the like, and E is carboxy, or the like, and novel compounds among the heterocyclic compounds of the formula [1] above, which has blood triglyceride lowering effect, LDL-C lowering effect, and blood glucose lowering effect and blood insulin lowering effect, or HDL-C increasing effect or atherogenic index lowering effect all together, and hence is useful in the prevention or treatment of hyperlipidemia, arteriosclerosis, diabetes mellitus, hypertension, obesity, and the like.

24 Claims, No Drawings

HETEROCYCLIC COMPOUNDS

This application is a 371 of PCT/JP01/04400 filed May 25, 2001.

TECHNICAL FIELD

The present invention is related to novel heterocyclic compounds and pharmaceutically acceptable salts thereof.

The compounds of the present invention have blood triglyceride lowering effect, low-density lipoprotein cholesterol (hereinafter, referred to as "LDL-C") lowering effect, and also blood glucose lowering effect, blood insulin lowering effect, or high-density lipoprotein cholesterol (hereinafter, referred to as "HDL-C") increasing effect, atherogenic index lowering effect, which index is the ratio of non-HDL-C to HDL-C calculated according to the formula: (total cholesterol—HDL-C)/(HDL-C). Accordingly, the compounds of the present invention are useful in the prevention and treatment of coronary artery disease, cerebral infarction, hyperlipidemia, arteriosclerosis or diabetes mellitus.

BACKGROUND ART

The insulin resistant syndrome complicated by disorder of carbohydrate and/or lipid metabolism and hypertension attracts attention as a multi-risk group of high incidence of ischemic heart disease. The insulin resistant syndrome is found in most of patients suffering from obesity and non insulin-dependent diabetes mellitus (NIDDM). The metabolic disorder of lipids herein recognized is the increase in blood triglycerides mainly due to the increase in chylomicron, very low density lipoproteins, and remnant lipoproteins which are the intermediary metabolites thereof, and the decrease in HDL-C (Diabetes, 37, 1595–1607 (1988); Arch. Intern. Med., 149, 1514–1520(1989); Diabetes Care, 14, 173–194 (1991)).

Although it has often been disserted that the blood triglyceride level is probably an important risk factor of arteriosclerotic diseases, the clear relevance has not been established. Said level, however, has been reported to be an independent risk factor of ischemic heart disease based on the results obtained recently using arteriography (Circulation, 90, 2230–2235 (1994)).

It is well known that the HDL-C level negatively correlates to incidence of ischemic heart diseases from the results of a lot of epidemiological researches (Circulation, 79, 8–15(1989)). HDL is thought to participate in the reverse cholesterol transport into liver from extrahepatic tissues and demonstrated to have anti-arteriosclerosis effect in animal model experiments (J. Clin. Invest., 85, 1234–1241(1990); Nature, 353, 265–267(1991)).

It has been confirmed that blood total cholesterol level, especially LDL-C level, positively correlates to incidence of ischemic heart diseases and the said incidence can be decreased by lowering the level in a large-scale intervention trial (Lipid Research Clinics Program: JAMA, 251, 351 (1984); Lipid Research Clinics Program: JAMA, 251, 365 (1984)).

Accordingly, compounds that decrease the blood triglyceride level and LDL-C level, and also increase the HDL-C level or decrease the atherogenic index are useful as a remedy for arteriosclerosis, especially for prevention or treatment of ischemic heart diseases. Further, compounds that improve the insulin resistance are expected to reduce the blood glucose level and blood insulin level, and improve the pathological conditions of complications such as diabetes mellitus, hyperinsulinemia, hypertension and obesity, which can be risk factors of arteriosclerotic diseases, and whereby exert effective preventive or therapeutic activity on arteriosclerosis.

It has been heretofore known that 2-aryl-5-alkyloxazole derivatives or 2-aryl-5-alkylthiazole derivatives of the general formula (A), which have some similarity to the compounds of the present invention have blood lipid lowering effect or blood glucose lowering effect.

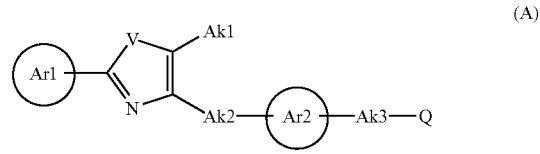

(A)

wherein:
Ring Ar1 is aryl; V is oxygen or sulfur; Ak1 is hydrogen, alkyl or haloalkyl; Ak2 is alkylene; Ak3 is alkylene, alkenylene or alkynylene optionally substituted by alkoxy, alkoxycarbonyl, acylthio, acylamino or aryl; Q is carboxy, 2,4-oxazolinedione-5-yl, 2,4-thiazolinedione-5-yl, or 1,2,4-oxadiazolidine-3,5-dione-2-yl; Ring Ar2 is a group of the formula [B1] or [B2].

(B1)

(B2)

For example, compounds included in the general formula (A), namely 2,4-thiazolidinedione derivatives, are reported to have blood lipid lowering effect or blood glucose lowering effect in U.S. Pat. No. 5,532,256, WO96/05186, JP H7-188227, A, JP S61-85372, A and U.S. Pat. No. 5,401, 761.

It is described that compounds included in the general formula (A), namely 2,4-oxazolidinedione derivatives, have blood lipid lowering effect or blood glucose lowering effect in JP H9-124623, A, WO95/18125, JP H7-165735, A and U.S. Pat. No. 5,468,762 and JP H8-92228, A.

It is described that compounds included in the general formula (A), namely 1,2,4-oxadiazolidine-3,5-dione derivatives, have blood lipid lowering effect or blood glucose lowering effect in U.S. Pat. No. 5,510,360 and U.S. Pat. No. 5,480,896.

It is described that compounds included in the general formula (A), namely carboxylic acid derivatives, have blood lipid lowering effect or blood glucose lowering effect in WO99/462325, WO98/00137, WO97/31907, WO96/38415, JP H9-323982, A, JP H8-325264, A, JP H5-507920, A, U.S. Pat. No. 5,510,360 and U.S. Pat. No. 5,480,896.

The compound of the general formula (A) is characterized in that it has:
(1) 2-aryl-5-alkyloxazole ring or 2-aryl-5-alkylthiazole ring at one end;
(2) carboxy, 2,4-oxazolinedione-5-yl, 2,4-thiazolinedione-5-yl or 1,2,4-oxadiazolidine-3,5-dione-2-yl at the other end; and
(3) an aromatic ring such as benzene represented by ring Ar2 in the molecule.

Further, EP-A-220573 describes that oxazole derivatives of the general formula (B) show antiarthritic activity.

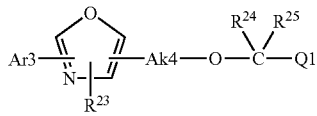

(B)

wherein:
Ar3 is substituted phenyl or thienyl; $R^{23}$ is hydrogen or alkyl; Ak4 is alkylene having 1 to 2 carbon atoms: $R^{24}$ and $R^{25}$ are each alkyl; Q1 is carboxy, alkoxycarbonyl, carbamoyl, N-alkylcarbamoyl or N,N-dialkylcarbamoyl.

DISCLOSURE OF INVENTION

One of objectives of the present invention is to provide an excellent preventive or therapeutic agent for hyperlipidemia, arteriosclerosis, diabetes mellitus, hypertension, obesity and the like, which has blood triglyceride lowering effect, LDL-C lowering effect and also blood glucose lowering effect, blood insulin lowering effect, or HDL-C increasing effect, atherogenic index lowering effect.

The present inventors have intensively studied to accomplish the objective above, and found that heterocyclic compounds of the formula [1] below met the objective and achieved the present invention.

Thus, the present invention provides a heterocyclic compound of the formula [1] below or pharmaceutically acceptable salts thereof, and a pharmaceutical composition comprising the same as an active ingredient.

$R^1$Het-D-E  [1]

wherein:
$R^1$ is aryl, aromatic heterocyclic group or cycloalkyl, said aryl or aromatic heterocyclic group being optionally substituted by the same or different one to three groups selected from alkyl, haloalkyl, trihaloalkyl, alkoxy, halogen and nitro;
Het is a divalent aromatic heterocyclic group; said aromatic heterocyclic group being optionally substituted by alkyl or trihaloalkyl;
D is alkylene, alkenylene, alkynylene or a group of the formula [2]:

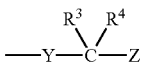

(2)

wherein W is CH or nitrogen, m is an integer of 1–10 and n is an integer of 0–9, with the proviso that m+n is an integer of 1–10; and
E is a group of the formula [3] or [4]:

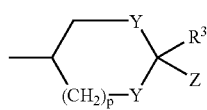

(3)

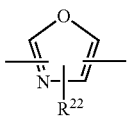

(4)

wherein Y is oxygen or sulfur; $R^3$ and $R^4$ are the same or different and each being hydrogen or alkyl; p is an integer of 0–2; Z is carboxy, alkoxycarbonyl, hydroxymethyl, carbamoyl, N-hydroxycarbamoyl, N-alkylcarbamoyl, N,N-dialkylcarbamoyl, cyano, 1H-5-tetrazolyl, 1-alkyl-5-tetrazolyl, or 2-alkyl-5-tetrazolyl, with the proviso that when D is a group of the formula [2], E is not a group of the formula [4].

Among heterocyclic compounds of the formula [1], those wherein Het is a group of the formula [5z]:

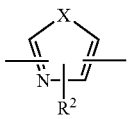

(5z)

wherein $R^{22}$ is hydrogen, alkyl or trihaloalkyl, D is alkylene having 1 to 2 carbon atoms, E is a group of the formula [4], and Y is oxygen include known compounds. However, the present inventors have, for the first time, found that compounds of the formula [1] have blood triglyceride lowering effect, LDL-C lowering effect, and also blood glucose lowering effect, blood insulin lowering effect, or HDL-C increasing effect, atherogenic index lowering effect.

Heterocyclic compounds [1] other than those of the formula [1] wherein Het is a group of the formula [5z], D is alkylene having 1 to 2 carbon atoms, $R^{22}$ is hydrogen, alkyl or trihaloalkyl, E is a group of the formula [4] and Y is oxygen, are novel compounds that have not been disclosed in any documents so far.

Among compounds [1] of the present invention, those wherein D is alkylene, alkenylene or alkynylene having 3–10 carbon atoms are preferred. Another preferred compounds are those wherein Het is a divalent aromatic heterocyclic group of the formula [5]:

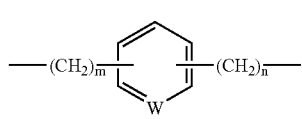

(5)

wherein X is oxygen, sulfur or $NR^6$, $R^6$ is hydrogen or alkyl, $R^2$ is hydrogen, alkyl or trihaloalkyl.

More preferred compounds among compounds [1] of the present invention are those wherein Het is a divalent aromatic heterocyclic group of the formula [5], X is oxygen, sulfur or $NR^6$, $R^6$ is hydrogen or alkyl, $R^2$ is hydrogen, alkyl or trihaloalkyl, and D is alkylene, alkenylene or alkynylene having 3–10 carbon atoms.

Still more preferred compounds among compounds [1] of the present invention are those wherein $R^1$ is phenyl optionally substituted by one to two groups selected from alkyl, halogen, trihaloalkyl and alkoxy; Het is a divalent aromatic heterocyclic group of the formula [5a]:

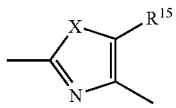

(5a)

wherein X is as defined above and $R^{15}$ is alkyl or trihaloalkyl; and D is alkylene or alkenylene having 3–7 carbon atoms.

Still furthermore preferred compounds among compounds [1] of the present invention are firstly those wherein $R^1$ is phenyl optionally substituted by one to two groups selected from alkyl, halogen, trihaloalkyl and alkoxy, Het is a divalent aromatic heterocyclic group of the formula [5a], X is oxygen, sulfur or $NR^6$, $R^6$ is hydrogen or alkyl, $R^{15}$ is alkyl or trihaloalkyl, D is alkylene or alkenylene having 3–5 carbon atoms, E is a group of the formula [3], p is 1, Y is oxygen, $R^3$ is hydrogen or alkyl and Z is carboxy or alkoxycarbonyl; and secondly those wherein $R^1$ is phenyl optionally substituted by one to two groups selected from alkyl, halogen and alkoxy, Het is a divalent aromatic heterocyclic group of the formula [5a], X is oxygen, sulfur or $NR^6$, $R^6$ is hydrogen or alkyl, $R^{15}$ is alkyl or trihaloalkyl, D is alkylene, alkenylene or alkynylene having 5–7 carbon atoms, E is a group of the formula [4], Y is oxygen, $R^3$ and $R^4$ are the same or different and each being hydrogen or alkyl and Z is carboxy or alkoxycarbonyl.

Especially preferred compounds among compounds [1] of the present invention are firstly those wherein $R^1$ is phenyl optionally substituted by one to two groups selected from alkyl and alkoxy, Het is a divalent aromatic heterocyclic group of the formula [5a], X is oxygen, $R^{15}$ is alkyl, D is alkylene having 3–5 carbon atoms, E is a group of the formula [3], p is 1, Y is oxygen, $R^3$ is alkyl and Z is carboxy; and secondly those wherein $R^1$ is phenyl optionally substituted by one to two groups selected from alkyl, halogen and alkoxy, Het is a divalent aromatic heterocyclic group of the formula [5a], X is oxygen, $R^{15}$ is alkyl, D is alkylene, alkenylene or alkynylene having 5–7 carbon atoms, E is a group of the formula [4], Y is oxygen, $R^3$ and $R^4$ are the same and each being alkyl and Z is carboxy.

Specific examples of preferred compounds [1] of the present invention include the following heterocyclic compounds (1)–(14) or pharmaceutically acceptable salts thereof.

(1) 2-Methyl-2-[6-(5-methyl-2-phenyloxazol-4-yl)-(E)-4-hexenyloxy]propionic acid
(2) c-5-[4-(5-Methyl-2-phenyloxazol-4-yl)butyl]-1,3-dioxane-r-2-carboxylic acid
(3) 2-Methyl-2-[6-(5-methyl-2-phenyloxazol-4-yl)-4-hexynyloxy]propionic acid
(4) 2-Isobutyl-c-5-[4-(5-methyl-2-phenyloxazol-4-yl)butyl]-1,3-dioxane-r-2-carboxylic acid
(5) 2-Ethyl-c-5-[4-(5-methyl-2-phenyloxazol-4-yl)butyl]-1,3-dioxane-r-2-carboxylic acid
(6) 2-Methyl-c-5-{4-[5-methyl-2-(4-trifluoromethylphenyl)oxazol-4-yl]butyl}-1,3-dioxane-r-2-carboxylic acid
(7) 2-Methyl-c-5-[4-(5-methyl-2-phenyloxazol-4-yl)-(E)-3-butenyl]-1,3-dioxane-r-2-carboxylic acid
(8) c-5-{4-[2-(4-tert-Butylphenyl)-5-methyloxazol-4-yl]butyl}-2-methyl-1,3-dioxane-r-2-carboxylic acid
(9) 2-Methyl-2-[6-(5-methyl-2-phenyloxazol-4-yl)hexyloxy]propanol
(10) 2-Methyl-2-{6-[5-methyl-2-(p-tolyl)oxazol-4-yl]hexyloxy}propionic acid
(11) 2-Methyl-c-5-{4-[5-methyl-2-(p-tolyl)oxazol-4-yl]butyl}-1,3-dioxane-r-2-carboxylic acid
(12) 2-Methyl-c-5-{4-[5-methyl-2-(3-fluoro-4-methylphenyl)oxazol-4-yl]butyl}-1,3-dioxane-r-2-carboxylic acid
(13) 2-Methyl-c-5-{4-[5-methyl-2-(m-tolyl)oxazol-4-yl]butyl}-1,3-dioxane-r-2-carboxylic acid
(14) 2-Methyl-c-5-{4-[5-methyl-2-(3,4-dimethylphenyl)oxazol-4-yl]butyl}-1,3-dioxane-r-2-carboxylic acid For purposes of the present invention, the term "alkyl" used herein means a straight- or branched-chain alkyl group having 1 to 7 carbon atoms, for example, methyl, ethyl, n-propyl, isopropyl, n-butyl, isobutyl, sec-butyl, tert-butyl, n-pentyl, isopentyl, n-hexyl, isohexyl, n-heptyl and isoheptyl. Straight-chain alkyl groups having 1 to 3 carbon atoms are preferred, for example, methyl, ethyl and n-propyl.

Examples of alkyl moiety of the groups "haloalkyl", "trihaloalkyl", "alkoxy", "alkoxycarbonyl", "N-alkylcarbamoyl", "N,N-dialkylcarbamoyl", "1-alkyl-5-tetrazolyl" and "2-alkyl-5-tetrazolyl" include alkyl groups as defined above.

The term "cycloalkyl" means a cycloalkyl group having 4 to 8 carbon atoms, for example, cyclobutyl, cyclopentyl, cyclohexyl, cycloheptyl and cyclooctyl. Cycloalkyl groups having 5 to 7 carbon atoms are preferred.

The term "alkylene" means a straight- or branched-chain alkylene group having 1 to 10 carbon atoms, for example, methylene, ethylene, 1-methylethylene, 2-methylethylene, trimethylene, tetramethylene, pentamethylene, hexamethylene, heptamethylene, octamethylene, nonamethylene and decamethylene. Alkylene groups having 3 to 10 carbon atoms are preferred and those having 3 to 7 carbon atoms are more preferred.

The term "alkenylene" means a straight- or branched-chain alkenylene group having 2 to 10 carbon atoms, for example, ethenylene, 1-propenylene, 2-propenylene, 1-butenylene, 2-butenylene, 3-butenylene, 1-pentenylene, 2-pentenylene, 3-pentenylene, 4-pentenylene, 4-methyl-3-pentenylene, 1-hexenylene, 2-hexenylene, 3-hexenylene, 4-hexenylene, 5-hexenylene, 1-heptenylene, 2-heptenylene, 3-heptenylene, 4-heptenylene, 5-heptenylene, 6-heptenylene, 1-octenylene, 2-octenylene, 3-octenylene, 4-octenylene, 5-octenylene, 6-octenylene, 7-octenylene, 1-nonenylene, 2-nonenylene, 3-nonenylene, 4-nonenylene, 5-nonenylene, 6-nonenylene, 7-nonenylene, 8-nonenylene, 1-decenylene, 2-decenylene, 3-decenylene, 4-decenylene, 5-decenylene, 6-decenylene, 7-decenylene, 8-decenylene and 9-decenylene. Alkenylene groups having 3 to 10 carbon atoms are preferred and those having 3 to 7 carbon atoms are more preferred.

The term "alkynylene" means a straight- or branched-chain alkynylene group having 2 to 10 carbon atoms, for example, ethynylene, 1-propynylene, 2-propynylene, 1-butynylene, 2-butynylene, 3-butynylene, 1-pentynylene, 2-pentynylene, 3-pentynylene, 4-pentynylene, 2-methyl-3-pentynylene, 1-hexynylene, 2-hexynylene, 3-hexynylene, 4-hexynylene, 5-hexynylene, 1-heptynylene, 2-heptynylene, 3-heptynylene, 4-heptynylene, 5-heptynylene, 6-heptynylene, 1-octynylene, 2-octynylene, 3-octynylene, 4-octynylene, 5-octynylene, 6-octynylene, 7-octynylene, 1-nonynylene, 2-nonynylene, 3-nonynylene, 4-nonynylene, 5-nonynylene, 6-nonynylene, 7-nonynylene, 8-nonynylene, 1-decynylene, 2-decynylene, 3-decynylene, 4-decynylene, 5-decynylene, 6-decynylene, 7-decynylene, 8-decynylene and 9-decynylene. Alkynylene groups having 3 to 10 carbon atoms are preferred and those having 3 to 7 carbon atoms are more preferred.

The term "aryl" means an aryl group having 6 to 10 carbon atoms, for example, phenyl, 1-naphthyl and 2-naphthyl, and phenyl is preferred.

The term "aromatic heterocyclic ring" means a 5–6 membered aromatic ring containing 1 to 4 hetero atoms selected from nitrogen, oxygen and sulfur, or a condensed ring thereof with a benzene ring. Examples include 1-pyrrolyl, 2-pyrrolyl, 3-pyrrolyl, 3-indolyl, 2-furyl, 3-furyl, 3-benzofuranyl, 2-thienyl, 3-thienyl, 3-benzothienyl, 2-oxazolyl, 2-thiazolyl, 2-benzothiazolyl, 2-imidazolyl, 4-imidazolyl, 2-benzimidazolyl, 1H-1,2,4-triazol-1-yl, 1H-tetrazol-5-yl, 2-pyridyl, 3-pyridyl, 4-pyridyl, pyridine-1-oxide-2-yl, pyridine-1-oxide-3-yl, pyridine-1-oxide-4-yl, 2-pyrimidinyl, 4-pyrimidinyl, 2-pyrazinyl, 1,3,5-triazine-2-yl.

The term "divalent aromatic heterocyclic ring" means a 5–6 membered aromatic ring containing 1 to 4 hetero atoms selected from nitrogen, oxygen and sulfur, or a condensed ring thereof with a benzene ring. Examples include pyrrolylene, indolylene, furanylene, benzofuranylene, thienylene, benzothienylene, oxazolylene, thiazolylene, benzothiazolylene, imidazolylene, benzimidazolylene, 1H-1,2,4-triazolylene, pyridinylene, pyrimidinylene, pyrazinylene and 1,3,5-triazinylene.

Examples of "halogen" include fluorine, chlorine, bromine and iodine.

Examples of halogen moiety of "haloalkyl" and "trihaloalkyl" include the halogen as defined above.

Specific examples of "trihaloalkyl" include trifluoromethyl, trichloromethyl, 2, 2, 2-trifluoroethyl and 2, 2, 2-trichloroethyl.

The compounds [1] of the present invention can be prepared by the processes illustrated below or in the working Examples.

Process A

A compound [1a] of the present invention wherein E is a group of the formula [3] and Z is alkoxycarbonyl can be prepared by reacting a compound [11] and a compound [22].

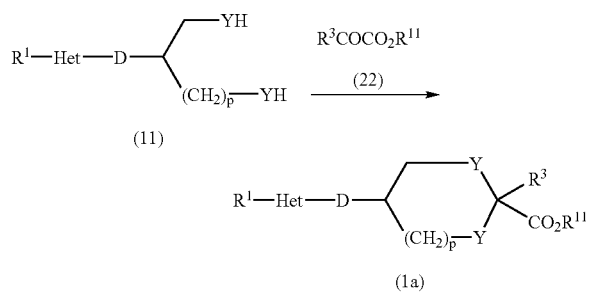

wherein $R^1$, Het, D, Y, p and $R^3$ have the same meaning as defined above, and $R^{11}$ is alkyl.

Generally, the reaction can be conducted in an appropriate solvent (e.g., a polar solvent such as acetonitrile or N,N-dimethylformamide (DMF), ether solvent such as tetrahydrofuran (THF) or diethyl ether, halogenated hydrocarbon solvent such as chloroform or dichloromethane, ester solvent such as methyl acetate or ethyl acetate, hydrocarbon solvent such as benzene, toluene or n-hexane, or a mixture thereof), in the presence of a Lewis acid (e.g., boron trifluoride etherate complex) at –20 to 150° C. Although the reaction time varies depending on the kind of the compound [11] and compound [22], or reaction temperature, it would be suited to be between 30 minutes and 24 hours in general.

The compound [22] is preferably used in an amount of 1 to 5 moles to one mole of the compound [11].

Process B

A compound [1b] of the present invention wherein E is a group of the formula [4] and Z is carboxy can be prepared by reacting a compound [12] and a compound [13], and then treating with acid.

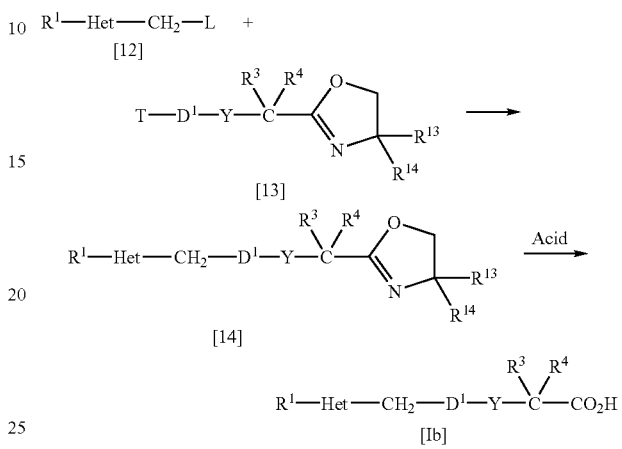

wherein $R^1$, Het, Y, $R^3$ and $R^4$ have the same meaning as defined above, L is a leaving group such as halogen, methanesulfonyloxy or toluenesulfonyloxy, T is halogen, $R^{13}$ and $R^{14}$ are the same or different and each being alkyl, $D^1$ is alkylene, alkenylene or alkynylene having fewer carbon atoms than that for D by one atom (D has the same meaning as defined above).

The compound [14] can be prepared by, in general, treating a compound [13] with a metal reagent such as butyl lithium or magnesium followed by reacting with a compound [12] in the presence of copper iodide or copper bromide at –80 to 150° C., in an aprotic solvent (e.g., a polar solvent such as acetonitrile or N,N-dimethylformamide (DMF), ether solvent such as tetrahydrofuran (THF) or diethyl ether, halogenated hydrocarbon solvent such as chloroform or dichloromethane, ester solvent such as methyl acetate or ethyl acetate, hydrocarbon solvent such as benzene, toluene or n-hexane, or a mixture thereof). Although the reaction time varies depending on the kind of the compound [12], compound [13] and metal reagent, or reaction temperature, it would be suited to be between 30 minutes and 24 hours in general. The metal reagent and the compound [12] is preferably used in an amount of 1 to 1.2 moles to one mole of the compound [13].

The compound [1b] can be, in general, prepared by treating a compound [14] with an acid (e.g., hydrochloric acid) in an alcohol solvent (e.g., methanol or ethanol) at –80 to 80° C. for 5 minutes to 24 hours.

Process C

A compound [1c] wherein D is alkenylene which adjoins Het at the unsaturated bond moiety can be prepared by Wittig reaction using a compound [15] and compound [16].

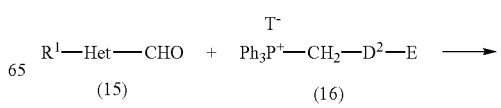

-continued

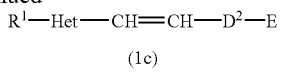

(1c)

wherein R¹, Het, E and T have the same meaning as defined above, Ph is phenyl, D² is alkenylene having fewer carbon atoms than that for D by two atoms (D has the same meaning as defined above), or a group of the formula [2] above.

The reaction can be conducted, in general, in a solvent similar to that used in PROCESS A above in the presence of a base (e.g., sodium hydroxide) at −20 to 150° C. Although the reaction time varies depending on the kind of the compound [15] and compound [16], or reaction temperature, it would be suited to be between 30 minutes and 24 hours in general. The compound [16] is preferably used in an amount of 1 to 1.2 moles to one mole of the compound [15].

Process D

A compound [1d] of the present invention wherein Het is a group of the formula [5a]:

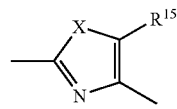

[5a]

wherein X and R¹⁵ have the same meaning as defined above, E is a group of the formula [3] or [4], and Z is alkoxycarbonyl can also be prepared by reacting a compound [17] with phosphorus oxychloride, thionyl chloride, phosphorus pentoxide, a Davy reagent methyl (2,4-bis(methylthio)-1,3-dithia-2,4-diphosphetane-2,4-disulfide), a Lawesson's reagent (2,4-bis(4-methoxyphenyl)-1,3-dithia-2,4-diphosphethane-2,4-disulfide), ammonia or alkylamine. When phosphorus oxychloride, thionyl chloride or phosphorus pentoxide is used, oxazole derivatives can be obtained, when a Davy reagent methyl or a Lawesson's reagent is used, thiazole derivatives can be obtained, and when ammonia or alkylamine is used, imidazole derivatives can be obtained.

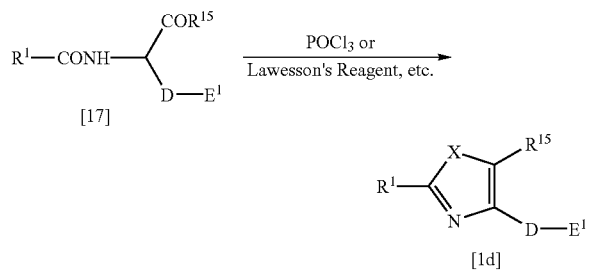

wherein R¹, D and R¹⁵ have the same meaning as defined above, and E¹ is a group of the formula [31] or [41]:

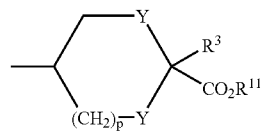

[31]

-continued

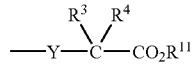

[41]

wherein R³, R⁴, R¹¹, Y and p have the same meaning as defined above.

Generally, the reaction can be conducted in an appropriate solvent (e.g., a hydrocarbon solvent such as benzene, toluene or xylene, a halogenated hydrocarbon solvent such as chloroform or dichloromethane, a polar solvent such as N,N-dimethylformamide (DMF), ether solvent such as tetrahydrofuran (THF) or diethyl ether, or acetic acid, or a mixture thereof) at −10 to 200° C. Although the reaction time varies depending on the kind of the reagent (e.g., phosphorus oxychloride, Lawesson's reagent, alkylamine), the kind of compound [17], or reaction temperature, it would be suited to be between 30 minutes and 24 hours in general. The phosphorus oxychloride, thionyl chloride, phosphorus pentoxide, Davy reagent methyl, Lawesson's reagent, ammonia or alkylamine is preferably used in an amount of 1 to 10 moles to one mole of the compound [17].

Process E

A compound [1e] of the present invention wherein Het is a group of the formula [5a] above, E is a group of the formula [4] and Z is alkoxycarbonyl can also be prepared by reacting a compound [18] and a compound [19].

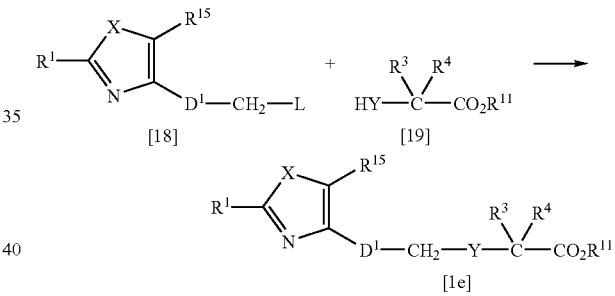

wherein R¹, R³, R⁴, R¹¹, R¹⁵, X, Y, L and D¹ have the same meaning as defined above.

The reaction can be conducted, in general, in a solvent similar to that used in PROCESS A above in the presence of a base (e.g., sodium hydride or sodium carbonate) at −20 to 150° C. Although the reaction time varies depending on the kind of the compound [18] and compound [19], or reaction temperature, it would be suited to be between 30 minutes and 24 hours in general. The compound [19] is preferably used in an amount of 1 to 1.2 moles to one mole of the compound [18].

Process F

A compound [1d] of the present invention wherein Het is a group of the formula [5a] above can also be prepared by reacting a compound [20] and a compound [21].

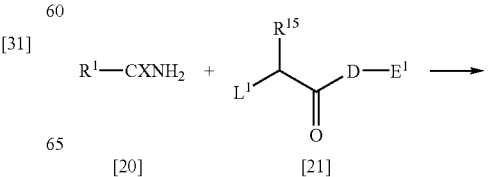

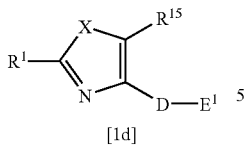

wherein $R^1$, $R^{15}$, D, $E^1$ and X have the same meaning as defined above, and $L^1$ is chlorine or bromine.

The reaction can be conducted, in general, in the absence of a solvent or in a solvent similar to that used in PROCESS A above in the presence of a base (e.g., sodium hydride or sodium carbonate) at −20 to 150° C. Although the reaction time varies depending on the kind of the compound [20] and compound [21], or reaction temperature, it would be suited to be between 30 minutes and 24 hours in general. The compound [21] is preferably used in an amount of 1 to 1.2 moles to one mole of the compound [20].

Process G

A compound [1h] of the present invention wherein Z is carboxy can be prepared by hydrolyzing a compound [1g] of the present invention wherein Z is alkoxycarbonyl.

A compound [1g] of the present invention can be prepared by allowing a compound [1h] of the present invention to condense with an alcohol [73] or to react with an alkylating agent.

Further, a compound [1i] of the present invention wherein Z is carbamoyl, N-hydroxycarbamoyl, N-alkylcarbamoyl or N,N-dialkylcarbamoyl can be prepared by reacting a compound [1h] of the present invention with a compound [82], i.e., ammonia, hydroxylamine, alkylamine or dialkylamine.

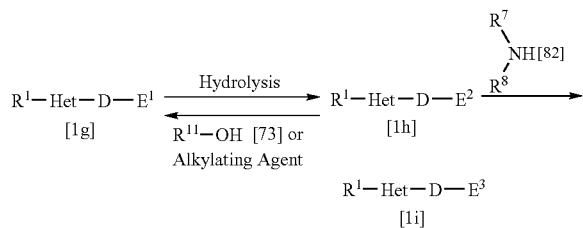

wherein $R^1$, $R^{11}$, Het, D and $E^1$ have the same meaning as defined above; $R^7$ is hydrogen and $R^8$ is hydrogen, hydroxy or alkyl, or $R^7$ is alkyl and $R^8$ is alkyl; $E^2$ is a group of the formula [32] or [42]; $E^3$ is a group of the formula [33] or [43]:

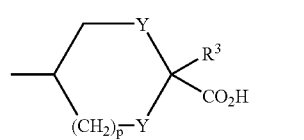

[32]

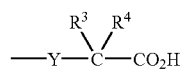

[33]

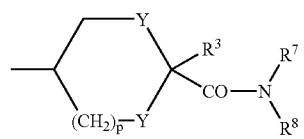

[42]

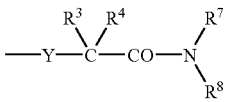

[43]

wherein $R^3$, $R^4$, $R^7$, $R^8$, Y and p have the same meaning as defined above.

The hydrolysis of compound [1g] can generally be conducted in a mixed solvent of an alcohol solvent such as methanol, ethanol, isopropanol or tert-butyl alcohol and water in the presence of an acid (e.g., hydrochloric acid, sulfuric acid or p-toluenesulfonic acid) or a base (e.g., sodium hydroxide or potassium hydroxide) at −20 to 150° C. Although the reaction time varies depending on the kind of compound [1g], or reaction temperature, it would be suited to be between 30 minutes and 24 hours in general. The acid or base is preferably used in an amount of 1 to 20 moles to one mole of the compound [1g].

The condensation between a compound [1h] and an alcohol [73] can be, in general, conducted using the alcohol as a solvent in the presence of an acid (e.g., hydrochloric acid, sulfuric acid or p-toluenesulfonic acid) at −20 to 150° C. Although the reaction time varies depending on the kind of compound [1h], kind of alcohol, or reaction temperature, it would be suited to be between 30 minutes and 24 hours in general. The acid is preferably used in an amount of 0.1 to 1.2 moles to 1 mole of compound [1h].

The said condensation reaction can also be conducted in a solvent similar to that used in PROCESS A above in the presence of a condensing agent (e.g., N,N'-dicyclohexylcarbodiimideor 1,1'-carbonyldiimidazole) at −20 to 150° C. Although the reaction time varies depending on the kind of compound [1h], kind of alcohol or condensing agent, or reaction temperature, it would be suited to be between 30 minutes and 24 hours in general. The condensing agent is preferably used in an amount of 1 to 1.2 moles to 1 mole of compound [1h].

The reaction between a compound [1h] and an alkylating agent (e.g., trimethylsilyldiazomethane/methanol, methyl iodide) can be conducted in a solvent similar to that used in PROCESS A above at −20 to 150° C. Although the reaction time varies depending on the kind of compound [1h], kind of alkylating agent, or reaction temperature, it would be suited to be between 30 minutes and 24 hours in general. The alkylating agent is preferably used in an amount of 1 to 2 moles to 1 mole of compound [1h].

The reaction between a compound [1h] and a compound [82] can be conducted in a manner similar to the said condensing reaction between a compound [1h] and an alcohol [73]. Further, a compound [1i] of the present invention can be prepared by reacting a reactive derivative of compound [1h] and a compound [82] by a method known in the art. Examples of reactive derivatives include reagents generally used in amidation such as acid halides (acid chloride or acid bromide), mixed acid anhydride, activated amide, and the like.

For example, when acid halide is used as a reactive derivative, the reaction can be conducted in an aprotic solvent (e.g., a polar solvent such as acetonitrile or N,N-dimethylformamide (DMF), ether solvent such as tetrahydrofuran (THF) or diethyl ether, halogenated hydrocarbon solvent such as chloroform or dichloromethane, hydrocarbon solvent such as benzene, toluene or n-hexane, or a mixture thereof) in the presence of a base (e.g., potassium carbonate, sodium carbonate, sodium hydrogen carbonate, potassium hydrogen carbonate, pyridine, 4-dimethylaminopyridine, triethylamine, sodium hydroxide) at −20 to 100° C. Although the reaction time varies depending on the kind of acid halide and compound [82], or reaction temperature, it would be suited to be between 30 minutes and 24 hours in general. The compound [82] is preferably used in an amount of 1 to 1.2 moles to one mole of the acid halide.

Process H

A compound [1k] of the present invention wherein D is alkenylene which adjoins Het at the unsaturated bond moiety can also be prepared by dehydrogenating a compound [1j] of the present invention wherein D is alkylene.

Further, a compound [1k] of the present invention can also be prepared by hydrogenating a compound [1 m] of the present invention wherein D is alkynylene which adjoins Het at the unsaturated bond moiety.

A compound [1j] of the present invention can also be prepared by hydrogenating a compound [1k] of the present invention.

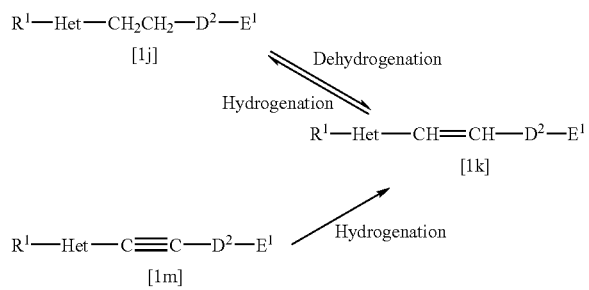

wherein $R^1$, Het, $D^2$ and $E^1$ have the same meaning as defined above.

The dehydrogenation of a compound [1j] can be conducted by reacting the compound with N-bromosuccinimide (NBS) or N-chlorosuccinimide (NCS) in a solvent similar to that used in PROCESS A above at −20 to 150° C., and then reacting with a base (e.g., sodium hydroxide or potassium hydroxide) in alcohol solvent such as methanol or ethanol. Although the reaction time varies depending on the kind of compound [1j], or reaction temperature, it would be suited to be between 30 minutes and 24 hours in general. The NBS NCS, or a base is preferably used in an amount of 1 to 1.2 moles to 1 mole of compound [1j].

The hydrogenation of a compound [1 m] can be conducted in an alcohol solvent (e.g., methanol or ethanol) in the presence of palladium catalyst (e.g., palladium-calcium carbonateor palladium-carbon) at −20 to 150° C. Although the reaction time varies depending on the kind of compound [1 m], palladium catalyst, or reaction temperature, it would be suited to be between 30 minutes and 24 hours in general. The palladium catalyst is preferably used in an amount of 0.05 to 0.5 moles to 1 mole of compound [1 m].

The hydrogenation of a compound [1k] can be conducted in an alcohol solvent (e.g., methanol or ethanol) in the presence of palladium catalyst (e.g., palladium-carbon) at −20 to 150° C. Although the reaction time varies depending on the kind of compound [1k], palladium catalyst, or reaction temperature, it would be suited to be between 30 minutes and 24 hours in general. The palladium catalyst is preferably used in an amount of 0.05 to 0.2 moles to 1 mole of compound [1k].

Process I

A compound [1n] of the present invention wherein Z is hydroxymethyl can be prepared by reducing a compound [1g] of the present invention wherein Z is alkoxycarbonyl.

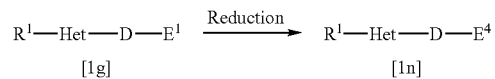

wherein $R^1$, Het, D, $E^1$ have the same meaning as defined above, $E^4$ is a group of the following formula [34] or [44]:

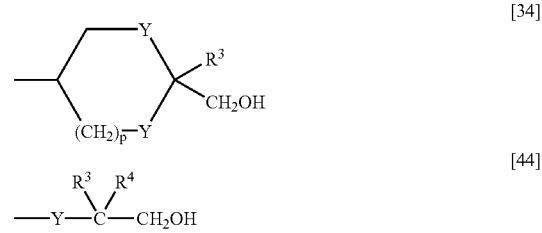

wherein $R^3$, $R^4$, Y and p have the same meaning as defined above.

The reaction can be conducted in the presence of a reducing agent (e.g., lithium aluminium hydride, sodium borohydrideor lithium diisobutylalminium hydride) in an appropriate solvent (e.g., ether solvent such as tetrahydrofuran (THF) or diethyl ether, a polar solvent such as N,N-dimethylformamide (DMF) or dimethyl sulfoxide, an alcohol solvent such as methanol, ethanol or isopropanol, or a mixture thereof) at −20 to 100° C. Although the reaction time varies depending on the kind of the compound [1g] or reaction temperature, it would be suited to be between 30 minutes and 24 hours in general. The reducing agent is preferably used in an amount of 0.5 to 2 moles to one mole of the compound [1g].

Process J

A compound [1q] wherein E is a group of the formula [3] or [4] and Z is cyano can be prepared from a compound [1p] of the present invention wherein Z is carbamoyl or N-hydroxycarbamoyl.

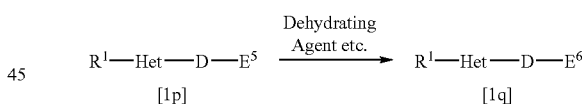

wherein $R^1$, Het and D have the same meaning as defined above, $E^5$ is a group of the formula [35] or [45], and $E^6$ is a formula of the group [36] or [46]:

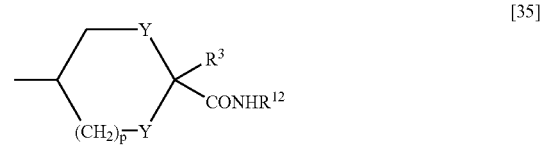

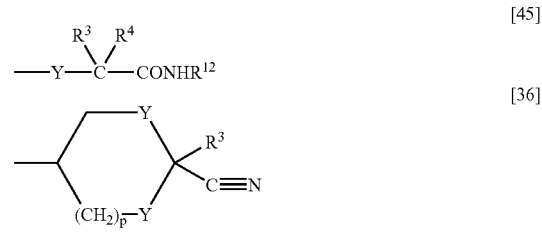

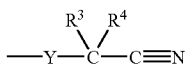

wherein $R^3$, $R^4$, Y and p have the same meaning as defined above, and $R^{12}$ is hydrogen or hydroxy.

When the starting compound wherein Z is carbamoyl, i.e., $R^{12}$ is hydrogen, is used, it can generally be treated with a dehydrating agent (e.g., phosphorus pentoxide, thionyl chloride, trifluoroacetic anhydride or N,N'-dicyclohexylcarbodiimide) without a solvent or in a solvent similar to that used in PROCESS A above. Although the reaction time varies depending on the kind of compound [1p], kind of dehydrating agent, or reaction temperature, it would be suited to be between 30 minutes and 24 hours in general. The dehydrating agent is preferably used in an amount of 1 to 5 moles to 1 mole of compound [1p].

When the starting compound wherein Z is N-hydroxycarbamoyl, i.e., $R^{12}$ is hydroxy, is used, the reaction can be conducted in accordance with the method of A. Liguori et al., Synthesis, 168(1987).

Process K

A compound [1r] of the present invention wherein E is a group of the formula [3] or [4] and Z is 1H-5-tetrazolyl can be prepared by reacting a compound [1q] of the present invention wherein Z is cyano with an azide.

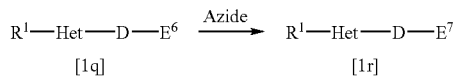

wherein $R^1$, Het, D and $E^6$ have the same meaning as defined above, and $E^7$ is a group of the formula [37] or [47]:

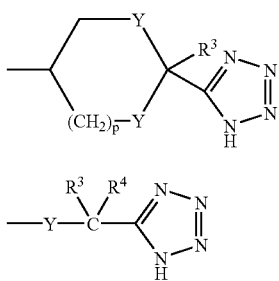

wherein $R^3$, $R^4$, Y and p have the same meaning as defined above.

The reaction can generally be conducted in an appropriate solvent (e.g., an alcohol solvent such as methanol, ethanol or methoxyethanol, hydrocarbon solvent such as benzene or toluene, halogenated hydrocarbon solvent such as chloroform or dichloromethane, polar solvent such as N,N-dimethylformamide (DMF) or dimethyl sulfoxide, ether solvent such as tetrahydrofuran (THF), or a mixture thereof) in the presence of an azide (e.g., sodium azide, azide trimethylsilane, or azide trimethyltin) at 0 to 200° C. The reaction can be conducted in the coexistence of an additive such as lithium chloride or ammonium chloride. Although the reaction time varies depending on the kind of the compound [1q], kind of the azide, or reaction temperature, it would be suited to be between 30 minutes and 100 hours in general.

Process L

A compound [1s] of the present invention wherein E is a group of the formula [3] or [4] and Z is 1-alkyl-5-tetrazolyl or 2-alkyl-5-tetrazolyl can be prepared by reacting a compound [1r] of the present invention wherein Z is 1H-5-tetrazolyl with an alkylating agent.

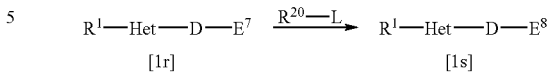

wherein $R^1$, Het, D, $E^7$ and L have the same meaning as defined above, $R^{20}$ is alkyl and $E^8$ is a group of the formula [38] or [48]:

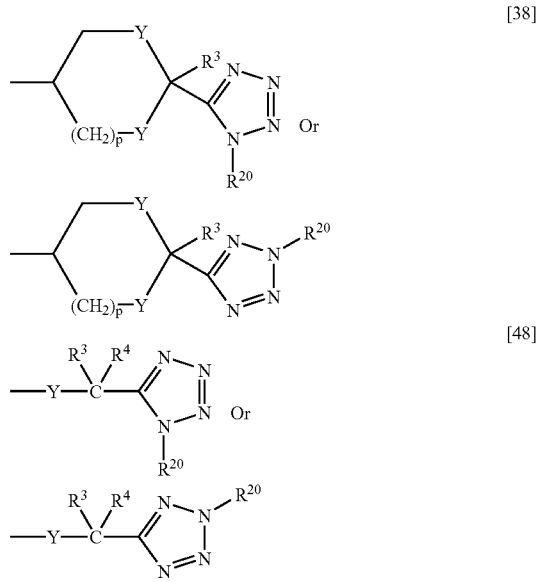

wherein $R^3$, $R^4$, Y, p and $R^{20}$ have the same meaning as defined above.

The reaction can be conducted, for example, in a solvent similar to that used in PROCESS A above in the presence of an alkylating agent (e.g., alkyl halide, alkyl mesylate or alkyl tosylate) and a base at 0 to 150° C. Examples of a base to be used includes an organic amine (e.g., pyridine or triethylamine), a metal hydride (e.g., sodium hydride), an inorganic base (e.g., potassium carbonate, sodium hydrogen carbonate or sodium hydroxide). Although the reaction time varies depending on the kind of the starting material, or reaction temperature, it would be suited to be between 30 minutes and 100 hours in general. The halogenating agent and the base are each used in an amount of 1 to 10 moles preferably 1 to 5 moles to one mole of the compound [1r].

The present compounds may exist as tautomers. The present invention encompasses respective tautomers within the scope of the invention.

The present compounds may exist as geometric isomers due to the presence of a double bond. The present invention encompasses respective geometric isomers and a mixture thereof.

The present compounds may exist as stereoisomers due to the presence of an asymmetric carbon atom. The present invention encompasses respective stereoisomers and a mixture thereof.

Such a stereoisomer can be obtained from a mixture by means of silica gel column chromatography.

Further, said stereoisomer can be obtained from a mixture by liquid chromatography using a column for separating an optically active substance (e.g., CHIRALCEL® OD, CHIRALCEL® OF, DAICEL, Ltd.).

When the compound of the present invention has a carboxy group, it can be converted into a pharmaceutically acceptable salt by a known method. Examples of the pharmaceutically acceptable salt include alkaline metal salt (e.g., sodium salt, potassium salt, etc.), alkaline earth metal salt (e.g., calcium salt, magnesium salt, etc.), ammonium salt, salt with an organic amine (e.g., triethyl amine, lysine, arginine, etc.), and the like.

For example, an alkaline metal salt of the present compound can be prepared by adding one equivalent of sodium hydroxide or potassium hydroxide to the present compound preferably in an alcoholic solvent.

An alkaline earth metal salt of the present compound can be prepared by dissolving the alkaline metal salt obtained according to the above-mentioned method into water, methanol, ethanol or a mixed solvent thereof and adding one equivalent of calcium chloride or the like.

When the present compound is basic, it can be converted into a pharmaceutically acceptable salt by a know method. Examples of salt includes a salt with an inorganic acid such as hydrochloric acid, sulfuric acid, nitric acid, phosphoric acid, or the like; or a salt with an organic acid such as fumaric acid, maleic acid, methanesulfonic acid, p-toluenesulfonic acid, or the like. For example, a hydrochloride of the present compound can be prepared by adding one equivalent of hydrochloric acid to the present compound, preferably in an alcohol solvent.

The present compound or a salt thereof can be isolated and purified from the reaction mixture of the reaction above by any of conventional methods; for example, extraction, concentration, neutralization, filtration, recrystallization, column chromatography, thin-layer chromatography, and the like.

The compounds used as the starting material in the preparation of the present compounds are known compounds, or can be, for example, prepared according to the processes illustrated below or those described in the Reference Examples.

Preparation of Compounds [11a] and [11b]

Among compounds of the formula [11] used as the starting material in the PROCESS A, those wherein D is $CH_2$-$D^1$ and Y is oxygen (compound [11a]) or sulfur (compound [11b]) can be prepared according to the following processes.

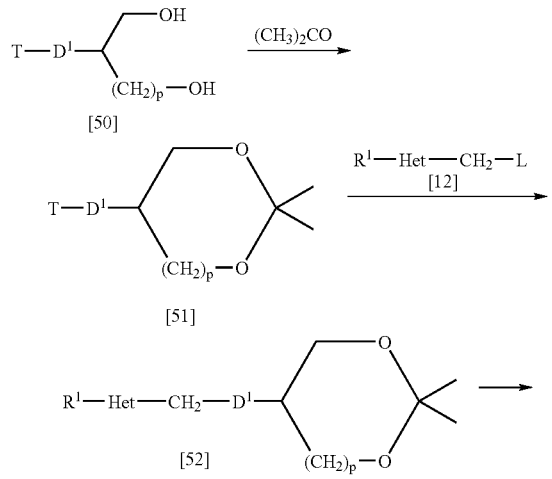

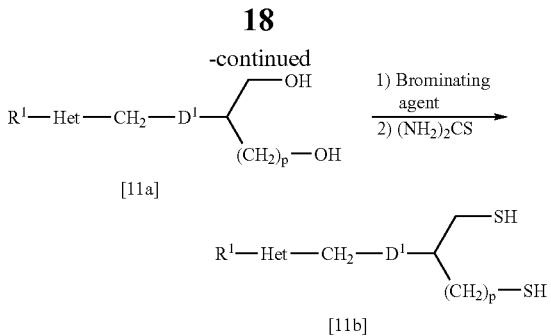

wherein $R^1$, Het, $D^1$, p, T and L have the same meaning as defined above.

The compound [51] can be obtained by dehydrating condensation of a compound [50] and acetone in an appropriate solvent (e.g., benzene) in the presence of an acidic catalyst (e.g., p-toluenesulfonic acid).

The compound [52] can be obtained by adding tri-n-butylphosphine and copper iodide to the compound [51] in an appropriate solvent (e.g., anhydrous tetrahydrofuran) and allowing to react with the compound [12] at temperature −60° C. or below. Magnesium can be used in place of tri-n-butylphosphine and copper iodide.

The compound [11a] can be obtained by treating the compound [52] in an appropriate solvent (e.g., ethanol or methanol) under an acidic condition (e.g., in the presence of pyridinium p-toluenesulfonate) at 0 to 100° C.

The compound [11b] can be obtained by converting the compound [11a] into a bromide through reaction with a brominating agent (e.g., triphenylphosphine/carbon tetrabromide or phosphorus tribromide) in an appropriate solvent (e.g., tetrahydrofuran, benzene), and then reacting with thiourea at −20 to 100° C.

Preparation of Compound [50a]

Among the compounds of the formula [50] used as the starting material in the preparation of the compound [11a] above, compounds [50a] wherein p is 1 can be prepared according to the following processes.

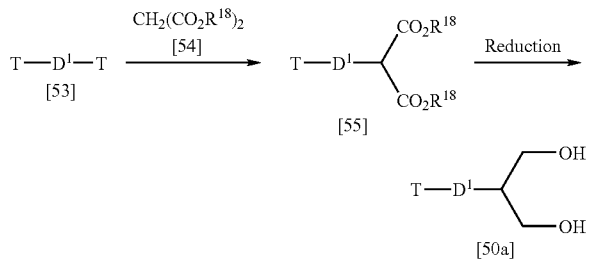

wherein $D^1$ and T have the same meaning as defined above, and $R^{18}$ is alkyl.

The compound [55] can be obtained by reacting a compound [53] and a malonic acid diester [54] in an appropriate solvent (e.g., anhydrous tetrahydrofuran) in the presence of a basic catalyst (e.g., sodium hydride) at −50 to 100° C.

The compound [50a] can be obtained by subjecting the compound [55] to the reaction in a manner similar to that described in PROCESS I above.

Preparation of Compound [50b]

Among the compounds of the formula [50] used as the starting material in the preparation of the compound [11a] above, compounds [50b] wherein p is 0 can be prepared according to the following processes.

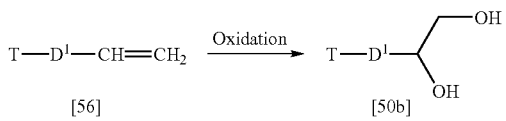

wherein $D^1$ and T have the same meaning as defined above.

The compound [50b] can be obtained by reacting a compound [56] with an oxidizing agent (e.g., osmium tetroxide) in an appropriate solvent (e.g., diethyl ether) at −20 to 50° C.

Preparation of Compound [50c]

Among the compounds of the formula [50] used as the starting material in the preparation of the compound [11a] above, compounds [50c] wherein p is 2 can be prepared according to the following processes.

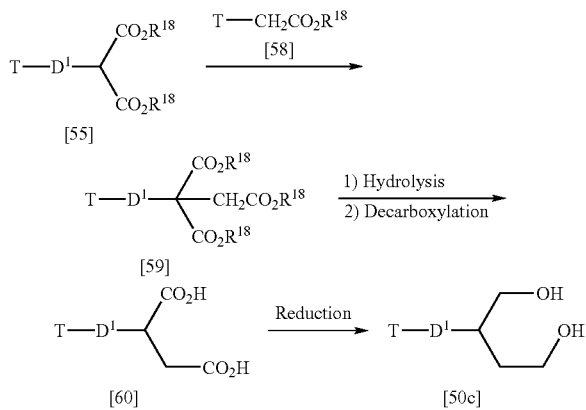

wherein $D^1$, T and $R^{18}$ have the same meaning as defined above.

The compound [59] can be obtained by reacting a compound [55] and a compound [58] in an appropriate solvent (e.g., tetrahydrofuran or ethanol) in the presence of a base (e.g., sodium alkoxide such as sodium ethoxide or sodium hydride) at −20° C. to room temperature.

The compound [60] can be obtained by subjecting the compound [59] to hydrolysis in a manner similar to that described in PROCESS G above followed by decarboxylation reaction by heating at 50 to 150° C. in the absence of a solvent or in an appropriate solvent (e.g., xylene, toluene, ethyl acetate, or a mixture thereof).

The compound [50c] can be obtained by subjecting the compound [60] to reduction in a manner similar to that described in PROCESS I above.

The compound [50c] can also be obtained by subjecting the compound [60] to esterification in a conventional manner followed by reduction in a manner similar to that described above.

Preparation of Compounds [11c] and [11d]

Among compounds of the formula [11] used as the starting material in the PROCESS A, those wherein Het is a group of the formula [5a], D is $D^1$-$CH_2$, p is 1, and Y is oxygen (compound [11c]) or sulfur (compound [11d]) can be prepared according to the following processes.

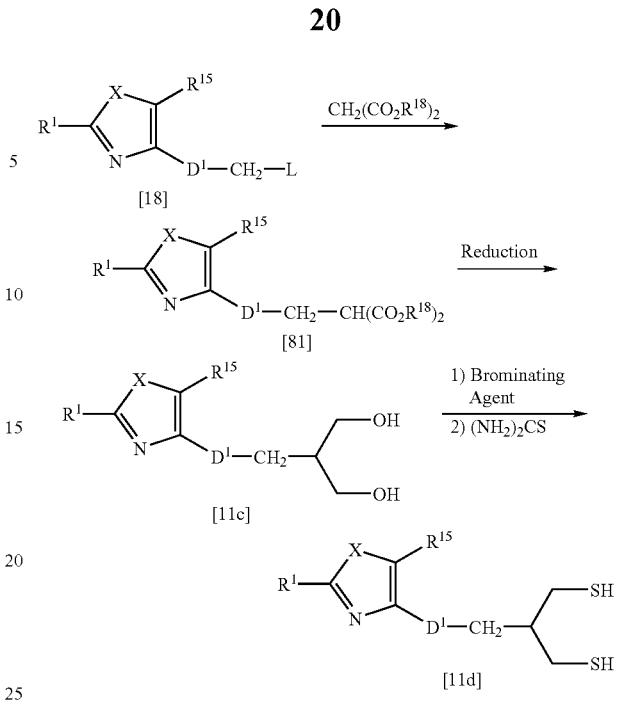

wherein $R^1$, $R^{15}$, $R^{18}$, $D^1$, X and L have the same meaning as defined above.

The compound [81] can be obtained by reacting a compound [18] and a malonic acid dialkyl in an appropriate solvent (e.g., tetrahydrofuran or ethanol) in the presence of a base (e.g., sodium alkoxide such as sodium ethoxide or sodium hydride) at −20° C. to room temperature.

The compound [11c] can be obtained by subjecting the compound [81] to the reaction in a manner similar to that described in PROCESS I above.

The compound [11d] can be obtained by subjecting the compound [11c] to the reaction similar to that wherein the compound [11b] is obtained from the compound [11a].

Preparation of Compound [13]

The compound [13] used as the starting material in the PROCESS B can be prepared according to the following processes.

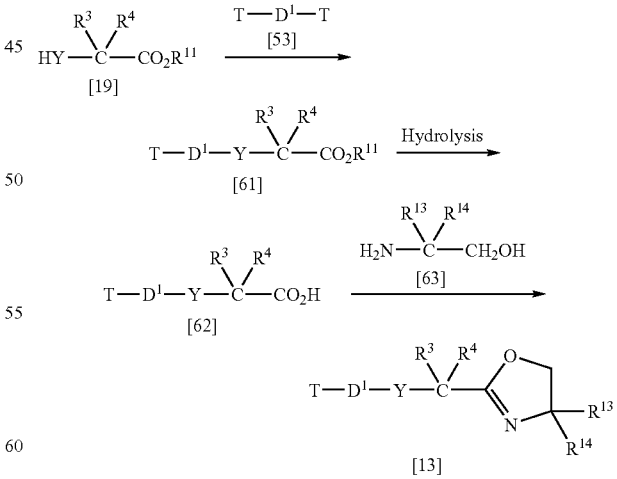

wherein $R^3$, $R^4$, $R^{11}$, $R^{13}$, $R^{14}$, $D^1$, Y and T have the same meaning as defined above.

The compound [61] can be obtained by reacting the compound [19] and compound [53] in a manner similar to that described in the PROCESS E.

The compound [62] can be obtained by treating the compound [61] in a manner similar to the hydrolysis described in the PROCESS G above.

The compound [13] can be obtained by reacting the compound [62] and compound [63] in an appropriate solvent (e.g., toluene) at 90 to 15° C.

Preparation of Compound [16]

The compound [16] used as the starting material in the PROCESS C can be prepared according to the following processes.

$$T-CH_2-D^2-E \xrightarrow{Ph_3P} Ph_3P^+-CH_2-D^2-E \quad T^-$$
$$[64] \qquad\qquad\qquad [16]$$

wherein E, $D^2$, T and Ph have the same meaning as defined above.

The compound [16] can be obtained by reacting the compound [64] and triphenylphosphine in a solvent similar to that described in the PROCESS A above at −20 to 150° C.

Preparation of Compound [17]

The compound [17] used as the starting material in the PROCESS D can be prepared according to the following processes.

$$R^1-CO-T + H_2N-\underset{CO_2R^{18}}{\overset{CO_2R^{18}}{\diagup}} \longrightarrow$$
$$[65] \qquad [66]$$

$$R^1-CONH-\underset{CO_2R^{18}}{\overset{CO_2R^{18}}{\diagup}} \xrightarrow{T-D-E^1 \; [68]}$$
$$[67]$$

$$R^1-CONH-\underset{CO_2R^{18}}{\overset{CO_2R^{18}}{\diagup}}D-E^1 \xrightarrow{\text{1) Hydrolysis} \atop \text{2) Decarboxylation}}$$
$$[69]$$

$$R^1-CONH-\underset{D-E^2}{\overset{CO_2H}{\diagup}} \xrightarrow{(R^{15}CO)_2O \; [71]}$$
$$[70]$$

$$R^1-CONH-\underset{D-E^2}{\overset{COR^{15}}{\diagup}} \xrightarrow[\text{or Alkylating agent}]{R^{11}-OH \; [73]}$$
$$[72]$$

$$R^1-CONH-\underset{D-E^1}{\overset{COR^{15}}{\diagup}}$$
$$[17]$$

wherein $R^1$, $R^{11}$, $R^{15}$, $R^{18}$, $E^1$, $E^2$, D and T have the same meaning as defined above.

The compound [67] can be obtained by reacting the compound [65] and compound [66] in a solvent similar to that described in the PROCESS A above in the presence of a base (e.g., triethylamine or dimethylaniline) at −20 to 150° C.

The compound [69] can be obtained from the compound [67] and [68] in a manner similar to that used for the preparation of the compound [59] above.

The compound [70] can be obtained from the compound [69] in a manner similar to that used for the preparation of the compound [60] above.

The compound [72] can be obtained by allowing the compound [70] and compound [71] to react in an appropriate solvent (e.g., pyridine) at 50 to 110° C., and then at 30 to 100° C. after addition of water.

The compound [17] can be obtained by subjecting the compound [72] to the reaction similar to that described in the PROCESS G above wherein the compound [1g] is obtained from the compound [1h].

Preparation of Compound [68a]

Among compounds of the formula [68] used as the starting material in the preparation of the compound [17] above, the compound [68a] wherein $E^1$ is a group of the formula [31] can be prepared according to the following processes.

$$T-D\underset{(CH_2)_{\overline{p}}-YH}{\overset{YH}{\diagup}} \xrightarrow{R^3COCO_2R^{11} \; [22]}$$
$$[74]$$

$$T-D\underset{(CH_2)_{\overline{p}}-Y}{\overset{Y}{\diagup}}\underset{CO_2R^{11}}{\overset{R^3}{\diagdown}}$$
$$[68a]$$

wherein D, T, Y, p, $R^3$ and $R^{11}$ have the same meaning as defined above.

The compound [68a] can be obtained by reacting the compound [22] and compound [74] which can be prepared in the same manner as the compound [50], in a manner similar to that described in the PROCESS A above.

Preparation of Compound [68b]

Among compounds of the formula [68]-used as the starting material in the preparation of the compound [17] above, compounds [68b] wherein $E^1$ is a group of the formula [41] can be prepared according to the following processes.

$$HY-\underset{[19]}{\overset{R^3\;R^4}{\underset{|}{C}}}-CO_2R^{11} \xrightarrow{T-D-T \; [75]}$$

$$T-D-Y-\underset{[68b]}{\overset{R^3\;R^4}{\underset{|}{C}}}-CO_2R^{11}$$

wherein D, T, Y, $R^3$, $R^4$ and $R^{11}$ have the same meaning as defined above.

The compound [68b] can be obtained by reacting the compound [19] and the compound [75] in a manner similar to that described in the preparation of compound [61] above.

Preparation of Compound [18]

The compound [18] used as the starting material in the PROCESS E can be prepared according to the following processes.

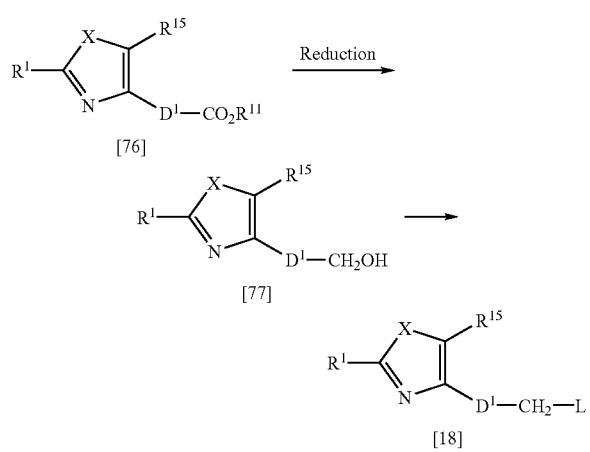

wherein $R^1$, $R^{11}$, $R^{15}$, X, $D^1$ and L have the same meaning as defined above.

The compound [77] can be obtained from the compound [76] obtained by a method as described in the PROCESS D above, in accordance with a method similar to that described in the PROCESS I above.

The compound [18] can be obtained by reacting the compound [77] and a brominating agent (e.g., triphenylphosphine/carbon tetrabromide) or a sulfonyl halide (e.g., p-toluenesulfonyl chloride) in a solvent similar to that described in the PROCESS A above at −20 to 150° C.

Preparation of Compound [21]

The compound [21] used as the starting material in the PROCESS F can be prepared according to the following processes.

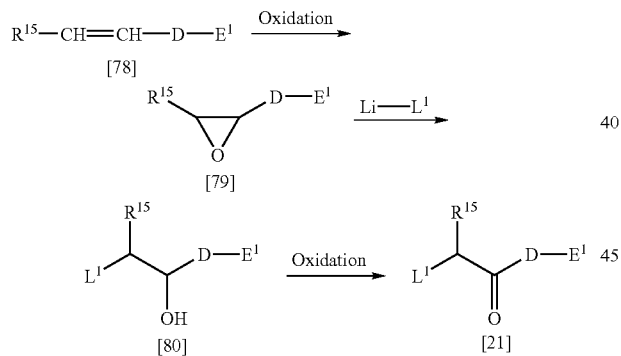

wherein $R^{15}$, D, $E^1$ and $L^1$ have the same meaning as defined above.

The compound [79] can be obtained by reacting a compound, [78] with an oxidizing agent (e.g., m-chloroperbenzoic acid) in an appropriate solvent (e.g., dichloromethane) at −10° C. to room temperature.

The compound [80] can be obtained by reacting the compound [79] with lithium chloride or lithium bromide in an appropriate solvent (e.g., anhydrous tetrahydrofuran) at room temperature.

The compound [21] can be obtained by reacting the compound [80] with a Jones reagent (e.g., conc. sulfuric acid and chromium (VI) oxide) at room temperature.

The compound of the present invention has blood triglyceride lowering effect and LDL-C lowering effect, and therefore is useful in the prevention and treatment of diseases such as hyperlipidemia, which are caused by elevated blood triglyceride level or total cholesterol level.

The present compounds showed various effects in KK-AY mouse, NIDDM model animal which develops hypertriglyceridemia, hyperglycemia and hyperinsulinemia, such as blood triglyceride lowering effect, very low density lipoprotein cholesterol (hereinafter, referred to as "VLDL-C") lowering effect, LDL-C lowering effect, and blood glucose lowering effect, blood insulin lowering effect, or HDL-C increasing effect or atherogenic index lowering effect, and are expected to be an especially excellent preventive or therapeutic agent for arteriosclerosis in comparison with known compounds. Further, the toxicity of the present compounds is low enough compared to the effective dose.

Accordingly, the compounds and pharmaceutical compositions of the present invention are not only useful in the prevention and treatment of arteriosclerosis caused by hyperlipidemia but also applicable to prevention and treatment of, for example, myocardial infarction, coronary artery diseases including reocclusion after percutaneous transluminal coronary angioplasty (PTCA), angina pectoris and ischemic heart disease caused by coronary artery diseases, cerebral infarction including cortical branch infarction and penetration branch infarction, thrombus and arteriosclerosis caused by the same, and the like.

Further, the compounds and pharmaceutical compositions of the present invention can be used in the prevention and treatment of obesity, hypertension, diabetes mellitus, especially non insulin-dependent diabetes mellitus.

When the compound of the invention is administered as a medicine, it can be administered to mammals inclusive of humans as it is or as a pharmaceutical composition containing the compound in a pharmaceutically acceptable, non-toxic and inert carrier at a concentration of, for example, 0.1% to 99.5%, preferably 0.5% to 90%.

Examples of usable carrier include solid, semisolid, or liquid diluents, fillers, and other formulation auxiliaries, and at least one of them is employed. The pharmaceutical composition is preferably administered in a unit dosage form. The pharmaceutical composition of the present invention can be administered intravenously, orally, into tissues, locally (e.g. transdermally) or rectally. A dosage form suited for each administration method is of course employed. The oral administration is especially preferred.

The dosage of the pharmaceutical composition for prevention or treatment of arteriosclerosis should preferably be adjusted in consideration of conditions of the patient such as age, body weight; the route of administration, nature and severity of disease; but the daily dosage of the compound of present invention as an active ingredient for adult can generally be 0.1–100 mg/human, preferably 0.5–20 mg/human. The dose range above is not critical and a lower dosage under the said range may be sufficient in some cases, while a higher dosage over the said range may be needed in other cases. The daily dosage may be administered in 2 to 3 divisions.

When the pharmaceutical composition is to be used in the prevention or treatment of diabetes mellitus or other diseases, the dose of the present compound can be adjusted in accordance with those set forth above.

Best Mode for Carrying Out the Invention

The following Examples including Reference Examples, Working Examples, Test Examples and Formulation Examples are provided to further illustrate the present invention in more detail, which should not be construed as limiting the scope of the present invention.

REFERENCE EXAMPLE 1

Diethyl (4-chlorobutyl)malonate

To 458 ml of dry tetrahydrofuran (THF) was added 13.4 g of 60% sodium hydride, and 160.6 g of diethyl malonate was added dropwise with stirring under ice-cooling. After addition, stirring was continued for 15 minutes, and 57.3 g of 1-bromo-4-chlorobutane was added. The mixture was stirred for 50 hours at room temperature. The reaction solution was poured into ice-cold water, neutralized with dilute hydrochloric acid and extracted with ethyl acetate. The organic layer was washed with brine, dried over anhydrous magnesium sulfate and concentrated. The residue was distilled under reduced pressure to provide 26.8 g of the objective compound as colorless oil.

B.p. 127–130° C. (5 mmHg).

The following compounds were prepared by the same procedure as described in Reference Example 1.

Diethyl (3-chloropropyl)malonate; and

Diethyl (5-chloropentyl)malonate.

REFERENCE EXAMPLE 2

Diethyl (5-hexenyl)malonate

To 120 ml of dry tetrahydrofuran (THF) was added 4.9 g of 60% sodium hydride, and 29.5 g of diethyl malonate was added dropwise with stirring under ice-cooling. After addition, stirring was continued for 15 minutes, and then 10 g of 6-bromo-1-hexen was added to the mixture and heated to reflux for 21 hours. The reaction solution was cooled, poured into ice-cold water, neutralized with dilute hydrochloric acid and extracted with ethyl acetate. The organic layer was washed with brine, dried over anhydrous magnesium sulfate and concentrated. The residue was purified by silica gel column chromatography (Wakogel® C-200, n-hexane: ethyl acetate=20:1) to provide 14.5 g of the objective compound as yellowish oil.

$^1$H-NMR (CDCl$_3$) δ: 1.23–1.47 (10H, m), 1.84–2.11 (4H, m), 3.28–3.37 (1H, m), 4.14–4.25 (4H, m), 4.91–5.05 (2H, m), 5.69–5.90 (1H, m).

REFERENCE EXAMPLE 3

6-Chloro-2-hydroxymethyl-1-hexanol

To 214 ml of dry ether was added 8 g of lithium aluminium hydride, and a solution of 26.7 g of diethyl (4-chlorobutyl)malonate/53 ml of dry ether was added dropwise with stirring under ice-cooling. After 1-hour-stirring at room temperature, the mixture was cooled with ice-cold water, and 173 ml of tetrahydrofuran/14.7 ml of water was added gradually. Then, 14.7 ml of 1N sodium hydroxide solution and 35 ml of water were added, stirred for 15 minutes, filtrated to remove insolubles. The filtrate was concentrated to provide 18.2 g of the objective compound as colorless oil.

$^1$H-NMR (CDCl$_3$) δ: 1.22–1.38 (2H, m), 1.42–1.58 (2H, m), 1.68–1.88 (3H, m), 2.36–2.44 (2H, m), 3.55 (2H, t), 3.61–3.72 (2H, m), 3.77–3.88 (2H, m).

The following compounds were prepared by the same procedure as described in Reference Example 3.

5-Chloro-2-hydroxymethyl-1-pentanol;

7-Chloro-2-hydroxymethyl-1-heptanol; and

2-Hydroxymethyl-7-octen-1-ol.

REFERENCE EXAMPLE 4

Methyl c-5-(4-chlorobutyl)-2-methyl-1,3-dioxane-r-2-carboxylate

To 270 ml of acetonitrile were added 18 g of 6-chloro-2-hydroxymethyl-1-hexanol and 44 g of methyl pyruvate. To the mixture solution, 65.2 g of boron trifluoride etherate (about 47%) was added with stirring at room temperature, and stirred for 14 hours. The reaction mixture was poured into a solution of sodium bicarbonate in ice-cold water and extracted with ethyl acetate. The organic layer was washed with brine, dried over anhydrous magnesium sulfate and concentrated. The residue was purified by silica gel column chromatography (Wakogel® C-200, n-hexane: ethyl acetate=10:1) to provide 14.8 g of the objective compound as yellowish oil.

$^1$H-NMR (CDCl$_3$) δ: 0.99–1.11 (2H, m), 1.37–1.55 (5H, m), 1.68–1.82 (2H, m), 1.95–2.09 (1H, m), 3.41 (2H, t), 3.48–3.60 (2H, m), 3.83 (3H, s), 3.92–4.00 (2H, m).

The following compounds were prepared by the same procedure as described in Reference Example 4.

Methyl c-5-(3-chloropropyl)-2-methyl-1,3-dioxane-r-2-carboxylate; and

Methyl c-5-(5-chloropentyl)-2-methyl-1,3-dioxane-r-2-carboxylate.

REFERENCE EXAMPLE 5

Diethyl [4-(tetrahydro-2H-pyran-2-yloxy)-(Z)-2-butenyl]malonate

2-[4-Chloro-(Z)-2-butenyloxy]tetrahydro-2H-pyran (100 g) was dissolved in 2000 ml of dry tetrahydrofuran/600 ml of dry N,N-dimethylformamide. To the solution was added 100 g of diethyl malonate, and then 25 g of 60% sodium hydride with stirring under ice-cooling, and the mixture was stirred at room temperature for 1 hour. The reaction mixture was poured into ice-cold water and extracted with ethyl acetate. The organic layer was washed with brine, dried over anhydrous magnesium sulfate and concentrated. The residue was purified by silica gel column chromatography (Wakogel® C-200, n-hexane: ethyl acetate=9:1) to provide 65.5 g of the objective compound as oil.

$^1$H-NMR (CDCl$_3$) δ: 1.27 (6H, t), 1.50–1.90 (6H, m), 2.67 (2H, t), 3.39 (1H, t), 3.45–3.60 (1H, m), 3.80–3.95 (1H, m), 4.05–4.35 (6H, m), 4.61 (1H, dd), 5.45–5.75 (2H, m).

REFERENCE EXAMPLE 6

2-Hydroxymethyl-6-(tetrahydro-2H-pyran-2-yloxy)-(Z)-4-hexen-1-ol

Diethyl [4-(tetrahydro-2H-pyran-2-yloxy)-(Z)-2-butenyl]malonate (65.5 g) was dissolved in 650 ml of dry tetrahydrofuran, and 15.1 g of sodium borohydride was added thereto. A solution of 110 g of methanol/275 ml of tetrahydrofuran was added dropwise gradually with stirring under heating to reflux. Then, 13.18 g of lithium chloride and 11 g of sodium borohydride were added and refluxed for 1.5 hours. The reaction solution was cooled and poured into ice-cold water and extracted with ethyl acetate. The organic layer was washed with brine, dried over anhydrous magnesium sulfate and concentrated. The residue was purified by silica gel column chromatography (Wakogel® C-200, chloroform) to provide 22.8 g of the objective compound as oil.

$^1$H-NMR (CDCl$_3$) δ: 1.40–1.90 (7H, m), 2.20 (2H, br), 2.26 (2H, ddd), 3.46–3.90 (6H, m), 4.10–4.30 (2H, m), 4.68 (1H, dd), 5.50–5.80 (2H, m).

REFERENCE EXAMPLE 7

Methyl c-5-[4-hydroxy-(Z)-2-butenyl]-2-methyl-1,3-dioxane-r-2-carboxylate

Boron trifluoride etherate (about 47%, 26.8 g) was added dropwise to a solution of 21.79 g of 2-hydroxymethyl-6-(tetrahydro-2H-pyran-2-yloxy)-(Z)-4-hexen-1-ol, 430 ml of acetonitrile and 38.57 g of methyl pyruvate under ice-cooling, and the mixture was stirred for 15 hours at room temperature. The reaction solution was poured into a solution of sodium bicarbonate in ice-cold water and extracted with ethyl acetate. The organic layer was washed with brine, dried over anhydrous magnesium sulfate and concentrated. The residue was purified by silica gel column chromatography (Wakogel® C-200, n-hexane: ethyl acetate=7:1) to provide 5.36 g of the objective compound as oil.

$^1$H-NMR (CDCl$_3$) δ: 1.51 (3H, s), 1.85 (2H, dd), 1.95–2.20 (1H, m), 3.43 (2H, dd), 3.84 (3H, s), 3.95 (2H, dd), 4.14 (2H, dd), 5.44 (1H, ddd), 5.70 (1H, ddd).

REFERENCE EXAMPLE 8

Methyl c-5-[4-chloro-(Z)-2-butenyl]-2-methyl-1,3-dioxane-r-2-carboxylate

Methyl c-5-[4-hydroxy-(Z)-2-butenyl]-2-methyl-1,3-dioxane-r-2-carboxylate (538 mg) was dissolved in 12 ml of N,N-dimethyl formamide, and 1.13 g of 2,4,6-trimethylpyridine and 396 mg of lithium chloride were added. After 1.07 g of methanesulfonyl chloride was added dropwise under ice-cooling, the mixture was stirred for 9 hours at room temperature. The reaction solution was poured into ice-cold water, 0.5 N hydrochloric acid was added thereto and the solution was extracted with ethyl acetate. The organic layer was washed with brine, dried over anhydrous magnesium sulfate and concentrated. The residue was purified by silica gel column chromatography (Wakogel® C-200, n-hexane: ethyl acetate=9:1) to provide 561 mg of the objective compound as oil.

$^1$H-NMR (CDCl$_3$) δ: 1.52 (3H, s), 1.89 (2H, dd), 2.00–2.20 (1H, m), 3.45 (2H, dd), 3.85 (3H, s), 3.95 (2H, dd), 4.00 (2H, dd), 5.53 (1H, ddd), 5.72 (1H, ddd).

REFERENCE EXAMPLE 9

Methyl c-5-[4-iodo-(E)-2-butenyl]-2-methyl-1,3-dioxane-r-2-carboxylate

Methyl c-5-[4-chloro-(Z)-2-butenyl]-2-methyl-1,3-dioxane-r-2-carboxylate (300 mg) was dissolved in 5 ml of acetone, and sodium iodide was added thereto. The mixture was heated to reflux for 2 hours. The reaction solution was cooled, ice-cold water was added thereto and the mixture was extracted with ethyl acetate. The organic layer was washed with brine, dried over anhydrous magnesium sulfate and concentrated to provide 353 mg of the objective compound as oil.

$^1$H-NMR (CDCl$_3$) δ: 1.51 (3H, s), 1.79 (2H, dd), 2.00–2.20 (1H, m), 3.41 (2H, dd), 3.81 (2H, dd), 3.84 (3H, t), 3.93 (2H, dd), 5.48–5.93 (2H, m).

REFERENCE EXAMPLE 10

Methyl c-5-(4-iodobutyl)-2-methyl-1,3-dioxane-r-2-carboxylate

Methyl c-5-(4-chlorobutyl)-2-methyl-1,3-dioxane-r-2-carboxylate (14.8 g) was dissolved in 148 ml of acetone, and 44.2 g of sodium iodide was added. The mixture was stirred for 22.5 hours at 40° C. The reaction solution was concentrated, water was added to the residue, and the solution was extracted with ethyl acetate. The organic layer was washed with brine, dried over anhydrous magnesium sulfate and concentrated to give 19.9 g of the objective compound as oil.

$^1$H-NMR (CDCl$_3$):0.99–1.10 (2H, m), 1.30–1.45 (2H, m), 1.51 (3H, s), 1.72–1.86 (2H, m), 1.97–2.08 (1H, m), 3.16 (2H, t), 3.40 (2H, t), 3.83 (3H, s), 3.92–4.00 (2H, m).

The following compounds were prepared by the same procedure as described in Reference Example 10.

Methyl c-5-(3-iodopropyl)-2-methyl-1,3-dioxane-r-2-carboxylate, and

Methyl c-5-(5-iodopentyl)-2-methyl-1,3-dioxane-r-2-carboxylate.

REFERENCE EXAMPLE 11

6-Bromo-1-(tetrahydro-2H-pyran-2-yloxy)-2-hexyne

Under argon flow, 13.46 g of 3-(tetrahydro-2H-pyran-2-yloxy)-1-propyne was dissolved in 135 ml of anhydrous tetrahydrofuran, and 60 ml of 1.6 N n-butyllithium hexane solution was added dropwise over 20 minutes with stirring at −10° C. of inner temperature. The mixture was stirred for 1 hour at the same temperature. After stirring for additional 1 hour at room temperature, the inner temperature was changed to −3° C., and 16.7 ml of hexamethylphosphoric triamide (HMPA) was added to the mixture. Then 58.14 g of 1,3-dibromopropane was added in a portion at −10° C. of inner temperature, and the mixture was stirred for 12 hours at room temperature. The reaction solution was poured into ice-cold water, extracted with ether, washed with water, dried over anhydrous magnesium sulfate and concentrated. The residue was distilled under reduced pressure to give 12.0 g of the objective compound as colorless oil.

B.p. 121–126° C. (5 mmHg).

REFERENCE EXAMPLE 12

Methyl 2-(6-bromohexyloxy)-2-methylpropionate

To 120 ml of dry N,N-dimethylformamide, 4.0 g of 60% sodium hydride was added. To the mixture was added dropwise 11.81 g of methyl 2-hydroxyisobutyrate with stirring under ice-cooling, and stirred for 10 minutes. Then, 122 g of 1,6-dibromohexane was added and stirred for 15 hours at room temperature. The reaction solution was poured into ice-cold water, extracted with ethyl acetate, washed with brine, dried over anhydrous magnesium sulfate and concentrated. The residue was purified by silica gel column chromatography (Wakogel® C-200, n-hexane: ethyl acetate= 20:1) to provide 6.25 g of the objective compound as yellowish oil.

$^1$H-NMR (CDCl$_3$) δ: 1.42–1.65 (12H, m), 1.80–1.94 (2H, m), 3.32–3.45 (4H, m), 3.73 (3H, s).

The following compounds were prepared by the same procedure as described in Reference Example 12.

Methyl 2-(5-bromopentyloxy)-2-methylpropionate,

Methyl 2-(7-bromoheptyloxy)-2-methylpropionate,

Methyl 2-(8-bromooctyloxy)-2-methylpropionate,

Ethyl 2-methyl-2-[6-(tetrahydro-2H-pyran-2-yloxy)-4-hexynyloxy]propionate,

Ethyl 2-(6-bromohexyloxy)-2-methylpropionate, and

Methyl 2-[6-(5-methyl-2-phenyloxazol-4-yl)-(E)-4-hexenyloxy]-2-methylpropionate.

REFERENCE EXAMPLE 13

Ethyl 2-(6-hydroxy-4-hexynyloxy)-2-methylpropionate

Ethyl 2-methyl-2-[6-(tetrahydro-2H-pyran-2-yloxy)-4-hexynyloxy]propionate (3.72 g) was dissolved in 37 ml of ethanol, and 15.372 mg of Amberlyst® was added thereto and the mixture was stirred for 1 hour at 55–60° C. After cooling, the mixture was filtrated and the filtrate was concentrated. The residue was purified by silica gel column chromatography (Wakogel® C-200, n-hexane: ethyl acetate=9:1–3:1) to provide 1.98 g of the objective compound as pale yellow oil.

$^1$H-NMR (CDCl$_3$) δ: 1.29 (3H, t), 1.42 (6H, s), 1.70–1.83 (2H, m), 2.30–2.39 (2H, m), 3.44–3.50 (2H, m), 4.14–4.26 (4H, m).

REFERENCE EXAMPLE 14

Methyl 2-methyl-2-(8-nonenyloxy)propionate

To 500 ml of dry N,N-dimethylformamide, 17 g of 60% sodium hydride was added, and 48 g of methyl 2-hydroxyisobutyrate was added dropwise with stirring under ice-cooling, and stirred for 10 minutes. Then, 100 g of 9-bromo-1-nonene (purity: 63.4%) was added, and the mixture was stirred for 15 hours at room temperature. The reaction solution was poured into ice-cold water, extracted with ethyl acetate, washed with brine, dried over anhydrous magnesium sulfate and concentrated. The residue was distilled under reduced pressure to give 29.9 g of the objective compound as yellowish oil.

B.p. 124–127° C. (8 mmHg).

The following compounds were prepared by the same procedure as described in Reference Example 14.

Methyl 2-(6-heptenyloxy)-2-methylpropionate,
Methyl 2-methyl-2-(7-octenyloxy)propionate and
Methyl 2-(9-decenyloxy)-2-methylpropionate.

REFERENCE EXAMPLE 15

Methyl 2-(8,9-epoxynonyloxy)-2-methylpropionate

Methyl 2-methyl-2-(8-nonenyloxy)propionate (40 g) was dissolved in 320 ml of methylene chloride, and 40.8 g of 70% 3-chloroperbenzoic acid was added with stirring under ice-cooling, and the mixture was stirred for 15 hours at room temperature. The reaction solution was filtrated to remove insolubles, and the filtrate was concentrated. The residue was dissolved in n-hexane and washed 4 times with aqueous 10% potassium carbonate solution, washed with water, dried over anhydrous magnesium sulfate and concentrated to give 43.2 g of the objective compound as colorless oil.

$^1$H-NMR (CDCl$_3$) δ: 1.25–1.70 (18H, m), 2.44–2.48 (1H, m), 2.72–2.77 (1H, m), 2.85–2.97 (1H, m), 3.34 (2H, t), 3.73 (3H, s).

The following compounds were prepared by the same procedure as described in Reference Example 15.

Methyl 2-(6,7-epoxyheptyloxy)-2-methylpropionate,
Methyl 2-(7,8-epoxyoctyloxy)-2-methylpropionate,
Methyl 2-(9,10-epoxydecyloxy)-2-methylpropionate and
Methyl c-5-(5,6-epoxyhexyl)-2-methyl-1,3-dioxane-r-2-carboxylate.

REFERENCE EXAMPLE 16

Methyl 2-(9-chloro-8-hydroxynonyloxy)-2-methylpropionate

Methyl 2-(8,9-epoxynonyloxy)-2-methylpropionate (26 g) was dissolved in 260 ml of dry tetrahydrofuran, and 6.8 g of lithium chloride and 7 g of acetic acid were added and the mixture was stirred for 22 hours at room temperature. The reaction solution was poured into ice-cold water, extracted with ethyl acetate, washed with saturated sodium hydrogen carbonate solution and brine, dried over anhydrous magnesium sulfate and concentrated to give 31.7 g of the objective compound as oil.

The following compounds were prepared by the same procedure as described in Reference Example 16.

Methyl 2-(7-chloro-6-hydroxyheptyloxy)-2-methylpropionate,
Methyl 2-(8-chloro-7-hydroxyoctyloxy)-2-methylpropionate,
Methyl 2-(10-chloro-9-hydroxydecyloxy)-2-methylpropionate and
Methyl c-5-(6-chloro-5-hydroxyhexyl)-2-methyl-1,3-dioxane-r-2-carboxylate.

REFERENCE EXAMPLE 17

Methyl 2-(9-chloro-8-oxononyloxy)-2-methylpropionate

Methyl 2-(9-chloro-8-hydroxynonyloxy)-2-methylpropionate (31 g) was dissolved in 465 ml of acetone, and 46 ml of Jones reagent prepared by adding 10.2 ml of conc. sulfuric acid and 12 g of chromic (VI) oxide to 45 ml of water was added dropwise with stirring under ice-cooling. After 3-hour-stirring at room temperature, an excess amount of Jones reagent was decomposed by adding isopropyl alcohol. The reaction mixture was poured into ice-cold water, extracted with ethyl acetate, washed with brine, dried over anhydrous magnesium sulfate and concentrated. The residue was purified by silica gel column chromatography (Wakogel® C-200, n-hexane: ethyl acetate=7.5:1) to provide 18.16 g of the objective compound as oil.

$^1$H-NMR (CDCl$_3$) δ: 1.24–1.40 (6H, m), 1.41 (6H, s), 1.45–1.75 (4H, m), 2.58 (2H, t), 3.34 (2H, t), 3.73 (3H, s), 4.07 (2H, s).

The following compounds were prepared by the same procedure as described in Reference Example 17.

Methyl 2-(7-chloro-6-oxoheptyloxy)-2-methylpropionate,
Methyl 2-(8-chloro-7-oxooctyloxy)-2-methylpropionate,
Methyl 2-(10-chloro-9-oxodecyloxy)-2-methylpropionate and
Methyl c-5-(6-chloro-5-oxohexyl)-2-methyl-1,3-dioxane-r-2-carboxylate.

REFERENCE EXAMPLE 18

Diethyl p-toluoylaminomalonate

Diethyl aminomalonate hydrochloride (20.5 g) was suspended into 180 ml of methylene chloride, and 29.4 g of triethylamine was added while cooling with ice-cold water. After 30-minute-stirring, 15 g of p-toluoyl chloride was added dropwise, and the mixture was stirred for 24 hours at room temperature. The reaction solution was washed with water, dilute hydrochloric acid, and water, dried over anhydrous magnesium sulfate and concentrated. To the residue was added isopropyl ether, and the resultant crystals were collected by filtration and dried to provide 25.9 g of the objective compound as white crystal. M.p. 101–102° C.

The following compounds were prepared by the same procedure as described in Reference Example 18.

Diethyl benzoylaminomalonate,
Diethyl (4-chlorobenzoyl)aminomalonate,

Diethyl (4-fluorobenzoylamino)malonate,
Diethyl (4-trifluoromethylbenzoyl)aminomalonate,
Diethyl (4-tert-butylbenzoyl)aminomalonate and
Diethyl (4-ethylbenzoyl)aminomalonate.

REFERENCE EXAMPLE 19

Ethyl c-5-[5,5-bis(ethoxycarbonyl)-5-(p-toluoylamino)-pentyl]-2-methyl-1,3-dioxane-r-2-carboxylate To 27 ml of dry ethanol, 6.6 g of 20% sodium ethoxide-ethanol solution and 5.4 g of diethyl p-toluoylaminomalonate were added, and stirred for 30 minutes at room temperature. Then, a solution of 6.3 g of methyl c-5-(4-iodobutyl)-2-methyl-1,3-dioxane-r-2-carboxylate/5.4 ml of dry ethanol was added dropwise and stirred for 15 hours at 50–60° C. The reaction solution was poured into ice-cold water and extracted with ethyl acetate. The organic layer was washed with brine, dried over anhydrous magnesium sulfate and concentrated. The residue was purified by silica gel column chromatography (Wakogel® C-200, n-hexane: ethyl acetate=5:1) to provide 4.34 g of the objective compound as yellowish crystals. M.p. 60–63° C.

The following compounds were prepared by the same procedure as described in Reference Example 19.

Ethyl c-5-(4-benzoylamino-4,4-bis(ethoxycarbonyl)-butyl)-2-methyl-1,3-dioxane-r-2-carboxylate,
Ethyl c-5-(S-benzoylamino-5,5-bis(ethoxycarbonyl)-pentyl)-2-methyl-1,3-dioxane-r-2-carboxylate,
Ethyl c-5-(6-benzoylamino-6,6-bis(ethoxycarbonyl)-hexyl)-2-methyl-1,3-dioxane-r-2-carboxylate,
Ethyl c-5-[5,5-bis(ethoxycarbonyl)-5-(4-fluorobenzoylamino)pentyl]-2-methyl-1,3-dioxane-r-2-carboxylate,
Ethyl c-5-[5,5-bis(ethoxycarbonyl)-5-(4-trifluoromethylbenzoylamino)pentyl]-2-methyl-1,3-dioxane-r-2-carboxylate,
Ethyl c-5-[5-(4-tert-butylbenzoylamino)-5,5-bis-(ethoxycarbonyl)pentyl]-2-methyl-1,3-dioxane-r-2-carboxylate,
Ethyl c-5-[5-benzoylamino-5,5-bis(ethoxycarbonyl)-(E)-2-pentenyl]-2-methyl-1,3-dioxane-r-2-carboxylate,
5-(Benzolyamino-5,5-bis(ethoxycarbonyl)pentyl-2,2-dimethyl-1,3-dioxane,
Ethyl c-5-[5,5-bis(ethoxycarbonyl)-5-(4-chlorobenzoylamino)pentyl]-2-methyl-1,3-dioxane-r-2-carboxylate,
Ethyl c-S-[6,6-bis(ethoxycarbonyl)-6-(p-toluoylamino)-hexyl]-2-methyl-1,3-dioxane-r-2-carboxylate,
Ethyl c-5-[5,5-bis(ethoxycarbonyl)-5-(3-fluoro-4-methylbenzoylamino)pentyl]-2-methyl-1,3-dioxane-r-2-carboxylate and
Ethyl c-5-[5,5-bis(ethoxycarbonyl)-5-(4-ethylbenzoylamino)pentyl]-2-methyl-1,3-dioxane-r-2-carboxylate.

REFERENCE EXAMPLE 20

Ethyl 2-(7-benzoylamino-7,7-bis(ethoxycarbonyl)-heptyloxy)-2-methylpropionate

To 5 ml of dry ethanol, 675 mg of 20% sodium ethoxide-ethanol solution and 698 mg of diethyl benzoylaminomalonate were added, and stirred for 30 minutes at room temperature. Then, a solution of 914 mg of methyl 6-bromohexyloxy-2-methylpropionate/4 ml of dry ethanol was added dropwise, and stirred for 15 hours at 50–60° C. The reaction solution was poured into ice-cold water and extracted with ethyl acetate. The organic layer was washed with brine, dried over anhydrous magnesium sulfate and concentrated. The residue was purified by silica gel column chromatography (Wakogel® C-200, n-hexane: ethyl acetate=5:1) to provide 642 mg of the objective compound as yellowish oil.

$^1$H-NMR (CDCl$_3$) δ:1.10–1.37 (15H, m), 1.38 (6H, s), 1.42–1.60 (2H, m), 2.41–2.49 (2H, m), 3.30 (2H, t), 4.11–4.33 (6H, m), 7.40–7.60 (4H, m), 7.81–7.86 (2H, m).

The following compounds were prepared by the same procedure as described in Reference Example 20.

Ethyl 2-methyl-2-[7-(p-toluoylamino)-7,7-bis(ethoxycarbonyl)heptyloxy]propionate,
Ethyl 2-[7-benzoylamino-7,7-bis(ethoxycarbonyl)-4-heptynyloxy]-2-methylpropionate,
Ethyl 2-[7-(4-chlorobenzoylamino)-7,7-bis(ethoxycarbonyl)heptyloxy]-2-methylpropionate,
Ethyl 2-[7,7-bis(ethoxycarbonyl)-7-(4-fluorobenzoylamino)heptyloxy]-2-methylpropionate,
Ethyl 2-[7-(4-tert-butylbenzoylamino)-7,7-bis(ethoxycarbonyl)heptyloxy]-2-methylpropionate,
Ethyl 2-[6-benzoylamino-6,6-bis(ethoxycarbonyl)hexyloxy]-2-methylpropionate,
Ethyl 2-[8-benzoylamino-8,8-bis(ethoxycarbonyl)octyloxy]-2-methylpropionate,
Ethyl 5-benzoylamino-5,5-bis(ethoxycarbonyl)pentanoate,
Ethyl 6-benzoylamino-6,6-bis(ethoxycarbonyl)hexanoate,
Ethyl 5,5-bis(ethoxycarbonyl)-5-(p-toluoylamino)pentanoate and
5-(Benzoylamino)-1-bromo-5,5-bis(ethoxycarbonyl)-(E)-2-pentene.

REFERENCE EXAMPLE 21 c-5-[5-Carboxy-5-(p-toluoylamino)pentyl]-2-methyl-1,3-dioxane-r-2-carboxylic Acid Ethyl c-5-[5,5-bis(ethoxycarbonyl)-5-(p-toluoylamino)pentyl]-2-methyl-1,3-dioxane-r-2-carboxylate (4.2 g) was dissolved in 33.6 ml of ethanol, and a solution of 2.0 g of sodium hydroxide/8.4 ml of water was added. The mixture was heated to reflux for 5 hours. The reaction solution was concentrated. Water was added to the residue, and the mixture was acidified with hydrochloric acid and extracted with ethyl acetate. The organic layer was washed with brine, dried over anhydrous magnesium sulfate and concentrated to provide 3.23 g of yellowish oil. The resultant oil was stirred for 30 minutes at 130° C. to give 3.1 g of the objective compound as white crystals. M.p. 152–156° C.

The following compounds were prepared by the same procedure as described in Reference Example 21.

c-5-(4-Benzoylamino-4-carboxybutyl)-2-methyl-1,3-dioxane-r-2-carboxylic acid,
c-5-(5-Benzoylamino-5-carboxypentyl)-2-methyl-1,3-dioxane-r-2-carboxylic acid,
c-5-(6-Benzoylamino-6-carboxyhexyl)-2-methyl-1,3-dioxane-r-2-carboxylic acid,
c-5-[5-Carboxy-5-(4-fluorobenzoylamino)pentyl]-2-methyl-1,3-dioxane-r-2-carboxylic acid,
c-5-[5-Carboxy-5-(4-trifluoromethylbenzoylamino)-pentyl]-2-methyl-1,3-dioxane-r-2-carboxylic acid,
c-5-[5-(4-tert-Butylbenzoylamino)-5-carboxypentyl]-2-methyl-1,3-dioxane-r-2-carboxylic acid,
c-5-[5-Benzoylamino-5-carboxy-(E)-2-pentenyl]-2-methyl-1,3-dioxane-r-2-carboxylic acid, 5-(5-Benzoylamino-5-carboxypentyl)-2,2-dimethyl-1,3-dioxane,
2-(7-Benzoylamino-7-carboxyheptyloxy)-2-methylpropionic acid,
2-[7-Carboxy-7-(p-toluoylamino)heptyloxy]-2-methylpropionic acid,
2-(7-Benzoylamino-7-carboxy-4-heptynyloxy)-2-methylpropionic acid,
2-[7-Carboxy-7-(4-chlorobenzoylamino)heptyloxy]-2-methylpropionic acid,
2-[7-Carboxy-7-(4-fluorobenzoylamino)heptyloxy]-2-methylpropionic acid,
2-[7-(4-tert-Butylbenzoylamino)-7-carboxyheptyloxy)-2-methylpropionic acid,
2-(8-Benzoylamino-8-carboxyoctyloxy)-2-methylpropionic acid,
2-(6-Benzoylamino-6-carboxyhexyloxy)-2-methylpropionic acid,
5-Benzoylamino-5-carboxypentanoic acid,
6-Benzoylamino-6-carboxyhexanoic acid;
c-5-[5-Carboxy-5-(4-chlorobenzoylamino)pentyl]-2-methyl-1,3-dioxane-r-2-carboxylic acid,
c-5-[6-Carboxy-6-(p-toluoylamino)hexyl]-2-methyl-1,3-dioxane-r-2-carboxylic acid,
5-Carboxy-5-(p-toluoylamino)pentanoic acid,
c-5-[5-Carboxy-S-(3-fluoro-4-methylbenzoylamino)pentyl]-2-methyl-1,3-dioxane-r-2-carboxylic acid and
c-5-[5-Carboxy-5-(4-ethylbenzoylamino)pentyl]-2-methyl-1,3-dioxane-r-2-carboxylic acid.

REFERENCE EXAMPLE 22 c-5-[5-Acetyl-5-(p-toluoylamino)pentyl]-2-methyl-1,3-dioxane-r-2-carboxylic Acid c-5-[5-Carboxy-5-(p-toluoylamino)pentyl]-2-methyl-1,3-dioxane-r-2-carboxylic acid (3.1 g) was dissolved in 15.5 ml of pyridine, and 10.2 ml of acetic anhydride was added and stirred for 1 hour at 90° C. Then, 10.2 ml of water was added dropwise and stirred for 30 minutes at 90° C. The reaction solution was cooled, poured into ice-cold water, extracted with ethyl acetate, washed with brine, dried over anhydrous magnesium sulfate and concentrated. The residue was purified by silica gel column chromatography (Wakogel® C-200, chloroform: methanol=100:1) to provide 2.2 g of the objective compound as yellowish oil.

$^1$H-NMR (CDCl$_3$) δ: 0.99–1.10 (2H, m), 1.15–1.45 (4H, m), 1.54 (3H, s), 1.50–1.82 (1H, m), 1.84–2.15 (2H, m), 2.27 (3H, s), 2.40 (3H, s), 3.47 (2H, dd), 3.89–4.04 (2H, m), 4.82–4.92 (1H, m), 7.01 (1H, d), 7.22–7.27 (2H, m), 7.68–7.74 (2H, m).

The following compounds were prepared by the same procedure as described in Reference Example 22.

c-5-(4-Acetyl4-benzoylaminobutyl)-2-methyl-1,3-dioxane-r-2-carboxylic acid,
c-5-(5-Acetyl-5-benzoylaminopentyl)-2-methyl-1,3-dioxane-r-2-carboxylic acid,
c-5-(6-Acaetyl-6-benzoylaminohexyl)-2-methyl-1,3-dioxane-r-2-carboxylic acid,
c-5-[5-Acetyl-5-(4-fluorobenzoylamino)pentyl]-2-methyl-1,3-dioxane-r-2-carboxylic acid,
c-5-[5-Acetyl-5-(4-trifluoromethylbenzoylamino)pentyl]-2-methyl-1,3-dioxane-r-2-carboxylic acid,
c-5-[5-Acetyl-5-(4-tert-butylbenzoylamino)pentyl]-2-methyl-1,3-dioxane-r-2-carboxylic acid,
c-5-[5-Acetyl-5-benzoylamino-(E)-2-pentenyl]-2-methyl-1,3-dioxane-r-2-carboxylic acid,
5-(5-Acetyl-5-benzoylaminopentyl)-2,2-dimethyl-1,3-dioxane,
2-(7-Acetyl-7-benzoylaminoheptyloxy)-2-methylpropionic acid,
2-[7-Acetyl-7-(p-toluoylamino)heptyloxy]-2-methylpropionic acid,
2-(7-Acetyl-7-benzoylamino-4-heptynyloxy)-2-methylpropionic acid,
2-[7-Acetyl-7-(4-chlorobenzoylamino)heptyloxy]-2-methylpropionic acid,
2-[7-Acetyl-7-(4-fluorobenzoylamino)heptyloxy]-2-methylpropionic acid,
2-[7-Acetyl-7-(4-tert-butylbenzoylamino)heptyloxy)-2-methylpropionic acid,
2-(8-Acetyl-8-benzoylaminooctyloxy)-2-methylpropionic acid,
2-(6-Acetyl-6-benzoylaminohexyloxy)-2-methylpropionic acid,
5-Acetyl-5-benzoylaminopentanoic acid,
6-Acetyl-6-benzoylaminohexanoic acid,
c-5-[5-Acetyl-5-(4-chlorobenzoylamino)pentyl]-2-methyl-1,3-dioxane-r-2-carboxylic acid,
c-5-[6-Acetyl-6-(p-toluoylamino)hexyl]-2-methyl-1,3-dioxane-r-2-carboxylic acid,
5-Acetyl-5-(p-toluoylamino)pentanoic acid,
c-5-[5-Acetyl-5-(3-fluoro-4-methylbenzoylamino)pentyl]-2-methyl-1,3-dioxane-r-2-carboxylic acid,
c-5-[5-Acetyl-5-(4-ethylbenzoylamino)pentyl]-2-methyl-1,3-dioxane-r-2-carboxylic acid and
7-Acetyl-7-(benzoylamino)-(E)-4-heptenoic acid.

REFERENCE EXAMPLE 23

Methyl c-5-[5-Acetyl-5-(p-toluoylamino)pentyl]-2-methyl-1,3-dioxane-r-2-carboxylate c-5-[5-Acetyl-5-(p-toluoylamino)pentyl]-2-methyl-1,3-dioxane-r-2-carboxylic acid (2.1 g) was dissolved in 44 ml of benzene and 4.2 ml of methanol, and 4.2 ml of 2.0 M trimethylsilyldiazomethane/hexane solution was added dropwise with stirring under ice-cooling. The mixture was stirred for 1 hour, and concentrated. The residue was purified by silica gel column chromatography (Wakogel® C-200, n-hexane: ethyl acetate=2.5:1) to provide 0.85 g of the objective compound as yellowish oil.

$^1$H-NMR (CDCl$_3$) δ: 0.90–1.08 (2H, m), 1.10–1.40 (4H, m), 1.50 (3H, s), 1.55–1.80 (1H, m), 1.85–2.16 (2H, m), 2.27 (3H, s), 2.40 (3H, s), 3.36 (2H, dd), 3.82 (3H, s), 3.92 (2H, dd), 4.80–4.89 (1H, m), 6.89 (1H, d), 7.25 (2H, d), 7.70 (2H, d).

The following compounds were prepared by the same procedure as described in Reference Example 23.

Methyl c-5-(4-acetyl-4-benzoylaminobutyl)-2-methyl-1,3-dioxane-r-2-carboxylate,
Methyl c-5-(5-acetyl-5-benzoylaminopentyl)-2-methyl-1,3-dioxane-r-2-carboxylate,
Methyl c-5-(6-acetyl-6-benzoylaminohexyl)-2-methyl-1,3-dioxane-r-2-carboxylate,
Methyl c-5-[5-acetyl-5-(4-fluorobenzoylamino)pentyl]-2-methyl-1,3-dioxane-r-2-carboxylate,
Methyl c-5-[5-acetyl-5-(4-trifluoromethylbenzoylamino)pentyl]-2-methyl-1,3-dioxane-r-2-carboxylate, Methyl c-5-[5-acetyl-5-(4-tert-butylbenzoylamino)-
pentyl]-2-methyl-1,3-dioxane-r-2-carboxylate and Methyl c-5-[5-acetyl-5-benzoylamino-(E)-2-pentenyl]-2-
methyl-1,3-dioxane-r-2-carboxylate.

REFERENCE EXAMPLE 24

Methyl c-5-[5-acetyl-5-(p-toluoylamino)pentyl]-2-
methyl-1,3-dioxane-r-2-carboxylate c-5-[5-Acetyl-5-(p-toluoylamino)pentyl]-2-methyl-1,3-dioxane-r-2-carboxylic acid (20 g) was dissolved in 140 ml of acetonitrile, and 14.5 g of methyl iodide and 14.1 g of potassium carbonate were added. The mixture was heated to reflux for 3 hours. The reaction solution was cooled, poured into ice-cold water, extracted with ethyl acetate, washed with brine, dried over anhydrous magnesium sulfate and concentrated. The residue was purified by silica gel column chromatography (Wakogel® C-200, n-hexane: ethyl acetate=2:1) to provide 10.3 g of the objective compound as yellowish oil.

The following compounds were prepared by the same procedure as described in Reference Example 24.

Methyl c-5-(5-acetyl-5-benzoylaminopentyl)-2-methyl-1,
3-dioxane-r-2-carboxylate, Methyl c-5-[5-acetyl-5-(4-chlorobenzoylamino)pentyl]-
2-methyl-1,3-dioxane-r-2-carboxylate, Methyl c-5-[6-acetyl-6-(p-toluoylamino)hexyl]-2-
methyl-1,3-dioxane-r-2-carboxylate, Methyl c-5-[5-acetyl-5-(3-fluoro-4-methylbenzoyl-
amino)pentyl]-2-methyl-1,3-dioxane-r-2-carboxylate
and Methyl c-5-[5-acetyl-5-(4-ethylbenzoylamino)pentyl]-2-
methyl-1,3-dioxane-r-2-carboxylate.

REFERENCE EXAMPLE 25

Methyl 6-acetyl-6-benzoylaminohexanoate

6-Acetyl-6-benzoylaminohexanoic acid (4.35 g) was dissolved in 100 ml of methanol, and 0.5 ml of conc. sulfuric acid was added. The mixture was heated to reflux for 2.5 hours. The reaction solution was cooled, poured into ice-cold water, extracted with ethyl acetate, washed with brine, dried over anhydrous magnesium sulfate and concentrated to provide 4.4 g of the objective compound as yellowish crystals. M.p. 59–60° C.

The following compounds were prepared by the same procedure as described in Reference Example 25.

Methyl 2-(7-acetyl-7-benzoylaminoheptyloxy)-2-
methylpropionate,

Methyl 2-[7-acetyl-7-(p-toluoylamino)heptyloxy]-2-
methyl-propionate,

Methyl 2-(7-acetyl-7-benzoylamino-4-heptynyloxy)-2-
methylpropionate,

Methyl 2-[7-acetyl-7-(4-chlorobenzoylamino)
heptyloxy]-2-methylpropionate,

Methyl 2-[7-acetyl-7-(4-fluorobenzoylamino)heptyloxy]-
2-methylpropionate,

Methyl 2-[7-acetyl-7-(4-tert-butylbenzoylamino)
heptyloxy]-2-methylpropionate,

Methyl 2-(8-acetyl-8-benzoylaminooctyloxy)-2-
methylpropionate,

Methyl 2-(6-acetyl-6-benzoylaminohexyloxy)-2-
methylpropionate,

Methyl 5-acetyl5-benzoylaminopentanoate

Methyl 5-acetyl-5-(p-toluoylamino)pentanoate and

Methyl 7-acetyl-7-(benzoylamino)-(E)-4-heptenoate.

REFERENCE EXAMPLE 26

Diethyl (3-bromobenzyl)malonate

Sodium hydride (60%, 1.6 g) was suspended into 20 ml of dry tetrahydrofuran/15 ml of dry N,N-dimethyl formamide, and 7.6 ml of diethyl malonate was added dropwise under ice-cooling. The mixture was stirred for 15 minutes. A solution of 5 g of 3-bromobenzyl bromide/10 ml of dry tetrahydrofuran was then added, and stirred for 1 hour under ice-cooling. To the reaction solution was added ice-cold water, and extracted with ether, washed with brine, dried over anhydrous magnesium sulfate and concentrated. The residue was purified by silica gel column chromatography (Wakogel® C-200, n-hexane: ethyl acetate=10:1) to provide 5.41 g of the objective compound as colorless oil.

$^1$H-NMR (CDCl$_3$) δ: 1.22 (6H, t), 3.81 (2H, d), 3.61 (1H, t), 4.17 (4H, q), 7.10–7.20 (2H, m), 7.29–7.40 (2H, m).

The following compound was prepared by the same procedure as described in Reference Example 26.

Diethyl (4-bromobenzyl)malonate.

REFERENCE EXAMPLE 27

Diethyl (4-bromphenyl)malonate

Under argon flow, 10.85 g of diethyl carbonate was dissolved in 60 ml of benzene, and 2.75 g of 60% sodium hydride was added and the mixture was heated to reflux. A solution of 5.58 g of ethyl 4-bromophenylacetate/20 ml of benzene was added dropwise to the solution over 1 hour, and the mixture was heated to reflux for 1 hour. After cooling, ice-cold water was added dropwise to the reaction solution slowly. The organic layer was separated, washed with water, dried over anhydrous magnesium sulfate and concentrated. The residue was purified by silica gel column chromatography (Wakogel® C-200, n-hexane: ethyl acetate=10:1) to provide 6.45 g of the objective compound as colorless oil.

$^1$H-NMR (CDCl$_3$) δ: 1.26 (6H, t), 4.21 (4H, q), 4.56 (1H, s), 7.29 (2H, d), 7.50 (2H, d).

The following compound was prepared by the same procedure as described in Reference Example 27.

Diethyl (3-bromophenyl)malonate.

REFERENCE EXAMPLE 28

2-(3-Bromobenzyl)-1,3-propanediol

To an ice-cooled 94 ml of 1.0 M diisobutylalminium hydride toluene solution was added dropwise 5.41 g of diethyl (3-bromobenzyl)malonate at 15° C. or less under argon flow. The mixture was stirred for 30 minutes under ice-cooling, warmed to room temperature and stirred for 2 hours. The reaction solution was ice-cooled, and 21 ml of methanol was added dropwise slowly, then 41 ml of 2 N hydrochloric acid was added dropwise. The mixture was stirred for 20 minutes at room temperature. The reaction solution was filtered to remove insolubles, extracted with ethyl acetate, washed with saturated sodium hydrogen carbonate, dried over anhydrous magnesium sulfate and concentrated. The residue was purified by silica gel column chromatography (Wakogel® C-200, chloroform: methanol= 10:1) to provide 1.96 g of the objective compound as white crystals. M.p. 61–63° C.

The following compounds were prepared by the same procedure as described in Reference Example 28.

2-(4-Bromobenzyl)-1,3-propanediol, 2-(4-Bromophenyl)-1,3-propanediol and 2-(3-Bromophenyl)-1,3-propanediol.

REFERENCE EXAMPLE 29

5-(3-Bromobenzyl)-2,2-dimethyl-1,3-dioxane 2-(3-Bromobenzyl)-1,3-propanediol (1.85 g) was dissolved in a mixture of 8 ml of acetone/18 ml of benzene, and 70 mg of p-toluenesulfonic acid monohydrate was added. The solution was subjected to azeotropic dehydration with Dean-Stark apparatus for 1 hour. After addition of saturated sodium hydrogen carbonate solution, the mixture was extracted with ethyl acetate, dried over anhydrous magnesium sulfate and concentrated. The residue was purified by silica gel column chromatography (Wakogel® C-200, n-hexane: ethyl acetate=4:1) to provide 1.47 g of the objective compound as colorless oil.

$^1$H-NMR (CDCl$_3$) δ: 1.43 (6H, d), 1.90–2.10 (1H, m), 2.60 (2H, d), 3.61 (2H, dd), 3.86 (2H, dd), 7.05–7.20 (2H, m), 7.30–7.40 (2H, m).

The following compounds were prepared by the same procedure as described in Reference Example 29.

5-(4-Bromobenzyl)-2,2-dimethyl-1,3-dioxane, 5-(4-Bromophenyl)-2,2-dimethyl-1,3-dioxane and 5-(3-Bromophenyl)-2,2-dimethyl-1,3-dioxane.

REFERENCE EXAMPLE 30

2,2-Dimethyl-5-{3-[(5-methyl-2-phenyloxazol-4-yl)methyl]benzyl}-1,3-dioxane

Under argon flow, 1.45 g of 5-(3-bromobenzyl)-2,2-dimethyl-1,3-dioxane was dissolved in 7 ml of dry tetrahydrofuran, and cooled with the dry ice-acetone bath. To the mixture was added 0.9 ml of N,N,N',N'-tetramethylethylenediamine, and then n-butyllithium (1.6 M hexane solution) was added dropwise at −60° C. or less. After 10-minute-stirring, a suspension of 1.03 g of tri-n-butylphosphine and 0.97 g of copper iodide/7 ml of dry tetrahydrofuran was added and the mixture was stirred for 10 minutes. A solution of 1.52 g of 4-iodomethyl-5-methyl-2-phenyloxazole/7 ml of dry tetrahydrofuran was added dropwise at −60° C. or less, and the mixture was stirred for 15 minutes under the same conditions. The bath was removed and the mixture was stirred for 1.5 hours. To the reaction solution was added saturated aqueous ammonium chloride solution. The mixture was diluted with water, extracted with ether, filtrated to remove insolubles, washed with water, dried over anhydrous magnesium sulfate and concentrated. The residue was purified by silica gel column chromatography (Wakogel® C-200, n-hexane: ethyl acetate=4:1) to provide 0.34 g of the objective compound as white crystals. M.p. 85–87° C.

The following compounds were prepared by the same procedure as described in Reference Example 30.

2,2-Dimethyl-5-{4-[(5-methyl-2-phenyloxazol-4-yl)methyl]benzyl}-1,3-dioxane, 2,2-Dimethyl-5-{4-[(5-methyl-2-phenyloxazol-4-yl)methyl]phenyl}-1,3-dioxane and 2,2-Dimethyl-5-{3-[(5-methyl-2-phenyloxazol-4-yl)methyl]phenyl}-1,3-dioxane.

REFERENCE EXAMPLE 31

5-(5-Methyl-2-phenyloxazol-4-yl)-1-pentanol

To 17 ml of dry ether, 550 mg of lithium aluminum hydride was added and 3.3 g of methyl 5-(5-methyl-2-phenyloxazol-4-yl)-1-pentanoate/10 ml of dry ether was added dropwise. After 1-hour-stirring at room temperature, the mixture was cooled with ice-cold water and 12 ml of tetrahydrofuran/0.7 ml of water was added dropwise gradually. Then, 0.7 ml of 1N sodium hydroxide and 2.5 ml of water were added and stirred for 15 minutes. The mixture was filtrated to remove insolubles and the filtrate was concentrated to provide 2.9 g of the objective compound as yellowish crystals. M.p. 40–42° C.

The following compounds were prepared by the same procedure as described in Reference Example 31.

4-(5-Methyl-2-phenyloxazol-4-yl)-1-butanol,

4-[5-Methyl-2-(p-tolyl)oxazol-4-yl]-1-butanol,

4-[2-(p-Tolyl)-5-trifluoromethyloxazol-4-yl]-1-butanol,

6-[5-Methyl-2-(p-tolyl)oxazol-4-yl]-1-hexanol and 6-(5-Methyl-2-phenyloxazol-4-yl)-(E)-4-hexen-1-ol.

REFERENCE EXAMPLE 32

4-(5-Bromopentyl)-5-methyl-2-phenyloxazole 5-(5-Methyl-2-phenyloxazol-4-yl)-1-pentanol (2.9 g) was dissolved in 62 ml of dry ether, and 8.4 g of carbon tetrabromide was added. To the mixture was added gradually 6.6 g of triphenylphosphine under ice-cooling. The mixture was then stirred for 2.5 hours at room temperature, filtrated to remove insolubles and the filtrate was concentrated. The residue was purified by silica gel column chromatography (Wakogel® C-200, n-hexane: ethyl acetate=10:1) to provide 2.61 g of the objective compound as yellowish oil.

The following compounds were prepared by the same procedure as described in Reference Example 32.

4-(4-Bromobutyl)-5-methyl-2-phenyloxazole,

Ethyl 2-(6-bromo-4-hexynyloxy)-2-methylpropionate, 4-(4-Bromobutyl)-5-methyl-2-(p-tolyl)oxazole, 4-(4-Bromobutyl)-2-(p-tolyl)-5-trifluoromethyloxazole, 4-(6-Bromohexyl)-5-methyl-2-(p-tolyl)oxazole and 4-[6-Bromo-(E)-2-hexenyl]-5-methyl-2-phenyloxazole.

REFERENCE EXAMPLE 33

Diethyl [5-(5-methyl-2-phenyloxazol-4-yl)pentyl]malonate

To 35 ml of dry tetrahydrofuran, 650 mg of 60% sodium hydride was added, and 3.9 g of diethyl malonate was added dropwise with stirring under ice-cooling. After the stirring was continued for 10 minutes, 4-(4-bromopentyl)-5-methyl-2-phenyloxazol (2.5 g) was added. The mixture was stirred for 10 minutes at room temperature and then heated to reflux for 12 hours. The reaction solution was poured into ice-cold water, neutralized with dilute hydrochloric acid and then extracted with ethyl acetate. The organic layer was washed with brine, dried over anhydrous magnesium sulfate and concentrated. The residue was purified by silica gel column chromatography (Wakogel® C-200, n-hexane: ethyl acetate=10:1) to provide 2.75 g of the objective compound as colorless oil.

$^1$H-NMR (CDCl$_3$) δ: 1.26 (6H, t), 1.32–1.43 (4H, m), 1.55–1.75 (2H, m), 1.82–2.00 (2H, m), 2.31 (3H, s), 2.47 (2H, t), 3.31 (1H, t), 4.19 (4H, q), 7.37–7.47 (3H, m), 7.95–8.00 (2H, m).

The following compounds were prepared by the same procedure as described in Reference Example 33.

Diethyl [4-(5-Methyl-2-phenyloxazol-4-yl)butyl]malonate,

Diethyl {4-[5-methyl-2-(p-tolyl)oxazol-4-yl]butyl}malonate,

Diethyl {4-[2-(p-tolyl)-5-trifluoromethyloxazol-4-yl]butyl}malonate and

Diethyl [5-(benzoylamino)-5,5-bis(ethoxycarbonyl)-(E)-2-pentenyl]malonate.

REFERENCE EXAMPLE 34

4-[6,6-Bis(hydroxymethyl)hexyl]-5-methyl-2-phenyloxazole

To 15 ml of dry ether, 637 mg of lithium aluminium hydride was added, and 2.6 g of diethyl [5-(5-methyl-2-phenyloxazol-4-yl)pentyl]malonate/10 ml of dry ether was added dropwise. After 2-hour-stirring at room temperature, the mixture was cooled with ice-cold water, and 14 ml of tetrahydrofuran/0.8 ml of water was added dropwise gradually. To the mixture were added 0.8 ml of an aqueous solution of 1 N sodium hydroxide and 2.3 ml of water, and stirred for 15 minutes and filtrated to remove insolubles. The filtrate was concentrated to provide 2.0 g of the objective compound as white crystals. M.p. 71–74° C.

The following compounds were prepared by the same procedure as described in Reference Example 34.

4-[5,5-Bis(hydroxymethyl)pentyl]-5-methyl-2-phenyloxazole,

4-[5,5-Bis(hydroxymethyl)pentyl]-5-methyl-2-(p-tolyl)oxazole,

4-[5,5-Bis(hydroxymethyl)pentyl]-2-(p-tolyl)-5-trifluoromethyloxazole and

4-[5,5-Bis(hydroxymethyl)pentyl]-5-ethyl-2-(p-tolyl)oxazole.

REFERENCE EXAMPLE 35

4-{3-[2,2-Bis(hydroxymethyl)ethyl]benzyl}-5-methyl-2-phenyloxazole

A mixture solution of 320 mg of 2,2-dimethyl-5-{3-[(5-methyl-2-phenyloxazol-4-yl)methyl]benzyl}-1,3-dioxane, 21 ml of ethanol and 21 mg of pyridinium p-toluenesulfonate (PPTS) was stirred for 2 hours at 55–60° C. The reaction solution was concentrated and the residue was purified by silica gel column chromatography (Wakogel® C-200, chloroform) to provide 305 mg of the objective compound as colorless oil.

$^1$H-NMR (CDCl$_3$) δ: 1.90–2.15 (1H, m), 2.29 (3H, s), 2.35 (2H, br), 2.60 (2H, d), 3.64 (2H, dd), 3.78 (2H, dd), 3.85 (2H, s), 6.90–7.50 (7H, m), 7.85–8.05 (2H, m).

The following compounds were prepared by the same procedure as described in Reference Example 35.

4-{4-[2,2-Bis(hydroxymethyl)ethyl]benzyl}-5-methyl-2-phenyloxazole,

4-{4-[1,1-Bis(hydroxymethyl)methyl]benzyl}-5-methyl-2-phenyloxazole,

4-{3-[1,1-Bis(hydroxymethyl)methyl]benzyl}-5-methyl-2-phenyloxazole and

4-[5,5-Bis(hydroxymethyl)pentyl]-5-methyl-2-phenyloxazole.

REFERENCE EXAMPLE 36

Methyl 5-(5-methyl-2-phenyloxazol-4-yl)pentanoate

Methyl 6-acetyl-6-benzoylaminohexanoate (4.35 g) was dissolved in 87 ml of toluene, and 2.9 ml of phosphorus oxychloride was added and heated to reflux for 50 minutes. The reaction solution was cooled, poured into ice-cold water, neutralized with aqueous sodium hydrogen carbonate solution, extracted with ethyl acetate and washed with brine. The resulting solution was dried over anhydrous magnesium sulfate and concentrated to provide 3.40 g of the objective compound as yellowish oil.

The following compounds were prepared by the same procedure as described in Reference Example 36.

Methyl 4-(5-methyl-2-phenyloxazol-4-yl)butanoate,

Methyl 4-[5-methyl-2-(p-tolyl)oxazol-4-yl] butanoate,

Ethyl 6-[5-methyl-2-(p-tolyl)oxazol-4-yl]hexanoate and

Methyl 6-(5-methyl-2-phenyloxazol-4-yl)-(E)-4-hexenoate.

REFERENCE EXAMPLE 37

1-Bromo-3-[2,2-bis(ethoxycarbonyl)-2-(p-toluoylamino)-ethyl]benzene

To 100 ml of dry ethanol, 21.45 g of 20% sodium ethoxide-ethanol solution and 17.61 g of diethyl p-toluoylaminomalonate were added and stirred for 30 minutes at room temperature under argon atmosphere. After 15.00 g of 3-bromobenzyl bromide was added dropwise, the reaction solution was stirred for 8 hours at 55° C. and then concentrated. To the residue was added water, and extracted with ethyl acetate. The organic layer was washed with brine and dried over anhydrous magnesium sulfate. The solvent was distilled off under reduced pressure to provide 29.82 g of the objective compound as yellow oil.

$^1$H-NMR (CDCl$_3$) δ: 1.31 (6H, t), 2.41 (3H, s), 3.74 (2H, s), 4.30 (4H, q), 6.90–7.40 (7H, m), 7.60–7.70 (2H, m).

REFERENCE EXAMPLE 38

1-Bromo-3-[2-carboxy-2-(p-toluoylamino)ethyl]benzene

1-Bromo-3-[2,2-bis(ethoxycarbonyl)-2-(p-toluoylamino)-ethyl]benzene (28.93 g) was dissolved in 200 ml of ethanol, and a solution of 9.6 g of sodium hydroxide/60 ml of water was added and heated to reflux for 3 hours. The reaction solution was concentrated. To the residue was added water, and washed with diethyl ether. The aqueous layer was acidified with hydrochloric acid, extracted with ethyl acetate. The organic layer was dried over anhydrous magnesium sulfate and concentrated to provide 24.19 g of the objective compound as colorless oil. The resulting oil was dissolved in 150 ml of ethyl acetate and, after addition of 150 ml of xylene, stirred for 15 hours at 130° C. The solvent was distilled off under reduced pressure, and the resulting crystals were washed with diethyl ether to provide 17.22 g of the objective compound as colorless crystals. M.p. 196–197° C.

REFERENCE EXAMPLE 39

1-[2-Acetyl-2-(p-toluoylamino)ethyl]-3-bromobenzene

1-Bromo-3-[2-carboxy-2-(p-toluoylamino)ethyl]benzene (16.84 g) was dissolved in 85 ml of pyridine, and 55 ml of acetic anhydride was added and stirred for 3 hours under argon atmosphere at 90–95° C. Water (55 ml) was added dropwise gradually so that the maximum temperature did not exceed 100° C., and the mixture was stirred for 20 minutes at 60–70° C. The reaction solution was cooled, poured into ice-cold water and extracted with ethyl acetate. The resulting solution was washed with 10% hydrochloric acid, water and saturated aqueous sodium hydrogen carbonate solution sequentially and dried over anhydrous magnesium sulfate. The solvent was distilled off under reduced pressure. The resulting crystals were washed with isopropyl ether to provide 13.31 g of the objective compound as brownish crystals. M.p. 106–107° C.

REFERENCE EXAMPLE 40

1-Bromo-3-{[5-methyl-2-(p-tolyl)oxazol-4-yl]methyl}-benzene

1-[2-Acetyl-2-(p-toluoylamino)ethyl]-3-bromobenzene (13.26 g) was dissolved in 260 ml of toluene, and 6.8 ml of phosphorus oxychloride was added and heated to reflux for 3 hours. The reaction solution was cooled, poured into ice-cold water and extracted with ethyl acetate. The resulting solution was washed with aqueous solution of saturated sodium hydrogen carbonate, dried over anhydrous magnesium sulfate and concentrated. The residue was purified by silica gel column chromatography (Wakogel® C-200, n-hexane: ethyl acetate=4:1) to provide 10.86 g of the objective compound as yellowish crystals. M.p. 74–75° C.

REFERENCE EXAMPLE 41

3-{[5-Methyl-2-(p-tolyl)oxazol-4-yl]methyl}-benzaldehyde

N,N-Dimethylformamide (30 ml) was added to 9.48 g of 1-bromo-3-{[5-methyl-2-(p-tolyl)oxazol-4-yl]methyl}benzene, 2.83 g of sodium formate and 0.97 g of bis(triphenylphosphine)palladium (II) dichloride, and the mixture was stirred for 9 hours at 110° C. under bubbling carbon monoxide. To the reaction solution was added water, and extracted with ethyl acetate, filtered to remove insolubles, dried over anhydrous magnesium sulfate and concentrated. The residue was purified by silica gel column chromatography (Wakogel® C-200, n-hexane: ethyl acetate=4:1) to provide 3.58 g of the objective compound as colorless crystals. M.p. 98–99° C.

REFERENCE EXAMPLE 42

3-{[5-Methyl-2-(p-tolyl)oxazol-4-yl]methyl}benzyl-alcohol

3-{[5-Methyl-2-(p-tolyl)oxazol-4-yl]methyl}-benzaldehyde (3.54 g) was suspended into 35 ml of methanol, and 230 mg of sodium borohydride was added thereto with stirring under ice-cooling, and stirred for 1.5 hours at room temperature. The reaction solution was poured into ice-cold water, extracted with ethyl acetate, washed with water and dried over anhydrous magnesium sulfate. The solvent was distilled off under reduce pressure to provide 3.54 g of the objective compound as colorless crystals. M.p. 97–99° C.

REFERENCE EXAMPLE 43

3-{[5-methyl-2-(p-tolyl)oxazol-4-yl]methyl}benzyl-bromide

3-{[5-Methyl-2-(p-tolyl)oxazol-4-yl]methyl}-benzyl alcohol (3.52 g) was dissolved in 60 ml of dichloromethane. After addition of 3.77 g of triphenylphosphine and 5.17 g of carbon tetrabromide, the mixture was stirred for 30 minutes at room temperature. The reaction solution was concentrated and the residue was purified by silica gel column chromatography (Wakogel® C-200, n-hexane: ethyl acetate=4:1) to provide 3.96 g of the objective compound as colorless crystals. M.p. 101–102° C.

REFERENCE EXAMPLE 44

Diethyl 3-{[5-methyl-2-(p-tolyl)oxazol-4-yl]methyl}-benzylmalonate

To 15 ml of dry tetrahydrofuran and 7 ml of dry N,N-dimethylformamide, 0.88 g of 60% sodium hydride was added. To the mixture was added dropwise 4.40 g of diethyl malonate with stirring under ice-cooling. After 15-minute-stirring, a solution of 3.93 g of 3-{[5-methyl-2-(p-tolyl)oxazol-4-yl]methyl}benzyl bromide/5 ml of dry tetrahydrofuran was added and stirred for 1 hour under ice-cooling. The reaction solution was poured into ice-cold water, extracted with ethyl acetate, washed with water and dried over anhydrous magnesium sulfate. The solvent was distilled off under reduced pressure and the residue was purified by silica gel column chromatography (Wakogel® C-200, n-hexane: ethyl acetate=5:1) to provide 3.95 g of the objective compound as colorless crystals.

$^1$H-NMR (CDCl$_3$) δ: 1.17 (6H, t), 2.25 (3H, s), 2.38 (3H, s), 3.18 (2H, d), 3.62 (1H, t), 4.07 (2H, s), 4.12 (4H, q), 7.00–7.30 (6H, m), 7.80–7.90 (2H, m).

REFERENCE EXAMPLE 45

2-[3-{[5-Methyl-2-(p-tolyl)oxazol-4-yl]methyl}benzyl]-1,3-propanediol

To 30 ml of dry tetrahydrofuran, 854 mg of lithium aluminium hydride was added, and 3.94 g of diethyl 3-{[5-methyl-2-(p-tolyl)oxazol-4-yl]methyl}benzylmalonate/10 ml of dry tetrahydrofuran was added dropwise with stirring under ice-cooling. The mixture was stirred for 1.5 hours at room temperature and cooled with ice-cold water. To the mixture were added dropwise 0.85 ml of water, 0.85 ml of 15% sodium hydroxide solution and 2.5 ml of water sequentially, and stirred for 15 minutes. The mixture was filtrated to remove insolubles, and the filtrate was concentrated. The residue was dissolved into ethyl acetate and dried over anhydrous magnesium sulfate. The solvent was distilled off under reduced pressure and the residue was purified by silica gel column chromatography (Wakogel® C-200, chloroform: methanol=20:1) to provide 2.32 g of the objective compound as colorless crystals. M.p. 114–115C.

REFERENCE EXAMPLE 46

Diethyl (3-fluoro-4-methylbenzoyl)aminomalonate

To a solution of 10.1 g of 3-fluoro-4-methylbenzoic acid and 15.2 g of diethyl aminomalonate hydrochloride in 200 ml of N,N-dimethylformamide, 9.7 g of 1-hydroxybenzotriazole, 23 ml of triethylamine and 13.8 g of 1-(3-dimethylaminopropyl)-3-ethylcarbodiimide hydrochloride were added sequentially, and stirred for 1 hour at room temperature. After addition of water to the reaction solution, the mixture was extracted with ethyl acetate. The extract was washed with water, 10% hydrochloric acid, water, saturated aqueous sodium hydrogen carbonate solution sequentially and dried over anhydrous magnesium sulfate. The solvent was distilled off under reduced pressure and the residue was crystallized by addition of isopropyl ether to provide 15.1 g of the objective compound as colorless crystals. M.p. 102–103° C.

REFERENCE EXAMPLE 47

1-(p-Toluenesulfonyloxy)-3-[2-(p-tolyl)-5-trifluoromethyloxazol-4-yl]propane

3-[2-(p-Tolyl)-5-trifluoromethyloxazol-4-yl]-1-propanol (6.40 g) synthesized according to the method of Kawase et. al. (Chem. Pharm. Bull., 46, 749–756(1998)) was dissolved in 35 ml of dichloromethane. To the solution were added sequentially 293 mg of 4-(dimethylamino)pyridine, 4.7 ml of triethylamine and 5.13 g of p-toluenesulfonyl chloride, and stirred for 3 hours at room temperature. To the reaction solution was added ethyl acetate, and washed with water, 10% hydrochloric acid and an aqueous solution of saturated aqueous sodium hydrogen carbonate solution sequentially, and dried over anhydrous magnesium sulfate. The solvent was distilled off under reduced pressure to provide 10.08 g of the objective compound as pale brown crystals. M.p. 57–58° C.

REFERENCE EXAMPLE 48

4-[2-(p-Tolyl)-5-trifluoromethyloxazol-4-yl]-butanenitrile

To 40 ml of dimethylsulfoxide, 10.08 g of 1-(p-toluenesulfonyloxy)-3-[2-(p-tolyl)-5-trifluoromethyloxazol-4-yl]propane, 1.16 g of sodium cyanide was added and stirred for 2 hours at 90° C. Water was added to the reaction solution and the mixture was extracted with diethyl ether, washed with water and dried over anhydrous magnesium sulfate. The solvent was distilled off under reduced pressure to provide 6.35 g of the objective compound as pale brown crystals. M.p. 41–42.5° C.

REFERENCE EXAMPLE 49

Methyl 4-[2-(p-tolyl)-5-trifluoromethyloxazol-4-yl]butanoate

4-[2-(p-Tolyl)-5-trifluoromethyloxazol-4-yl]butanenitrile (5.28 g) was dissolved in 40 ml of methanol, and stirred for 10 minutes under ice-cooling under bubbling hydrogen chloride gas. After the bubbling was stopped, the mixture was warmed to room temperature and stirred for 30 minutes. To the reaction solution was added 5 ml of water, and the mixture was stirred for 30 minutes, allowed to stand at room temperature overnight. After addition of water, the reaction solution was extracted with ethyl acetate. The extract was washed with saturated aqueous sodium hydrogen carbonate solution, dried over anhydrous magnesium sulfate and concentrated. The residue was purified by silica gel column chromatography (Wakogel® C-200, n-hexane: ethyl acetate=4:1) to provide 5.63 g of the objective compound as colorless crystals. M.p. 44.5–45° C.

REFERENCE EXAMPLE 50

Methyl 4-(fluoromethyl)benzoate Dry acetonitrile (150 ml) was added to 25.00 g of methyl 4-(bromomethyl)benzoate, 19.02 g of potassium fluoride and 9.51 g of calcium fluoride, and the mixture was heated to reflux for 3 days. The reaction solution was concentrated. After addition of 200 ml of acetonitrile, insolubles were removed by filtration, and the filtrate was concentrated again. The residue was purified by silica gel column chromatography (YMC.GEL® SIL-60-230/70, n-hexane: ethyl acetate= 10:1–4:1), followed by distillation under reduced pressure to provide 14.45 g of the objective compound as colorless oil. B.p. 118.5–119° C./18 mmHg.

$^1$H-NMR (CDCl$_3$) δ: 3.93 (3H, s), 5.44 (2H, d), 7.40–7.46 (2H, m), 8.03–8.09 (2H, m).

REFERENCE EXAMPLE 51

4-(Fluoromethyl)benzoic Acid

To 200 ml of methanol, 8.68 g of methyl 4-(fluoromethyl)benzoate was dissolved, and 77 ml of aqueous solution of 1 N sodium hydroxide was added dropwise with stirring and cooling. The mixture was then stirred for 3.5 hours at room temperature. After the mixture was acidified with 1 N hydrochloric acid, the precipitated crystals were collected by filtration, and the filtrate was concentrated. The precipitated crystals were combined with the residue obtained by concentrating the filtrate, and water was added thereto. The mixture was extracted with ethyl acetate and dried over anhydrous magnesium sulfate. The solvent was distilled off under reduced pressure to provide 7.47 g of the objective compound as colorless crystals.

M.p. 192–194° C.

REFERENCE EXAMPLE 52

4-(Fluoromethyl)benzoyl Chloride 4-(Fluoromethyl)benzoic acid (6.20 g) was dissolved in 30 ml of benzene, and 0.3 ml of N,N-dimethylformamide was added and then 4.4 ml of thionyl chloride was added dropwise. The mixture was stirred for 1 hour at 40° C. and then heated to reflux for another 1 hour. The solvent was distilled off under reduced pressure to provide 6.70 g of the objective compound as pale yellow oil.

REFERENCE EXAMPLE 53

Ethyl 6-chloro-2-ethoxycarbonyl-2-(p-toluoylamino)-hexanoate

Sodium (6.42 g) was dissolved in 390 ml of ethanol at room temperature. To the solution was added 78.0 g of diethyl p-toluoylaminomalonate, and 47.9 g of 1-bromo-4-chlorobutane was added dropwise under heating to reflux. The mixture was heated to reflux for 20 hours. The reaction solution was concentrated. To the residue was added water, and the mixture was washed with ethyl acetate. After washing with 10% hydrochloric acid and water sequentially, the solution was dried over anhydrous magnesium sulfate and concentrated. The residue was purified by silica gel column chromatography (Wakogel® C-200, n-hexane: ethyl acetate=9:1) to provide 55.7 g of the objective compound as colorless oil.

$^1$H-NMR (CDCl$_3$) δ: 1.26 (6H, t), 1.26–1.42 (2H, m), 1.72–1.86 (2H, m), 2.41 (3H, s), 2.44–2.52 (2H, m), 3.51 (2H, t), 4.28 (4H, q), 7.24–7.28 (2H, m), 7.48 (1H, s), 7.71–7.75 (2H, m).

REFERENCE EXAMPLE 54

6-Chloro-2-(p-toluoylamino)hexanoic Acid

Ethyl 6-chloro-2-ethoxycarbonyl-2-(p-toluoylamino)-hexanoate (103.2 g) was dissolved in 412 ml of ethanol, and a solution of 24.5 g of sodium hydroxide/98 ml of water was added, and heated to reflux for 16 hours. The reaction solution was concentrated. To the residue was added ethyl acetate. The mixture was acidified with hydrochloric acid and extracted with ethyl acetate. The extract was washed with water, dried over anhydrous magnesium sulfate and concentrated to provide 80.0 g of colorless gum. To the resulting gum, 75 ml of acetic acid was added and heated to reflux for 10 hours. After the mixture was stirred and stood to cool, the precipitated crystals were washed with ethyl acetate and recrystallized from acetic acid to provide 26.0 g of the objective compound as colorless crystals. M.p. 177–181° C.

REFERENCE EXAMPLE 55

8-Chloro-4-(p-toluoylamino)-3-octanone

6-Chloro-2-(p-toluoylamino)hexanoic acid (10.0 g) was dissolved in 15 ml of dry pyridine, and 15 ml of propionic anhydride was added and stirred for 2.5 hours at 90° C. To the mixture was added 15 ml of water slowly so that the maximum temperature did not exceed 85° C., and stirred for 20 minutes at 80° C. The reaction solution was cooled, poured into ice-cold water and extracted with diethyl ether. The extract was washed with 10% hydrochloric acid, an aqueous solution of saturated sodium hydrogen carbonate and brine sequentially, dried over anhydrous magnesium sulfate and concentrated. The residue was purified by silica gel column chromatography (Wakogel® C-200, n-hexane: ethyl acetate=8:1–4:1) to provide 6.0 g of the objective compound as colorless crystals. M.p. 85–86° C.

REFERENCE EXAMPLE 56

4-(4-Chlorobutyl)-5-ethyl-2-(p-tolyl)oxazole

To 150 ml of toluene, 6.5 g of 8-chloro-4-(p-toluoylamino)-3-octanone was dissolved, and 4.1 ml of phosphorus oxychloride was added and heated to reflux for 1.5 hours. The reaction solution was cooled, poured into ice-cold water and extracted with ethyl acetate. The extract was washed with an aqueous solution of saturated sodium hydrogen carbonate and brine sequentially, dried over anhydrous magnesium sulfate and concentrated. The residue was purified by silica gel column chromatography (Wakogel® C-200, n-hexane: ethyl acetate-8:1) to provide 5.5 g of the objective compound as yellowish crystals.

$^1$H-NMR (CDCl$_3$) δ: 1.27 (3H, t), 1.78–1.87 (4H, m), 2.38 (3H, s), 2.52 (2H, t), 2.67 (2H, q), 3.57 (2H, t), 7.23 (2H, d), 7.84–7.89 (2H, m).

REFERENCE EXAMPLE 57

Diethyl 4-[5-ethyl-2-(p-tolyl)oxazol-4-yl]butyl Malonate

To 32.8 ml of 21% sodium ethoxide-ethanol solution, 16.7 ml of diethyl malonate was added under heating to reflux. Then, 5.0 g of 4-(4-chlorobutyl)-5-ethyl-2-(p-tolyl)oxazole/5 ml of ethanol was added dropwise and the mixture was heated to reflux for 7 hours under argon atmosphere. The reaction solution was poured into ice-cold water and extracted with ethyl acetate, dried over anhydrous magnesium sulfate and concentrated. The residue was purified by silica gel column chromatography (Wakogel® C-200, n-hexane: ethyl acetate=10:1) to provide 2.65 g of the objective compound as yellow oil.

$^1$H-NMR (CDCl$_3$) δ: 1.25 (6H, t), 1.29 (3H, t), 1.35–1.46 (2H, m), 1.65–1.73 (2H, m), 1.88–1.99 (2H, m), 2.39 (3H, s), 2.48 (2H, t), 2.66 (2H, q), 3.32 (1H, t), 4.13–4.26 (4H, m), 7.22 (2H, d), 7.87 (2H, d).

REFERENCE EXAMPLE 58

The following compounds were prepared by the same procedure as described in the after-mentioned Example 6.

2,2-Dimethyl-5-[4-(5-methyl-2-phenyloxazol-4-yl)butyl]-1,3-dioxane,

Methyl 4-(5-methyl-2-phenyloxazol-4-yl)butyrate and

Methyl 3-(5-methyl-2-phenyloxazol-4-yl)propionate.

REFERENCE EXAMPLE 59

1-(o-Toluoylamino)-2-propanol

To 100 ml of a solution of 5.83 g of 1-amino-2-propanol in toluene, 18.0 ml of triethylamine was added, and 10 ml of a solution of 10.00 g of o-toluoyl chloride in toluene was added dropwise slowly with stirring under ice-cooling. After 30-minute-stirring, the ice-bath was removed, and the mixture was stirred for additional 1 hour at room temperature. To the reaction solution was added water, and the mixture was extracted with ethyl acetate. The extract was washed with 10% hydrochloric acid, ice-cold water and saturated aqueous sodium hydrogen carbonate solution sequentially, dried over anhydrous magnesium sulfate and the solvent was distilled off under reduced pressure. The residue was crystallized by addition of diethyl ether to provide 7.25 g of the objective compound as colorless crystals. M.p. 78–81° C.

The following compounds were prepared by the same procedure as described in Reference Example 59.

1-(4-Fluoromethylbenzoylamino)-2-propanol, 1-(m-Toluoylamino)-2-propanol and 1-(Cyclohexylcarbonylamino)-2-propanol.

REFERENCE EXAMPLE 60

1-(o-Toluoylamino)-2-propanone

Pyridinium chlorochromate (15.91 g) was added to 143 ml of a suspension of 7.13 g of 1-(o-toluoylamino)-2-propanol and 15.91 g of celite in dichloromethane with stirring. The mixture was stirred for 4 hours at room temperature. The reaction solution was purified by silica gel column chromatography (Wakogel® C-200, chloroform) and the solvent was distilled off under reduced pressure. The eluate was purified again by silica gel column chromatography (Wakogel® C-200, n-hexane: ethyl acetate=1:2) to provide 5.73 g of the objective compound as colorless crystals. M.p. 65–66° C.

The following compounds were prepared by the same procedure as described in Reference Example 60.

1-(2,4-Dimethylbenzoylamino)-2-propanone, 1-(4-Fluoromethylbenzoylamino)-2-propanone, 1-(m-Toluoylamino)-2-propanone, 1-(3,4-Dimethylbenzoylamino)-2-propanone, 1-(4-Methoxybenzoylamino)-2-propanone and 1-(Cyclohexylcarbonylamino)-2-propanone.

REFERENCE EXAMPLE 61

Methyl c-5-[5-acetyl-5-(o-toluoylamino)pentyl]-2-methyl-1,3-dioxane-r-2-carboxylate Under argon atmosphere, 40 ml of a suspension of 1.18 g of 60% sodium hydride in N,N-dimethylformamide was cooled to −25° C. in dry ice-acetone bath, and then 15 ml of a solution of 5.65 g of 1-(o-toluoylamino)-2-propanone in N,N-dimethylformamide was added dropwise slowly. After 1-hour-stirring, 5 ml of a solution of 10.09 g of methyl c-5-(4-iodobutyl)-2-methyl-1,3-dioxane-r-2-carboxylate in N,N-dimethylformamide was added dropwise slowly, and the mixture was stirred for another 1 hour. To the reaction solution was added 1 ml of 1 N hydrochloric acid, and then water, and the mixture was extracted with diethyl ether. The extract was washed with aqueous solution of 0.5% aqueous sodium hydroxide solution, dried over anhydrous magnesium sulfate and the solvent was distilled off under reduced pressure. The residue was purified by silica gel column chromatography (Wakogel® C-200, n-hexane: ethyl acetate=1:1) to provide 6.38 g of the objective compound as colorless oil.

$^1$H-NMR (CDCl$_3$) δ: 1.01–1.08 (2H, m), 1.22–1.39 (4H, m), 1.51 (3H, s), 1.62–1.71 (2H, m), 1.97–2.09 (1H, m), 2.28 (3H, s), 2.44 (3H, s), 3.39 (2H, t), 3.83 (3H, s), 3.94 (2H, dd), 4.84 (1H, q), 6.49 (1H, d), 7.22–7.42 (4H, m).

The following compounds were prepared by the same procedure as described in Reference Example 61.

Methyl c-5-[5-acetyl-5-(2,4-dimethylbenzoylamino)pentyl]-2-methyl-1,3-dioxane-r-2-carboxylate, Methyl c-5-[5-acetyl-5-(4-fluoromethylbenzoylamino)pentyl]-2-methyl-1,3-dioxane-r-2-carboxylate, Methyl c-S-[5-acetyl-5-(m-toluoylamino)pentyl]-2-methyl-1,3-dioxane-r-2-carboxylate, Methyl c-5-[5-acetyl-5-(3,4-dimethylbenzoylamino)pentyl]-2-methyl-1,3-dioxane-r-2-carboxylate, Methyl c-5-[5-acetyl-5-(4-methoxybenzoylamino)pentyl]-2-methyl-1,3-dioxane-r-2-carboxylate, Methyl c-5-[5-acetyl-5-(2-thenoylamino)pentyl]-2-methyl-1,3-dioxane-r-2-carboxylate and Methyl c-5-[5-acetyl-5-(cyclohexylcarbonylamino)pentyl]-2-methyl-1,3-dioxane-r-2-carboxylate.

REFERENCE EXAMPLE 62

1-(3,4-Dimethylbenzoylamino)-2-propanol

To 30 ml of a solution of 5.00 g of 3,4-dimethylbenzoic acid and 2.75 g of 1-amino-2-propanol in N,N-dimethylformamide, 4.95 g of 1-hydroxybenzotriazole, 6.96 ml of triethylamine and 7.02 g of 1-(3-dimethylaminopropyl)-3-ethylcarbodiimide hydrochloride were added sequentially, and stirred for 15 hours at room temperature. After addition of water, the reaction solution was extracted with ethyl acetate, washed with 10% hydrochloric acid, ice-cold water and aqueous solution of saturated sodium hydrogen carbonate sequentially, and dried over anhydrous magnesium sulfate. The solvent was distilled off under reduced pressure to provide 6.28 g of the objective compound as colorless crystals. M.p. 77–78° C.

The following compounds were prepared by the same procedure as described in Reference Example 62.

1-(2,4-Dimethylbenzoylamino)-2-propanol and 1-(4-Methoxybenzoylamino)-2-propanol.

REFERENCE EXAMPLE 63

Methyl 2-(2-thenoylamino)acetate

To 250 ml of a suspension of 12.56 g of methyl 2-aminoacetate hydrochloride in dichloromethane, 20.24 g of triethylamine was added, and stirred for 30 minutes at room temperature. After ice-cooling, 20 ml of a solution of 14.66 g of 2-thenoyl chloride in dichloromethane was added dropwise slowly. The ice-bath was removed and the mixture was stirred for 14 hours at room temperature. The precipitated crystals were collected by filtration and washed with dichloromethane. The solvent was removed from the filtrate by distillation under reduced pressure. To the residue was added t-butyl methyl ether to precipitate. The both products were combined to provide 17.20 g of the objective compound as brownish crystals.

$^1$H-NMR (CDCl$_3$) δ: 3.80 (3H, s), 4.23 (2H, d), 6.62 (1H, br), 7.09 (1H, dd), 7.50 (1H, dd), 7.57 (1H, dd).

REFERENCE EXAMPLE 64

Sodium 2-(2-thenoylamino)acetate

To 200 ml of a solution of 16.70 g of methyl 2-(2-thenoylamino)acetate in methanol, 20 ml of aqueous solution of 4.02 g sodium hydroxide was added, and heated to reflux for 30 minutes. The solvent was distilled off under reduced pressure. The residue was crystallized by addition of isopropanol to provide 18.03 g of the objective compound as pale yellow crystals.

REFERENCE EXAMPLE 65

1-(2-Thenoylamino)-2-propanone

To 44.0 ml of a suspension of 16.70 g of sodium 2-(2-thenoylamino)acetate in β-picoline, 42.7 ml of acetic anhydride was added, and stirred for 3 hours at room temperature. After ice-cooling, 26.3 ml of ethanol, 129.7 ml of water and 45.2 ml of conc. hydrochloric acid were slowly added dropwise in sequence, and the mixture was stirred for 15 minutes as it is. After removal of ice-bath, the mixture was stirred for another 15 minutes at room temperature. Water (250 ml) was added and the precipitated crystals were collected, and washed with water. To the crystals was added 37.0 ml of water, and the mixture was heated to reflux for 1 hour. After 14.0 g of sodium chloride was added, the mixture was heated to reflux for another 1 hour. The reaction solution was extracted with ethyl acetate, and dried over anhydrous magnesium sulfate. After addition of activated carbon (Kyoryoku-sirasagi® MOIWY433), the mixture was stirred for 30 minutes at room temperature. The solvent was distilled off under reduced pressure. The residue was crystallized by addition of t-butyl methyl ether to provide 7.15 g of the objective compound as pale brown crystals.

$^1$H-NMR (CDCl$_3$) δ: 2.27 (3H, s), 4.34 (2H, d), 6.80 (1H, br), 7.09 (1H, dd), 7.50 (1H, dd), 7.57 (1H, dd).

REFERENCE EXAMPLE 66

4-[5,5-Bis(bromomethyl)pentyl]-5-methyl-2-(p-tolyl)-oxazole

To 15 ml of a solution of 2.25 g of 4-[5,5-bis(hydroxymethyl)pentyl]-5-methyl-2-(p-tolyl)oxazole in N,N-dimethylformamide, 3.92 ml of γ-colidine, 2.57 g of lithium bromide and 2.3 ml of methanesulfonyl chloride were added sequentially, and stirred under heating for 2.5 hours at 80° C. To the reaction solution was added water, and the mixture was extracted with ethyl acetate, washed with brine, dried over anhydrous magnesium sulfate and the solvent was distilled off under reduce pressure. The residue was purified by silica gel column chromatography (Wakogel® C-200, n-hexane: ethyl acetate=9:1) to provide 1.45 g of the objective compound as brown oil.

$^1$H-NMR (CDCl$_3$) δ: 1.30–1.55 (2H, m), 1.60–1.85 (4H, m), 1.95–2.15 (1H, m), 2.31 (3H, s), 2.38 (3H, s), 2.49 (2H, t), 2.82–3.05 (4H, m), 7.38–7.45 (2H, m), 7.94–8.01 (2H, m).

REFERENCE EXAMPLE 67

4-[5,5-Bis(acetylthiomethyl)pentyl]-5-methyl-2-(p-tolyl)oxazole

To 4 ml of a solution of 923 mg of 4-[5,5-bis(bromomethyl)pentyl]-5-methyl-2-(p-tolyl)oxazole in polyethylene glycol #200, 1.18 g of potassium thiolacetate was added, and stirred under heating for 1.5 hours at 80° C. To the reaction solution was added water, and the mixture was extracted with ethyl acetate, washed with brine, dried over anhydrous magnesium sulfate and the solvent was distilled off under reduced pressure. The residue was purified by silica gel column chromatography (Wakogel® C-200, n-hexane: ethyl acetate=9:1) to provide 830 mg of the objective compound as brown oil.

$^1$H-NMR (CDCl$_3$) δ: 1.35–1.50 (4H, m), 1.55–1.70 (2H, m), 1.75–1.95 (1H, m), 2.32 (3H, s), 2.33 (6H, s), 2.38 (3H, s), 2.47 (2H, t), 2.82–3.05 (4H, m), 7.20–7.25 (2H, m), 7.84–7.89 (2H, m).

The following compound was prepared by the same procedure as described in Reference Example 67.

5-Methyl-4-(6-acetylthiohexyl)-2-(p-tolyl)oxazole.

REFERENCE EXAMPLE 68

4-[5,5-Bis(mercaptomethyl)pentyl]-5-methyl-2-(p-tolyl)oxazole

To 8 ml of a solution of 830 mg of 4-[5,5-bis(acetylthiomethyl)pentyl]-5-methyl-2-(p-tolyl)oxazole in methanol, 8 ml of aqueous 1 N sodium hydroxide solution was added, and heated to reflux for 1 hour. The reaction solution was acidified with 1 N hydrochloric acid, extracted with dichloromethane and dried over anhydrous magnesium sulfate. The solvent was distilled off under reduced pressure to provide 635 mg of the objective compound as pale yellow oil.

$^1$H-NMR (CDCl$_3$) δ: 1.25–1.95 (9H, m), 2.31 (3H, s), 2.38 (3H, s), 2.48 (2H, t), 2.55–2.85 (4H, m), 7.16–7.24 (2H, m), 7.81–7.89 (2H, dd).

REFERENCE EXAMPLE 69

Ethyl 6-iodohexanoate

To 112 ml of a solution of 13.38 g of ethyl 6-bromohexanoate in acetone, 26.97 g of sodium iodide was added and heated to reflux for 18 hours. The reaction solution was cooled, filtered to remove insolubles and washed with acetone. The filtrate was concentrated and, after addition of water, extracted with ethyl acetate. The organic layer was washed with water and brine sequentially, dried over anhydrous magnesium sulfate and concentrated to provide 16.21 g of the objective compound as red-yellow oil.

$^1$H-NMR (CDCl$_3$) δ: 1.26 (3H, t), 1.39–1.51 (2H, m), 1.58–1.73 (2H, m), 1.78–1.92 (2H, m), 2.31 (2H, t), 3.19 (2H, t), 4.13 (2H, q).

REFERENCE EXAMPLE 70

Ethyl 7-acetyl-7-(p-toluoylamino)heptanoate

A suspension (100 ml) of 60% sodium hydride (2.64 g) in N,N-dimethylformamide was cooled to −18° C. with an ice-sodium chloride bath, and 31 ml of a solution of 12.62 g of 1-(p-toluoylamino)-2-propanone in N,N-dimethylformamide was added dropwise slowly. After 1-hour-stirring, 31 ml of a solution of 16.21 g of ethyl 6-iodohexanoate in N,N-dimethylformamide was added dropwise slowly. The ice-bath was removed and the mixture was stirred for 18 hours at room temperature. After addition of ice-cold water, the reaction solution was extracted with ethyl acetate, washed with water and brine sequentially, dried over anhydrous magnesium sulfate and the solvent was distilled off under reduced pressure. The residue was purified by silica gel column chromatography (Wakogel® C-200, n-hexane: ethyl acetate=3:1) to provide 13.13 g of the objective compound as yellow oil.

$^1$H-NMR (CDCl$_3$) δ: 1.20–1.45 (4H, m), 1.24 (3H, t), 1.54–1.77 (3H, m), 2.01–2.08 (1H, m), 2.23–2.31 (2H, t), 2.40 (3H, s), 2.78 (3H, s), 4.11 (2H, q), 4.18–4.90 (1H, m), 6.90 (1H, d), 7.25 (2H, d), 7.71 (2H, d).

REFERENCE EXAMPLE 71

Ethyl 2-(6-iodohexyloxy)-2-methylpropionate

To 76 ml of a solution of 12.16 g of ethyl 2-(6-bromohexyloxy)-2-methylpropionate in acetone, 18.52 g of sodium iodide was added, and heated to reflux for 18 hours. The reaction solution was cooled, filtered to remove insolubles and washed with acetone. The filtrate was concentrated and, after addition of water, extracted with ethyl acetate. The organic layer was washed with water and brine sequentially, dried over anhydrous magnesium sulfate and concentrated to provide 14.46 g of the objective compound as red-yellow oil.

$^1$H-NMR (CDCl$_3$) δ: 1.29 (3H, t), 1.37–1.40 (4H, m), 1.41 (6H, s), 1.55–1.62 (2H, m), 1.80–1.87 (2H, m), 3.19 (2H, t), 3.56 (2H, t), 4.12 (2H, q).

REFERENCE EXAMPLE 72

Ethyl 2-[7-acetyl-7-(p-toluoylamino)heptyloxy]-2-methylpropionate

A suspension (70 ml) of 1.81 g of 60% sodium hydride in N,N-dimethylformamide was cooled to −18° C. with ice-sodium chloride bath, and 21 ml of a solution of 8.67 g of 1-(p-toluoylamino)-2-propanone in N,N-dimethylformamide was added slowly. After 1-hour-stirring, 21 ml of a solution of 14.10 g of ethyl 2-(6-iodohexyloxy)-2-methylpropionate in N,N-dimethylformamide was added dropwise slowly. The bath was removed and the mixture was stirred for additional 18 hours at room temperature. The reaction solution was, after addition of ice-cold water, extracted with ethyl acetate, washed with water and brine sequentially, dried over anhydrous magnesium sulfate, and the solvent was distilled off under reduced pressure. The residue was purified by silica gel column chromatography (Wakogel® C-200, n-hexane: ethyl acetate=3:1) to provide 12.20 g of the objective compound as yellow crystals.

$^1$H-NMR (CDCl$_3$) δ: 1.23–1.41 (6H, m), 1.27 (3H, t), 1.39 (6H, s), 1.51–1.57 (2H, m), 1.71–1.74 (1H, m), 2.01–2.08 (1H, m), 2.27 (3H, s), 2.40 (3H, s), 3.32 (2H, t), 4.17 (2H, q), 4.80–4.90 (1H, m), 6.89 (1H, d), 7.25 (2H, d), 7.71 (2H, d).

REFERENCE EXAMPLE 73

7-(Benzoylamino)-7-carboxy-(E)-4-heptenoic Acid

To 170 ml of a solution of 8.50 g of diethyl [5-(benzoylamino)-5,5-bis(ethoxycarbonyl)-(E)-2-pentenyl]-malonate in ethanol, 34 ml of aqueous solution of sodium hydroxide (5.53 g) was added, and heated to reflux for 20 hours. The reaction solution was concentrated, and the residue was, after addition of water, washed with diethyl ether. The aqueous layer was acidified with hydrochloric acid, extracted with ethyl acetate, dried over anhydrous magnesium sulfate and concentrated to provide 6.58 g of pale yellow oil. The resulting oil was dissolved in 90 ml of ethyl acetate. To the solution was added 90 ml of xylene and stirred for 15 hours at 130° C. The solvent was distilled off under reduced pressure, and the resulting crystals were washed with isopropyl ether to provide 4.52 g of the objective compound as colorless crystals. M.p. 138° C.

EXAMPLE 1

Methyl 2-methyl-c-5-[4-(5-methyl-2-phenyloxazol-4-yl)butyl]-1,3-dioxane-r-2-carboxylate 4-[5,5-Bis(hydroxymethyl)pentyl]-5-methyl-2-phenyloxazole (36 g) was dissolved in 432 ml of acetonitrile, and 25.4 g of methyl pyruvate was added. To the mixture, 35.3 g of boron trifluoride etherate (about 47%) was added with stirring at room temperature and refluxed for 2 hours. The reaction solution was cooled, poured into an ice-cold water solution of sodium hydrogencarbonate and extracted with ethyl acetate. The organic layer was washed with brine, dried over anhydrous magnesium sulfate and concentrated. The residue was purified by silica gel column chromatography (Wakogel® C-200, n-hexane: ethyl acetate=7.5:1) and fractions eluted earlier were concentrated to provide 16.5 g of the objective compound as colorless oil.

$^1$H-NMR (CDCl$_3$) δ: 1.00–1.12 (2H, m), 1.22–1.40 (2H, m), 1.55–1.70 (5H, m), 1.90–2.20 (1H, m), 2.30 (3H, s), 2.45 (2H, t), 3.39 (2H, t), 3.82 (3H, s), 3.95 (2H, dd), 7.37–7.47 (3H, m), 7.92–8.03 (2H, m).

EXAMPLE 2

Methyl 2-methyl-t-5-[4-(5-methyl-2-phenyloxazol-4-yl)butyl]-1,3-dioxane-r-2-carboxylate The latter fractions of Example 1 were collected and concentrated to obtain 11 g of the residue, which was purified by silica gel column chromatography (Wakogel® C-200, n-hexane: ethyl acetate= 7.5:1) again to provide 0.83 g of the objective compound as colorless oil.

$^1$H-NMR (CDCl$_3$) δ: 1.33–1.44 (3H, m), 1.51 (3H, s), 1.63–1.78 (4H, m), 2.33 (3H, s), 2.51 (2H, t), 3.75–3.81 (2H, m), 3.83 (3H, s), 3.91–3.99 (2H, m), 7.38–7.45 (3H, m), 7.96–8.01 (2H, m).

The following compounds were prepared by the same procedure as described in Examples 1 and 2.

Methyl c-5-[4-(5-methyl-2-phenyloxazol-4-yl)butyl]-1,3-dioxane-r-2-carboxylate,

Methyl t-5-[4-(5-methyl-2-phenyloxazol-4-yl)butyl]-1,3-dioxane-r-2-carboxylate,

Methyl 2-ethyl-c-5-[4-(5-methyl-2-phenyloxazol-4-yl)butyl]-1,3-dioxane-r-2-carboxylate, Methyl 2-isobutyl-c-5-[4-(5-methyl-2-phenyloxazol-4-yl)butyl]-1,3-dioxane-r-2-carboxylate, Methyl 2,5-dimethyl-c-5-[4-(5-methyl-2-phenyloxazol-4-yl)butyl]-1,3-dioxane-r-2-carboxylate, Methyl 2,5-dimethyl-t-5-[4-(5-methyl-2-phenyloxazol-4-yl)butyl]-1,3-dioxane-r-2-carboxylate, Methyl 5-ethyl-2-methyl-c-5-[4-(5-methyl-2-phenyloxazol-4-yl)butyl]-1,3-dioxane-r-2-carboxylate, Methyl 5-ethyl-2-methyl-t-5-[4-(5-methyl-2-phenyloxazol-4-yl)butyl]-1,3-dioxane-r-2-carboxylate, Methyl 2-methyl-c-5-[3-(5-methyl-2-phenyloxazol-4-yl)propyl]-1,3-dioxane-r-2-carboxylate, Methyl 2-methyl-t-5-[3-(5-methyl-2-phenyloxazol-4-yl)propyl]-1,3-dioxane-r-2-carboxylate, Methyl 2-methyl-c-5-{4-[(5-methyl-2-phenyloxazol-4-yl)methyl]benzyl}-1,3-dioxane-r-2-carboxylate, Methyl 2-methyl-c-5-{4-[(5-methyl-2-phenyloxazol-4-yl)methyl]phenyl}-1,3-dioxane-r-2-carboxylate, Methyl 2-methyl-c-5-{3-[(5-methyl-2-phenyloxazol-4-yl)-methyl]phenyl}-1,3-dioxane-r-2-carboxylate, Methyl 2-methyl-c-5-{4-[2-(p-tolyl)-5-trifluoromethyloxazol-4-yl]butyl}-1,3-dioxane-r-2-carboxylate, Methyl 2-methyl-c-5-{4-[5-ethyl-2-(p-tolyl)oxazol-4-yl]butyl}-1,3-dioxane-r-2-carboxylate and Ethyl 2-ethyl-c-5-{4-[5-methyl-2-(p-tolyl)oxazol-4-yl]butyl}-1,3-dioxane-r-2-carboxylate.

EXAMPLE 3

Methyl 2-methyl-c-5-[4-(2-phenyloxazol-4-yl)butyl]-1,3-dioxane-r-2-carboxylate

To 5 ml of acetonitrile, 1.25 g of 4-[5,5-bis(hydroxymethyl)pentyl]-2-phenyloxazole was dissolved, and 927 mg of methyl pyruvate was added. To the mixture, 1.3 g of boron trifluoride etherate (about 47%) was added with stirring at room temperature, and stirred for 30 hours at room temperature. The reaction solution was poured into ice-cold water solution of sodium hydrogencarbonate and extracted with ethyl acetate. The organic layer was washed with brine, dried over anhydrous magnesium sulfate and concentrated. The residue was purified by silica gel column chromatography (Wakogel® C-200, n-hexane: isopropyl ether=1:1) and the fractions eluted earlier were concentrated to provide 450 mg g of the objective compound as white crystals. M.p. 71–74° C.

$^1$H-NMR (CDCl$_3$) δ: 1.01–1.12 (2H, m), 1.27–1.43 (2H, m), 1.51 (3H, s), 1.59–1.74 (2H, m), 1.90–2.20 (1H, m), 2.56 (2H, t), 3.39 (2H, t), 3.83 (3H, s), 3.96 (2H, dd), 7.41–7.47 (4H, m), 7.99–8.05 (2H, m).

EXAMPLE 4

Methyl 2-methyl-t-5-[4-(2-phenyloxazol-4-yl)butyl]-1,3-dioxane-r-2-carboxylate

The latter fractions of Example 3 were collected and concentrated. The residue was purified by silica gel column chromatography (Wakogelo C-200, n-hexane: isopropyl ether=1:1) again to provide 110 mg of the objective compound as colorless oil.

$^1$H-NMR (CDCl$_3$) δ: 1.25–1.48 (2H, m), 1.51 (3H, s), 1.63–1.80 (5H, m), 2.62 (2H, t), 3.76–3.86 (5H, m), 3.92–4.00 (2H, m), 7.41–7.47 (4H, m), 8.00–8.05 (2H, m).

EXAMPLE 5

Methyl 2-methyl-5-{3-[(5-methyl-2-phenyloxazol-4-yl)methyl]benzyl}-1,3-dioxane-2-carboxylate To 5 ml of acetonitrile, 297 mg of 4-{3-[2,2-bis(hydroxymethyl)ethyl]benzyl}-5-methyl-2-phenyloxazole and 369 mg of methyl pyruvate were added. To the mixture was added 544 mg of boron trifluoride etherate (about 47%) with stirring at room temperature, and stirred for 14 hours at room temperature. The reaction solution was poured into an ice-cold water solution of sodium hydrogencarbonate and extracted with ethyl acetate. The organic layer was washed with brine, dried over anhydrous magnesium sulfate and concentrated. The residue was purified by silica gel column chromatography (Wakogel® C-200, n-hexane: ethyl acetate=3:1) to provide 185 mg of a mixture (cis:trans= 2.5:1, based on NMR integral value) as colorless oil.

EXAMPLE 6

Methyl 2-methyl-c-5-{4-[5-methyl-2-(p-tolyl)oxazol-4-yl]butyl}-1,3-dioxane-r-2-carboxylate Methyl c-5-[5-acetyl-5-(p-toluoylamino)pentyl]-2-methyl-1,3-dioxane-r-2-carboxylate (0.85 g) was dissolved in 17 ml of toluene. After addition of 644 mg of phosphorus oxychloride, the mixture was heated to reflux for 2.5 hours. The reaction solution was cooled, poured into ice-cold water, neutralized with aqueous solution of sodium hydrogencarbonate, extracted with ethyl acetate, washed with brine, dried over anhydrous magnesium sulfate and concentrated. The residue was purified by silica gel column chromatography (Wakogel® C-200, chloroform: methanol= 100:1) to provide 0.42 g of the objective compound as white crystals. M.p. 92–94° C.

Elemental analysis for $C_{22}H_{29}NO_5$
Calcd.(%): C, 68.20; H, 7.54; N, 3.61.
Found (%): C, 68.07; H, 7.43; N, 3.65.

The following compounds were prepared by the same procedure as described in Example 6.

Methyl 2-methyl-c-5-[3-(5-methyl-2-phenyloxazol-4-yl)propyl]-1,3-dioxane-r-2-carboxylate, Methyl 2-methyl-c-5-[4-(5-methyl-2-phenyloxazol-4-yl)butyl]-1,3-dioxane-r-2-carboxylate, Methyl 2-methyl-c-5-[5-(5-methyl-2-phenyloxazol-4-yl)pentyl]-1,3-dioxane-r-2-carboxylate, Methyl c-5-{4-[2-(4-fluorophenyl)-5-methyloxazol-4-yl]butyl}-2-methyl-1,3-dioxane-r-2-carboxylate, Methyl c-5-{4-[2-(4-tert-butylphenyl)-5-methyloxazol-4-yl]butyl}-2-methyl-1,3-dioxane-r-2-carboxylate, Methyl 2-methyl-c-5-{4-[5-methyl-2-(4-trifluoromethylphenyl)oxazol-4-yl]butyl}-1,3-dioxane-r-2-carboxylate, Methyl 2-methyl-c-5-[4-(5-methyl-2-phenyloxazol-4-yl)-(E)-2-butenyl]-1,3-dioxane-r-2-carboxylate, Methyl 2-methyl-2-[6-(5-methyl-2-phenyloxazol-4-yl)hexyloxy]propionate, Methyl 2-methyl-2-{6-[5-methyl-2-(p-tolyl)oxazol-4-yl]hexyloxy}propionate, Methyl 2-methyl-2-[6-(5-methyl-2-phenyloxazol-4-yl)-4-hexynyloxy]propionate, Methyl 2-{6-[2-(4-chlorophenyl)-5-methyloxazol-4-yl]hexyloxy}-2-methylpropionate, Methyl 2-{6-[2-(4-fluorophenyl)-5-methyloxazol-4-yl]hexyloxy}-2-methylpropionate, Methyl 2-{6-[2-(4-tert-butylphenyl)-5-methyloxazol-4-yl]-hexyloxy}-2-methylpropionate, Methyl 2-methyl-2-[7-(5-methyl-2-phenyloxazol-4-yl)heptyloxy]propionate, Methyl 2-methyl-2-[5-(5-methyl-2-phenyloxazol-4-yl)pentyloxy]propionate, Methyl 2-[6-(5-ethyl-2-phenyloxazol-4-yl)hexyloxy]-2-methylpropionate, Methyl 2-methyl-2-{6-[5-methyl-2-(4-pyridyl)oxazol-4-yl]hexyloxy}propionate, Methyl 2-methyl-2-{6-[5-methyl-2-(3-pyridyl)oxazol-4-yl]hexyloxy}propionate, Methyl 2-methyl-c-5-{4-[5-methyl-2-(4-chlorophenyl)oxazol-4-yl]butyl}-1,3-dioxane-r-2-carboxylate, Methyl 2-methyl-c-5-{5-[5-methyl-2-(p-tolyl)oxazol-4-yl]pentyl}-1,3-dioxane-r-2-carboxylate, Methyl 2-methyl-c-5-{4-[5-methyl-2-(3-fluoro-4-methylphenyl)oxazol-4-yl]butyl}-1,3-dioxane-r-2-carboxylate, Methyl 2-methyl-c-5-{4-[5-methyl-2-(4-ethylphenyl)oxazol-4-yl]butyl}-1,3-dioxane-r-2-carboxylate, Methyl 2-methyl-c-5-{4-[5-methyl-2-(2,4-dimethylphenyl)oxazol-4-yl]butyl}-1,3-dioxane-r-2-carboxylate, Methyl 2-methyl-c-5-{4-[2-(4-fluoromethylphenyl)-5-methyloxazol-4-yl]butyl}-1,3-dioxane-r-2-carboxylate, Methyl 2-methyl-c-5-{4-[5-methyl-2-(m-tolyl)oxazol-4-yl]butyl}-1,3-dioxane-r-2-carboxylate, Methyl 2-methyl-c-5-{4-[5-methyl-2-(o-tolyl)oxazol-4-yl]butyl}-1,3-dioxane-r-2-carboxylate, Methyl 2-methyl-c-5-{4-[5-methyl-2-(3,4-dimethylphenyl)oxazol-4-yl]butyl}-1,3-dioxane-r-2-carboxylate, Methyl 2-methyl-c-5-{4-[5-methyl-2-(4-methoxyphenyl)-oxazol-4-yl]butyl}-1,3-dioxane-r-2-carboxylate, Methyl 2-methyl-c-5-{4-[5-methyl-2-(2-thienyl)oxazol-4-yl]butyl}-1,3-dioxane-r-2-carboxylate, Methyl 2-methyl-c-5-{4-[2-cyclohexyl-5-methyloxazol-4-yl]butyl}-1,3-dioxane-r-2-carboxylate and Ethyl 2-methyl-2-{6-[5-methyl-2-(p-tolyl)oxazol-4-yl]hexyloxy}propionate.

EXAMPLE 7

Methyl 2-methyl-2-[6-(2-phenyloxazol-4-yl)hexyloxy]propionate

A mixture of 956 mg of benzamide and 1.1 g of methyl 2-(8-chloro-7-oxooctyloxy)-2-methylpropionate was stirred for 2 hours at 120° C. The reaction solution was cooled, dissolved in ethyl acetate, washed by adding sodium hydrogencarbonate, washed with water, dried over anhydrous magnesium sulfate and concentrated. The residue was purified by silica gel column chromatography (Wakogel® C-200, n-hexane: ethyl acetate=9:1) to provide 658 mg of the objective compound as colorless oil.

$^1$H-NMR (CDCl$_3$) δ: 1.36–1.50 (10H, m), 1.55–1.80 (4H, m), 2.54–2.63 (2H, m), 3.35 (2H,t), 3.73 (3H, s), 7.41–7.47 (4H, m), 7.99–8.05 (2H, m).

The following compounds were prepared by the same procedure as described in Example 7.

Methyl 2-methyl-2-[7-(2-phenyloxazol-4-yl)heptyloxy]propionate,

Methyl 2-{7-[2-(4-chlorophenyl)oxazol-4-yl]heptyloxy}-2-methylpropionate,

Methyl 2-{7-[2-(4-fluorophenyl)oxazol-4-yl]heptyloxy}-2-methylpropionate,

Methyl 2-{6-[2-(4-fluorophenyl)oxazol-4-yl]hexyloxy}-2-methylpropionate and

Methyl 2-methyl-2-[8-(2-phenyloxazol-4-yl)octyloxy]propionate.

EXAMPLE 8

Methyl 2-methyl2-[7-(2-phenyltiazole-4-yl)heptyloxy]propionate

A mixture of 783 mg of thiobenzamide and 1.0 g methyl 2-(9-chloro-8-oxononyloxy)-2-methylpropionate were stirred for 2 hours at 120° C. The reaction solution was cooled and dissolved in ethyl acetate, washed by adding sodium hydrogencarbonate, washed with water, dried over anhydrous magnesium sulfate and concentrated. The residue was purified by silica gel column chromatography (Wakogel® C-200, n-hexane: ethyl acetate=9:1) to provide 963 mg of the objective compound as pale yellow oil.

$^1$H-NMR (CDCl$_3$) δ: 1.36–1.39 (6H, m), 1.42 (6H, s), 1.54–1.61 (2H, m), 1.72–1.80 (2H, m), 2.78–2.86 (2H, m), 3.31–3.38 (2H, m), 3.73 (3H, s), 6.87 (1H, s), 7.39–7.46 (3H, m) 7.91–7.96 (2H, m).

The following compound was prepared by the same procedure as described in Example 8.

Methyl 2-methyl-2-[8-(2-phenylthiazole-4-yl)octyloxy]propionate.

EXAMPLE 9

2-Methyl-c-5-[4-(5-methyl-2-phenyloxazol-4-yl)butyl]-1,3-dioxane-r-2-carboxylic acid Methyl 2-methyl-c-5-[4-(5-methyl-2-phenyloxazol-4-yl)butyl]-1,3-dioxane-r-2-carboxylate (15.76 g) was dissolved in 215 ml of methanol, and a solution of 2.53 g of sodium hydroxide/28 ml of water was added and the mixture was refluxed for 4 hours. The reaction solution was cooled, poured into ice-cold water, acidified with dilute hydrochloric acid and extracted with ethyl acetate. The organic layer was washed with brine, dried over anhydrous magnesium sulfate and concentrated. The residue was dissolved with heat in toluene/n-hexane and stood to cool. The precipitate was collected by filtration to provide 13.52 g of the objective compound.

$^1$H-NMR (CDCl$_3$) δ: 1.00–1.15 (2H, m), 1.25–1.45 (2H, m), 1.50–1.70 (5H, m), 1.90–2.20 (1H, m), 2.32 (3H, s), 2.52 (2H, t), 3.49 (2H, dd), 3.99 (2H, dd), 7.40–7.50 (3H, m), 7.90–8.05 (2H, m), 9.70 (1H, br).

Elemental analysis for $C_{20}H_{25}NO_5$

Calcd.(%): C, 66.84; H, 7.01; N, 3.90.

Found (%): C, 66.76; H, 7.09; N, 3.82.

EXAMPLE 10

2-Methyl-c-5-{3-[(5-methyl-2-phenyloxazol-4-yl)methyl]benzyl}-1,3-dioxane-r-2-carboxylic Acid Methyl 2-methyl-5-{3-[(5-methyl-2-phenyloxazol-4-yl)methyl]benzyl}-1,3-dioxane-2-carboxylate (a mixture of cis:trans=3:1) (185 mg) was dissolved in 5 ml of methanol, and 0.5 ml of 2N sodium hydroxide was added and refluxed for 1 hour. The reaction solution was cooled, poured into ice-cold water, acidified with dilute hydrochloric acid and extracted with ethyl acetate. The organic layer was washed with brine, dried over anhydrous magnesium sulfate and concentrated. To the residue was added ether. The precipitated crystals were collected by filtration, recrystallized from acetonitrile and dried to provide 109 mg of the objective compound as white crystals. M.p. 147–149° C.

Elemental analysis for $C_{24}H_{25}NO5$
Calcd.(%): C, 70.75; H, 6.18; N, 3.44.
Found (%): C, 70.85; H, 6.26; N, 3.33.

EXAMPLE 11

2-Methyl-c-5-{4-[5-methyl-2-(p-tolyl)oxazol-4-yl]butyl}-1,3-dioxane-r-2-carboxylic Acid Methyl 2-methyl-c-5-{4-[5-methyl-2-(p-tolyl)oxazol-4-yl]butyl}-1,3-dioxane-r-2-carboxylate (250 mg) was dissolved in 2.5 ml of methanol, and a solution of 51 mg of sodium hydroxide/0.6 ml of water was added and refluxed for 1 hour. The reaction solution was cooled, poured into ice-cold water, acidified with dilute hydrochloric acid and extracted with ethyl acetate. The organic-layer was washed with brine, dried over anhydrous magnesium sulfate and concentrated. To the residue was added ether. The precipitates were collected by filtration, dissolved in acetonitrile under heating and allowed to stand to cool. The precipitates were collected by filtration and dried to provide 196 mg of the objective compound.

Elemental analysis for $C_{21}H_{27}NO_5$
Calcd.(%): C, 67.54; H, 7.29; N, 3.75.
Found (%): C, 67.57; H, 7.25; N, 3.76.

The compounds of Examples 12–52 were prepared by the same procedure as described in Example 11.

EXAMPLE 12

2-Methyl-t-5-[4-(5-methyl-2-phenyloxazol-4-yl)butyl]-1)3-dioxane-r-2-carboxylic Acid M.p, 135–140° C.

$^1$H-NMR (CDCl$_3$) δ: 1.38–1.50 (3H, m), 1.56 (3H, s), 1.60–1.80 (4H, m), 2.33 (3H, s), 2.54 (2H, t), 3.79 (2H, dd), 4.03 (2H, dd), 7.20 (1H, br), 7.40–7.50 (3H, m), 7.90–8.10 (2H, m).

Elemental analysis for $C_{20}H_{25}NO_5$
Calcd.(%): C, 66.84; H, 7.01; N, 3.90.
Found (%): C, 67.35; H, 7.00; N, 3.77.

EXAMPLE 13

2-Methyl-c-5-(5-(5-methyl-2-phenyloxazol-4-yl)pentyl]-1,3-dioxane-r-2-carboxylic acid M.p. 135–137° C.

Elemental analysis for $C_{21}H_{27}NO_5$
Calcd.(%): C, 67.54; H, 7.29; N, 3.75.
Found (%): C, 67.44; H, 7.34; N, 3.77.

EXAMPLE 14

2-Methyl-c-5-[4-(2-phenyloxazol-4-yl)butyl]-1,3-dioxane-r-2-carboxylic Acid

Elemental analysis for $C_{19}H_{23}NO_5$
Calcd.(%): C, 66.07; H, 6.71; N, 4.06.
Found (%): C, 66.09; H, 6.75; N, 4.03.

EXAMPLE 15 c-5-[4-(5-Methyl-2-phenyloxazol-4-yl)butyl]-1,3-dioxane-r-2-carboxylic Acid

M.p. 119–121° C.

Elemental analysis for $C_{19}H_{23}NO_5$
Calcd.(%): C, 66.07; H, 6.71; N, 4.06.
Found (%): C, 66.02; H, 6.87; N, 4.18.

EXAMPLE 16 t-5-[4-(5-Methyl-2-phenyloxazol-4-yl)butyl]-1,3-dioxane-r-2-carboxylic Acid

M.p. 103–105° C.

Elemental analysis for $C_{19}H_{23}NO_5$
Calcd.(%): C, 66.07; H, 6.71; N, 4.06.
Found (%): C, 66.07; H, 6.99; N, 4.04.

EXAMPLE 17

2-Methyl-t-5-{4-[5-methyl-2-(p-tolyl)oxazol-4-yl]butyl}-1,3-dioxane-r-2-carboxylic Acid M.p. 120–122° C.

Elemental analysis for $C_{21}H_{27}NO_5$
Calcd.(%): C, 67.54; H, 7.29; N, 3.75.
Found (%): C, 67.61; H, 7.35; N, 3.74.

EXAMPLE 18 c-5-{4-[2-(4-tert-Butylphenyl)-5-methyloxazol-4-yl]butyl}-2-methyl-1,3-dioxane-r-2-carboxylic Acid Elemental analysis for $C_{24}H_{33}NO_5$
Calcd.(%): C, 69.37; H, 8.00; N, 3.37.
Found (%): C, 69.26; H, 7.96; N, 3.43.

EXAMPLE 19 c-5-{4-[2-(4-Fluorophenyl)-5-methyloxazol-4-yl]butyl}-2-methyl-1,3-dioxane-r-2-carboxylic Acid M.p. 138–139.5° C.

Elemental analysis for $C_{20}H_{24}FNO_5$
Calcd.(%): C, 63.65; H, 6.41; N, 3.71.
Found (%): C, 63.62; H, 6.58; N, 3.69.

EXAMPLE 20

2-Methyl-c-5-{4-[5-methyl-2-(4-trifluoromethylphenyl)-oxazol-4-yl]butyl}-1,3-dioxane-r-2-carboxylic Acid Elemental analysis for $C_{21}H_{24}F_3NO_5$
Calcd.(%): C, 59.01; H, 5.66; N, 3.28.
Found (%): C, 59.14; H, 5.83; N, 3.29.

EXAMPLE 21

2-Ethyl-c-5-[4-(5-methyl-2-phenyloxazol-4-yl)butyl]-1,3-dioxane-r-2-carboxylic Acid Elemental analysis for $C_{21}H_{27}NO_5$
Calcd.(%): C, 67.54; H, 7.29; N, 3.75.
Found (%): C, 67.05; H, 7.24; N, 3.60.

EXAMPLE 22

2-Isobutyl-c-5-[4-(5-methyl-2-phenyloxazol-4-yl)butyl]-1,3-dioxane-r-2-carboxylic Acid M.p. 126–130° C.

Elemental analysis for $C_{23}H_{31}NO_5$

Calcd.(%): C, 68.80; H, 7.78; N, 3.49
Found (%): C, 68.72; H, 7.88; N, 3.45.

EXAMPLE 23

2,5-Dimethyl-c-5-[4-(5-methyl-2-phenyloxazol-4-yl)butyl]-1,3-dioxane-r-2-carboxylic Acid
M.p. 147–150° C.
Elemental analysis for $C_{21}H_{27}NO_5$
Calcd.(%): C, 67.54; H, 7.29; N, 3.75.
Found (%): C, 68.17; H, 7.76; N, 3.46.

EXAMPLE 24

2,5-Dimethyl-t-5-[4-(5-methyl-2-phenyloxazol-4-yl)butyl]-1,3-dioxane-r-2-carboxylic Acid
M.p. 142–144° C.
Elemental analysis for $C_{21}H_{27}NO_5$
Calcd.(%): C, 67.54; H, 7.29; N, 3.75
Found (%): C, 67.35; H, 7.37; N, 3.44.

EXAMPLE 25

5-Ethyl-2-methyl-c-5-[4-(5-methyl-2-phenyloxazol-4-yl)butyl]-1,3-dioxane-r-2-carboxylic acid
M.p. 155–158° C.
Elemental analysis for $C_{22}H_{29}NO_5$
Calcd.(%): C, 68.20; H, 7.54; N, 3.61.
Found (%): C, 68.18; H, 7.59; N, 3.49.

EXAMPLE 26

5-Ethyl-2-methyl-t-5-[4-(5-methyl-2-phenyloxazol-4-yl)butyl]-1,3-dioxane-r-2-carboxylic Acid
M.p. 126–130° C.
Elemental analysis for $C_{22}H_{29}NO_5$
Calcd.(%): C, 68.20; H, 7.54; N, 3.61
Found (%): C, 67.77; H, 7.57; N, 3.47.

EXAMPLE 27

2-Methyl-c-5-[3-(5-methyl-2-phenyloxazol-4-yl)propyl]-1,3-dioxane-r-2-carboxylic Acid
M.p. 131–134° C.
Elemental analysis for $C_{19}H_{23}NO_5$
Calcd.(%): C, 66.07; H, 6.71; N, 4.06.
Found (%): C, 65.59; H, 6.69; N, 3.92.

EXAMPLE 28

2-Methyl-t-5-[3-(5-methyl-2-phenyloxazol-4-yl)propyl]-1,3-dioxane-r-2-carboxylic Acid
M.p. 164–166° C.
Elemental analysis for $C_{19}H_{23}NO_5$
Calcd.(%): C, 66.07; H, 6.71; N, 4.06.
Found (%): C, 65.64; H, 6.70; N, 3.91.

EXAMPLE 29

2-Methyl-c-5-[4-(5-methyl-2-phenyloxazol-4-yl)-(E)-2-butenyl]-1,3-dioxane-r-2-carboxylic Acid
M.p. 148–150° C.
Elemental analysis for $C_{20}H_{23}NO_5$
Calcd.(%): C, 67.21; H, 6.49; N, 3.92.
Found (%): C, 67.26; H, 6.36; N, 3.82.

EXAMPLE 30

2-Methyl-5-{4-[(5-methyl-2-phenyloxazol-4-yl)methyl]benzyl}-1,3-dioxane-2-carboxylic Acid
A mixture (cis:trans=4:1 based on NMR integral value) was obtained.
Elemental analysis for $C_{24}H_{25}NO_5$
Calcd.(%): C, 70.75; H, 6.18; N, 3.44.
Found (%): C, 70.69; H, 6.23; N, 3.45.

EXAMPLE 31

2-Methyl-c-5-{4-[(5-methyl-2-phenyloxazol-4-yl)methyl]phenyl}-1,3-dioxane-r-2-carboxylic Acid
M.p. 215–216° C.
Elemental analysis for $C_{23}H_{23}NO_5$
Calcd.(%): C, 70.21; H, 5.89; N, 3.56.
Found (%): C, 70.02; H, 5.88; N, 3.35.

EXAMPLE 32

2-Methyl-c-5-{3-[(5-methyl-2-phenyloxazol-4-yl)methyl]phenyl}-1,3-dioxane-r-2-carboxylic Acid
M.p. 122–124° C.
Elemental analysis for $C_{23}H_{23}NO_5$
Calcd.(%): C, 70.21; H, 5.89; N, 3.56.
Found (%): C, 70.05; H, 6.08; N, 3.51.

EXAMPLE 33

2-Methyl-c-5-{4-[5-methyl-2-(3-pyridyl)oxazol-4-yl]butyl}-1,3-dioxane-r-2-carboxylic Acid
M.p. 126–129° C.
Elemental analysis for $C_{19}H_{24}N_2O_5$
Calcd.(%): C, 63.32; H, 6.71; N, 7.77.
Found (%): C, 63.16; H, 6.73; N, 7.57.

EXAMPLE 34

2-Methyl-2-[5-(5-methyl-2-phenyloxazol-4-yl)pentyloxy]propionic Acid
M.p. 66–68° C.
Elemental analysis for $C_{19}H_{25}NO_4, H_2O$
Calcd.(%): C, 65.31; H, 7.79; N, 4.01.
Found (%): C, 65.20; H, 7.84; N, 4.03.

EXAMPLE 35

2-Methyl-2-[6-(5-methyl-2-phenyloxazol-4-yl)hexyloxy]propionic Acid
Elemental analysis for $C_{20}H_{27}NO_4$
Calcd.(%): C, 69.54; H, 7.88; N, 4.05.
Found (%): C, 69.12; H, 7.86; N, 4.11.

EXAMPLE 36

2-Methyl-2-[7-(5-methyl-2-phenyloxazol-4-yl)heptyloxy]propionic Acid
M.p. 70–71° C.
Elemental analysis for $C_{21}H_{29}NO_4$
Calcd.(%): C, 70.17; H, 8.13; N, 3.90.
Found (%): C, 70.03; H, 8.15; N, 3.90.

EXAMPLE 37

2-Methyl-2-{6-[5-methyl-2-(p-tolyl)oxazol-4-yl]hexyloxy}propionic Acid
Elemental analysis for $C_{21}H_{29}NO_4$
Calcd.(%): C, 70.17; H, 8.13; N, 3.90.
Found (%): C, 70.07; H, 8.07; N, 3.92.

EXAMPLE 38

2-Methyl-2-[6-(5-methyl-2-phenyloxazol-4-yl)-4-hexynyloxy]propionic Acid
Elemental analysis for $C_{20}H_{23}NO_4$
Calcd.(%): C, 70.36; H, 6.79; N, 4.10.
Found (%): C, 70.24; H, 6.51; N, 3.90.

EXAMPLE 39

2-{6-[2-(4-Chlorophenyl)-5-methyloxazol-4-yl]hexyloxyl-2-methylpropionic Acid
Elemental analysis for $C_{20}H_{26}ClNO_4$
Calcd.(%): C, 63.24; H, 6.90; N, 3.69.
Found (%): C, 63.17; H, 6.82; N, 3.82.

EXAMPLE 40

2-{6-[2-(4-Fluorophenyl)-5-methyloxazol-4-yl]hexyloxy}-2-methylpropionic Acid
M.p. 64–67° C.
Elemental analysis for $C_{20}H_{26}FNO_4$
Calcd.(%): C, 66.10; H, 7.21; N, 3.85.
Found (%): C, 66.18; H, 7.30; N, 4.06.

EXAMPLE 41

2-{6-[2-(4-tert-Butylphenyl)-5-methyloxazol-4-yl]hexyloxy}-2-methylpropionic Acid
M.p. 89–91° C.
Elemental analysis for $C_{24}H_{35}NO_4$
Calcd.(%): C, 71.79; H, 8.79; N, 3.49.
Found (%): C, 71.79; H, 8.81; N, 3.52.

EXAMPLE 42

2-[6-(5-Ethyl-2-phenyloxazol-4-yl)hexyloxy]-2-methylpropionic Acid
M.p. 88.5–89° C.
Elemental analysis for $C_{21}H_{29}NO_4$
Calcd.(%): C, 70.17; H, 8.13; N, 3.90.
Found (%): C, 70.36; H, 8.07; N, 3.90.

EXAMPLE 43

2-Methyl-2-[6-(2-phenyloxazol-4-yl)hexyloxy]propionic Acid
M.p. 75–77° C.
Elemental analysis for $C_{19}H_{25}NO_4$
Calcd.(%): C, 68.86; H, 7.60; N, 4.23.
Found (%): C, 68.89; H, 7.62; N, 4.27.

EXAMPLE 44

2-Methyl-2-(7-(2-phenyloxazol-4-yl)heptyloxy]propionic Acid
M.p. 72–75° C.
Elemental analysis for $C_{20}H_{27}NO_4$
Calcd.(%): C, 69.54; H, 7.88; N, 4.05.
Found (%): C, 69.67; H, 7.89; N, 4.06.

EXAMPLE 45

2-Methyl-2-[8-(2-phenyloxazol-4-yl)octyloxy]propionic Acid
M.p. 59–61° C.
Elemental analysis for $C_{21}H_{29}NO_4$
Calcd.(%): C, 70.17; H, 8.13; N, 3.90.
Found (%): C, 70.02; H, 8.30; N, 3.91.

EXAMPLE 46

2-{7-[2-(4-Chlorophenyl)oxazol-4-yl]heptyloxy}-2-methylpropionic Acid
M.p. 91–93° C.
Elemental analysis for $C_{20}H_{26}ClNO_4$
Calcd.(%): C, 63.24; H, 6.90; N, 3.69.
Found (%): C, 63.39; H, 6.98; N, 3.72.

EXAMPLE 47

2-{7-[2-(4-Fluorophenyl)oxazol-4-yl]heptyloxy}-2-methylpropionic Acid
M.p. 67–74° C.
Elemental analysis for $C_{20}H_{26}FNO_4$
Calcd.(%): C, 66.10; H, 7.21; N, 3.85.
Found (%): C, 65.90; H, 7.06; N, 3.84.

EXAMPLE 48

2-{6-[2-(4-Fluorophenyl)oxazol-4-yl]hexyloxy}-2-methylpropionic Acid
M.p. 80–83° C.
Elemental analysis for $C_{19}H_{24}FNO_4$
Calcd.(%): C, 65.31; H, 6.92; N, 4.01.
Found (%): C, 65.15; H, 6.77; N, 3.91.

EXAMPLE 49

2-Methyl-2-[7-(2-phenylthiazol-4-yl)heptyloxy]propionic Acid
M.p. 71–72° C.
Elemental analysis for $C_{20}H_{27}NO_3S$
Calcd.(%): C, 66.45; H, 7.53; N, 3.87.
Found (%): C, 66.46; H, 7.57; N, 3.98.

EXAMPLE 50

2-Methyl-2-[8-(2-phenylthiazol-4-yl)octyloxy]propionic Acid
M.p. 64–70° C.
Elemental analysis for $C_{21}H_{29}NO_3S \cdot H_2O$
Calcd.(%): C, 64.09; H, 7.94; N, 3.56.
Found (%): C, 64.67; H, 7.89; N, 3.83.

EXAMPLE 51

2-Methyl-2-{6-[5-methyl-2-(4-pyridyl)oxazol-4-yl]hexyloxy}propionic Acid
M.p. 91–93° C.
Elemental analysis for $C_{19}H_{26}N_2O_4$
Calcd.(%): C, 65.88; H, 7.56; N, 8.09.
Found (%): C, 65.79; H, 7.52; N, 8.03.

EXAMPLE 52

2-Methyl-2-{6-[5-methyl-2-(3-pyridyl)oxazol-4-yl]hexyloxy}propionic Acid $^1$H-NMR (CDCl$_3$) δ: 1.25–1.50 (10H, m), 1.55–1.75 (4H, m), 2.34 (3H, s), 2.50 (2H, t), 3.45 (2H, t), 7.35–7.42 (1H, m), 8.26–8.30 (1H, m), 8.62–8.66 (1H, m), 9.21–9.22 (1H, m).

EXAMPLE 53

2-Methyl-c-5-[4-(5-methyl-2-phenyloxazol-4-yl)-(E)-3-butenyl]-1,3-dioxane-r-2-carboxylic Acid Methyl 2-methyl-c-5-[4-(5-methyl-2-phenyloxazol-4-yl)butyl]-1,3-dioxane-r-2-carboxylate (7.5 g) was dissolved in 30 ml of N,N-dimethylformamide, and a solution of 3.57 g of N-bromosuccinimide (NBS)/20 ml of N,N-dimethylformamide was added dropwise with stirring under ice-cooling. After 30-minute-stirring, the reaction solution was poured into ice-cold water and extracted with ethyl acetate. The organic layer was washed with brine, dried over anhydrous magnesium sulfate and concentrated. The residue was purified by silica gel column chromatography (Wakogel® C-200, n-hexane: ethyl acetate=7:1) to provide 215 mg of oil. The resulting oil was dissolved in 3 ml of methanol. To the solution were added 70 mg of sodium hydroxide and 0.8 ml of water, and the mixture was refluxed for 2.5 hours, and concentrated. After addition of ice, the residue was acidified with 1 N hydrochloric acid, extracted with ethyl acetate, washed with brine, dried over anhydrous magnesium sulfate and concentrated. The residue was purified by silica gel column chromatography (Wakogel® C-200, ethyl acetate) to provide 30 mg of the objective compound.

$^1$H-NMR (CDCl$_3$) δ: 1.22 (2H, ddd), 1.65 (3H, s), 2.00–2.30 (3H, m), 2.38 (3H, s), 3.51 (2H, dd), 4.02 (2H, dd), 4.20 (1H, br), 6.15–6.40 (2H, m), 7.40–7.60 (3H, m), 7.90–8.20 (2H, m).

EXAMPLE 54

Potassium 2-methyl-2-[6-(5-methyl-2-phenyloxazol-4-yl)-(E)-4-hexenyloxy]propionate To 20 ml of a solution of 920 mg of methyl 2-[6-(5-methyl-2-phenyloxazol-4-yl)-(E)-4-hexenyloxy]-2-methyl propionate in methanol, 20 ml of an aqueous solution of 206 mg of sodium hydroxide was added, and heated to reflux for 20 hours. The reaction solution was concentrated. After addition of ice-cold water, the residue was acidified with 10% hydrochloric acid. The mixture was extracted with ethyl acetate, washed with water, dried over anhydrous magnesium sulfate. The solvent was distilled off under reduced pressure. The residue was purified by silica gel column chromatography (Wakogel® C-200, chloroform) to provide 670 mg of 2-[6-(5-methyl-2-phenyloxazol-4-yl)-(E)-4-hexenyloxy]-2-methyl propionic acid as colorless oil. A portion (100 mg) of the oil was converted into potassium salt with potassium hydroxide. After addition of isopropyl ether, the precipitates were collected by filtration to provide 88 mg of the objective compound.

Elemental analysis for C$_{20}$H$_{24}$NO$_4$K 1/2H$_2$O

Calcd.(%): C, 61.51; H, 6.45; N, 3.59.

Found (%): C, 61.56; H, 6.24; N, 3.53.

EXAMPLE 55

2-Methyl-2-[6-(5-methyl-2-phenyloxazol-4-yl)hexyloxy]-propanol

To 214 ml of dry ether, 1.35 g of lithium aluminum hydride was added, and a solution of 10.7 g of methyl 2-methyl-2-[6-(5-methyl-2-phenyloxazol-4-yl)hexyloxy]-propionate/40 ml of dry ether was added dropwise with stirring under ice-cooling and stirred for 1 hour. To the mixture was added dropwise 43 ml of tetrahydrofuran/1.7 ml of water followed by addition of 6.3 ml of water and 1.7 ml of 1 N sodium hydroxide, and the mixture was stirred for 15 minutes and filtrated to remove insolubles. The filtrate was concentrated. The residue was purified by silica gel column chromatography (Wakogel® C-200, n-hexane: ethyl acetate=3:1) to provide 8.44 g of the objective compound.

Elemental analysis for C$_{20}$H$_{29}$NO$_3$ 1/2H$_2$O

Calcd.(%): C, 70.55; H, 8.88; N, 4.11.

Found (%): C, 70.95; H, 8.67; N, 4.21.

The compounds of Examples 56–58 were prepared by the same procedure as described in Example 55.

EXAMPLE 56

2-{6-[2-(4-tert-Butylphenyl)-5-methyloxazole-4-yl]-hexyloxy}-2-methylpropanol $^1$H-NMR (CDCl$_3$) δ: 1.14 (6H, s), 1.34–1.43 (11H, m), 1.45–1.75 (6H, m), 1.95–2.10 (1H, m), 2.31 (3H, s), 2.47 (2H, t), 3.30–3.41 (4H, m), 7.41–7.45 (2H, m), 7.88–7.92 (2H, m).

Elemental analysis for C$_{24}$H$_{37}$NO$_3$·H$_2$O

Calcd.(%): C, 71.07; H, 9.69; N, 3.45.

Found (%): C, 70.89; H, 9.32; N, 3.20.

EXAMPLE 57

2-Methyl-2-{6-[5-methyl-2-(3-pyridyl)oxazol-4-yl]hexyloxy}propanol $^1$H-NMR (CDCl$_3$) δ: 1.15 (6H, s), 1.34–1.40 (4H, m), 1.45–1.85 (4H, m), 1.95–2.10 (1H, m), 2.34 (3H, s), 2.45 (2H, t), 3.31–3.40 (4H, m), 7.27–7.36 (1H, m), 8.22–8.28 (1H, m), 8.61–8.64 (1H, m), 9.20–9.21 (1H, m).

Elemental analysis for C$_{19}$H$_{28}$N$_2$O$_3$—H$_2$O

Calcd.(%): C, 65.12; H, 8.63; N, 7.99.

Found (%): C, 65.24; H, 8.40; N, 7.73.

EXAMPLE 58 r-2-Hydroxymethyl-2-methyl-c-5-{4-[5-methyl-2-(p-tolyl)oxazol-4-yl]butyl}-1,3-dioxane M.p. 58–59° C.

Elemental analysis for C$_{21}$H$_{29}$NO$_4$

Calcd.(%): C, 70.17; H, 8.13; N, 3.90.

Found (%): C, 69.97; H, 8.05; N, 3.88.

EXAMPLE 59

2-Methyl-2-{6-[5-methyl-2-(4-pyridyl)oxazol-4-yl]hexyloxy}propanolmethansulfonate Salt Methyl 2-methyl-2-{6-[5-methyl-2-(4-pyridyl)oxazol-4-yl]hexyloxy}propionate (210 mg) was dissolved in 20 ml of dry ether, and 44 mg of lithium aluminum hydride was added and stirred for 30 minutes under ice-cooling. Then, 5 ml of tetrahydrofuran/0.33 ml of water was added dropwise, stirred for 15 minutes' and filtrated to remove insolubles, and the filtrate was concentrated. The residue was dissolved into ether. To the solution was added 59 mg of methanesulfonic acid/1 ml of ether, and filtered to collect precipitated crystals, which were washed with ether and dried to provide 195 mg of the objective compound as pale yellow crystals. M.p. 128–130° C.

Elemental analysis for $C_{19}H_{28}N_2O_3 \cdot CH_4O_3S \cdot H_2O$
Calcd.(%): C, 53.79; H, 7.67; N, 6.27.
Found (%): C, 53.87; H, 7.28; N, 6.17.

EXAMPLE 60

2-Methyl-c-5-[4-(5-methyl-2-phenyloxazol-4-yl)butyl]-1,3-dioxane-r-2-carbohydroxamic Acid 2-Methyl-c-5-[4-(5-methyl-2-phenyloxazol-4-yl)butyl]-1,3-dioxane-r-2-carboxylic acid (350 mg) was dissolved in 7.5 ml of tetrahydrofuran, and 174 mg of 1,1'-carbonyldiimidazole was added and stirred for 24 hours at room temperature. The reaction solution was concentrated and 3 ml of methanol was added to dissolve the residue, and a solution of 190 mg of hydroxyl ammonium chloride/6 ml of methanol and 336 mg of triethylamine were added dropwise, and stirred for 4 hours at room temperature. The reaction solution was poured into ice-cold water, extracted with ethyl acetate, washed with saturated sodium hydrogen carbonate solution and brine, dried over anhydrous magnesium sulfate and concentrated. The residue was purified by silica gel column chromatography (Wakogel® C-200, chloroform: methanol=100:1) to provide 53.8 mg of the objective compound as white crystals. M.p. 115–116° C.

Elemental analysis for $C_{20}H_{26}N_2O_5 \cdot \frac{1}{4}H_2O$
Calcd.(%): C, 63.39; H, 7.05; N, 7.39.
Found (%): C, 63.35; H, 6.85; N, 7.37.

The compounds of Examples 61–77 were prepared by the same procedure as described in Example 11.

EXAMPLE 61

2-Methyl-c-5-{4-[5-methyl-2-(4-chlorophenyl)oxazol-4-yl]butyl}-1,3-dioxane-r-2-carboxylic Acid
M.p. 145–146° C.
Elemental analysis for $C_{20}H_{24}ClNO_5$
Calcd.(%): C, 60.99; H, 6.14; N, 3.56.
Found (%): C, 60.75; H, 6.25; N, 3.36.

EXAMPLE 62

2-Methyl-c-5-{5-[5-methyl-2-(p-tolyl)oxazol-4-yl]pentyl}-1,3-dioxane-r-2-carboxylic Acid
M.p. 118–119° C.
Elemental analysis for $C_{22}H_{29}NO_5$
Calcd.(%): C, 68.20; H, 7.54; N, 3.61.
Found (%): C, 68.20; H, 7.53; N, 3.60.

EXAMPLE 63

2-Ethyl-c-5-{4-[5-methyl-2-(p-tolyl)oxazol-4-yl]-butyl}-1,3-dioxane-r-2-carboxylic Acid
M.p. 123–126° C.
Elemental analysis for $C_{22}H_{29}NO_5$
Calcd.(%): C, 68.20; H, 7.54; N, 3.61.
Found (%): C, 69.22; H, 7.53; N, 3.21.

EXAMPLE 64

2-Methyl-c-5-{4-[5-methyl-2-(3-fluoro-4-methylphenyl)-oxazol-4-yl]butyl}-1,3-dioxane-r-2-carboxylic Acid Elemental analysis for $C_{21}H_{26}FNO_5$
Calcd.(%): C, 64.44; H, 6.69; N, 3.58.
Found (%): C, 64.49; H, 6.68; N, 3.90.

EXAMPLE 65

2-Methyl-c-5-{4-[5-methyl-2-(4-ethylphenyl)oxazol-4-yl]butyl}-1,3-dioxane-r-2-carboxylic Acid
M.p. 147° C.
Elemental analysis for $C_{22}H_{29}NO_5$
Calcd.(%): C, 68.20; H, 7.54; N, 3.61.
Found (%): C, 67.99; H, 7.50; N, 3.76.

EXAMPLE 66

2-Methyl-c-5-{4-[2-(p-tolyl)-5-trifluoromethyloxazol-4-yl]butyl}1-1,3-dioxane-r-2-carboxylic Acid
M.p. 130–131° C.
Elemental analysis for $C_{21}H_{24}F_3NO_5$
Calcd.(%): C, 59.01; H, 5.66; N, 3.28.
Found (%): C, 59.11; H, 5.67; N, 3.16.

EXAMPLE 67

2-Methyl-c-5-{4-[5-methyl-2-(2,4-dimethylphenyl)-oxazol-4-yl]butyl}-1,3-dioxane-r-2-carboxylic Acid
M.p. 130–1310C.
Elemental analysis for $C_{22}H_{29}NO_5$
Calcd.(%): C, 68.20; H, 7.54; N, 3.61.
Found (%): C, 68.25; H, 7.53; N, 3.65.

EXAMPLE 68

2-Methyl-c-5-{4-[2-(4-fluoromethylphenyl)-5-methyloxazol-4-yl]butyl}-1,3-dioxane-r-2-carboxylic Acid
M.p. 144–145° C.
Elemental analysis for $C_{21}H_{26}FNO_5$
Calcd.(%): C, 64.44; H, 6.69; N, 3.58.
Found (%): C, 64.35; H, 6.69; N, 3.52.

EXAMPLE 69

2-Methyl-c-5-{4-[5-ethyl-2-(p-tolyl)oxazol-4-yl]-butyl}-1,3-dioxane-r-2-carboxylic Acid
M.p. 160–161° C.
Elemental analysis for $C_{22}H_{29}NO_5$
Calcd.(%): C, 68.20; H, 7.54; N, 3.61.
Found (%): C, 68.15; H, 7.52; N, 3.56.

EXAMPLE 70

2-Methyl-c-5-{4-[5-methyl-2-(p-tolyl)thiazol-4-yl]-butyl}-1,3-dioxane-r-2-carboxylic Acid
Elemental analysis for $C_{21}H_{27}NO_4S$
Calcd.(%): C, 64.76; H, 6.99; N, 3.60.
Found (%): C, 64.68; H, 6.97; N, 3.64.

EXAMPLE 71

2-Methyl-c-5-{4-[5-methyl-2-(m-tolyl)oxazol-4-yl]butyl}-1,3-dioxane-r-2-carboxylic Acid
Elemental analysis for $C_{21}H_{27}NO_5$
Calcd.(%): C, 67.54; H, 7.29; N, 3.75.
Found (%): C, 67.57; H, 7.22; N, 3.80.

EXAMPLE 72

2-Methyl-c-5-{4-[5-methyl-2-(o-tolyl)oxazol-4-yl]butyl}-1,3-dioxane-r-2-carboxylic Acid M.p. 121–122° C.

Elemental analysis for $C_{21}H_{27}NO_5$

Calcd.(%): C, 67.54; H, 7.29; N, 3.75.

Found (%): C, 67.47; H, 7.29; N, 3.71.

EXAMPLE 73

2-Methyl-c-5-{4-[5-methyl-2-(3,4-dimethylphenyl)-oxazol-4-yl]butyl}-1,3-dioxane-r-2-carboxylic Acid Elemental analysis for $C_{22}H_{29}NO_5$ Calcd.(%): C, 68.20; H, 7.54; N, 3.61.

Found (%): C, 68.31; H, 7.53; N, 3.65.

EXAMPLE 74

2-Methyl-c-5-{4-[5-methyl-2-(4-methoxyphenyl)oxazol-4-yl]butyl}-1,3-dioxane-r-2-carboxylic Acid Elemental analysis for $C_{21}H_{27}NO_6$ Calcd.(%): C, 64.77; H, 6.99; N, 3.60.

Found (%): C, 64.80; H, 7.13; N, 3.57.

EXAMPLE 75

2-Methyl-c-5-{4-[5-methyl-2-(2-thienyl)oxazol-4-yl]butyl}-1,3-dioxane-r-2-carboxylic Acid Elemental analysis for $C_{18}H_{23}NO_5S$ Calcd.(%): C, 59.16; H, 6.34; N, 3.83.

Found (%): C, 59.45; H, 6.32; N, 3.76.

EXAMPLE 76

2-Methyl-c-5-{4-[2-cyclohexyl-5-methyloxazol-4-yl]butyl}-1,3-dioxane-r-2-carboxylic Acid M.p. 118–121° C.

Elemental analysis for $C_{20}H_{31}NO_5$

Calcd.(%): C, 65.73; H, 8.55; N, 3.83.

Found (%): C, 65.75; H, 8.57; N, 3.80.

EXAMPLE 77

2-Methyl-c-5-{4-[1,5-dimethyl-2-(p-tolyl)imidazole-4-yl]butyl}-1,3-dioxane-r-2-carboxylic Acid M.p. 192–194° C. (decomposed).

Elemental analysis for $C_{22}H_{30}N_2O_4 \cdot H_2O$

Calcd.(%): C, 65.32; H, 7.97; N, 6.93.

Found (%): C, 65.36; H, 7.58; N, 6.75.

EXAMPLE 78

Methyl 2-methyl-c-5-[3-{[5-methyl-2-(p-tolyl)oxazol-4-yl]methyl}benzyl]-1,3-dioxane-r-2-carboxylate 2-[3-{[5-Methyl-2-(p-tolyl)oxazol-4-yl]methyl}benzyl]-1,3-propanediol (2.29 g) was dissolved in 38 ml of acetonitrile, and 2.65 g of methyl pyruvate was added. To the mixture, 3.69 g of boron trifluoride etherate (about 47%) was added with stirring at room temperature, and stirred for 18 hours at room temperature. The reaction solution was poured into an aqueous solution of sodium hydrogencarbonate, and extracted with ethyl acetate. The organic layer was washed with water, dried over anhydrous magnesium sulfate and concentrated. The residue was purified by silica gel column chromatography (Wakogel® C-200, n-hexane: ethyl acetate=4:1) and the fractions eluted earlier were concentrated to provide 752 mg g of the objective compound as colorless oil.

$^1$H-NMR (CDCl$_3$) δ: 1.49 (3H, s), 2.20–2.35 (3H, m), 2.25 (3H, s), 2.38 (3H, s), 3.48 (2H, t), 3.80–3.95 (4H, m), 3.83 (3H, s), 6.92–7.24 (6H, m), 7.80–7.90 (2H, m).

EXAMPLE 79

Methyl 2-methyl-t-5-[3-{[5-methyl-2-(p-tolyl)oxazol-4-yl]methyl}benzyl]-1,3-dioxane-r-2-carboxylate The latter fractions of Example 78 were collected and concentrated to provide 294 mg of the objective compound as colorless oil.

$^1$H-NMR (CDCl$_3$) δ: 1.57 (3H, s), 2.20–2.35 (1H, m), 2.25 (3H, s), 2.38 (3H, s), 2.98 (2H, d), 3.70–3.88 (4H, m), 3.82 (3H, s), 3.93 (2H, dd), 7.00–7.30 (6H, m), 7.87 (2H, d).

EXAMPLE 80

2-Methyl-c-5-[3-{[5-methyl-2-(p-tolyl)oxazol-4-yl]-methyl}benzyl]-1,3-dioxane-r-2-carboxylic Acid To 20 ml of methanol, 968 mg of methyl 2-methyl-c-5-[3-{[5-methyl-2-(p-tolyl)oxazol-4-yl]methyl}benzyl]-1,3-dioxane-r-2-carboxylate was dissolved. After addition of 3.3 ml of aqueous 1 N sodium hydroxide solution, the mixture was heated to reflux for 1.5 hours. The reaction solution was concentrated. The residue was, after addition of water, washed with diethyl ether. The aqueous layer was acidified with 1 N hydrochloric acid and extracted with diethyl ether, dried over anhydrous magnesium sulfate and concentrated. The residue was crystallized by adding diethyl ether, and washed with isopropyl ether to provide 733 mg of the objective compound as colorless crystals.

M.p. 151–152° C.

Elemental analysis for $C_{25}H_{27}NO_5$

Calcd.(%): C, 71.24; H, 6.46; N, 3.32.

Found (%): C, 71.50; H, 6.42; N, 3.48.

EXAMPLE 81

2-Methyl-t-5-[3-{[5-methyl-2-(p-tolyl)oxazol-4-yl]methyl}benzyl]-1,3-dioxane-r-2-carboxylic Acid The objective compound was prepared by the same procedure as Example 80.

Elemental analysis for $C_{25}H_{27}NO_5$

Calcd.(%): C, 71.24; H, 6.46; N, 3.32.

Found (%): C, 70.18; H, 6.34; N, 3.31.

EXAMPLE 82

2-Methyl-c-5-{4-[5-methyl-2-(p-tolyl)oxazol-4-yl]butyl}-1,3-dithiane-r-2-carboxylic Acid To 2 ml of a solution of 124 mg of methyl 2-methyl-c-5-{4-[5-methyl-2-(p-tolyl)oxazol-4-yl]-butyl}-1,3-dithiane-r-2-caroxylate in methanol, 1 ml of aqueous solution of 1 N sodium hydroxide was added, and heated to reflux for 1.5 hours. The reaction solution was concentrated. The residue was, after addition of water, washed with diethyl ether. The aqueous layer was acidified with 1N hydrochloric acid, extracted with ethyl acetate, dried over anhydrous magnesium sulfate and concentrated. The residue was crystallized by adding isopropyl ether, and washed with n-hexane to provide 88 mg of the objective compound as colorless crystals.

M.p. 157–159° C.

Elemental analysis for $C_{21}H_{27}NO_3S_2$

Calcd.(%): C, 62.19; H, 6.71; N, 3.45.

Found (%): C, 61.93; H, 6.70; N, 3.40.

EXAMPLE 83

2-Methyl-t-5-{4-[5-methyl-2-(p-tolyl)oxazol-4-yl]butyl}-1,3-dithiane-r-2-carboxylic Acid The objective compound was prepared by the same procedure as Example 82.

M.p. 162–164° C.

Elemental analysis for $C_{21}H_{27}NO_3S_2$

Calcd.(%): C, 62.19; H, 6.71; N, 3.45.

Found (%): C, 61.75; H, 6.66; N, 3.42.

EXAMPLE 84

2-Methyl-2-{6-[5-methyl-2-(p-tolyl)oxazol-4-yl]hexylthio}propionic acid

Under argon atmosphere, 24 mg of triturated sodium hydroxide was added to 2 ml of a solution of 100 mg of 4-(6-acetylthiohexyl)-5-methyl-2-(p-tolyl)oxazole in acetone, and stirred for 2 hours at room temperature. To the reaction solution, 20 μl of water was added, followed by addition of 113 mg of 1,1,1-trichloro-2-methyl-2-propanol·0.5 hydride (chloretone), and then 96.5 mg of triturated sodium hydroxide in tree portions at 30 minutes intervals. The mixture was stirred for additional 18 hours at room temperature. The reaction solution was concentrated. The residue was, after addition of water, extracted with diethyl ether. The organic layers were combined, washed with water, and the washings was acidified with 1 N hydrochloric acid and extracted with ethyl acetate. The organic layers were combined, washed with water and brine sequentially, dried over anhydrous magnesium sulfate, and the solvent was distilled off under reduced pressure. The residue was purified by silica gel column chromatography (Wakogel® C-200, chloroform: methanol=100:1) and the resulting crystals were washed with n-hexane to provide 28.0 mg of the objective compound as pale yellow crystals.

M.p. 111° C.

Elemental analysis for $C_{21}H_{29}NO_3S_2$

Calcd.(%): C, 67.17; H, 7.78; N, 3.73.

Found (%): C, 67.33; H, 7.85; N, 3.67.

EXAMPLE 85

2-Methyl-2-{6-[5-methyl-2-(p-tolyl)oxazol-4-yl]hexyloxy}propiononitrile

Phosphorus tribromide (6.77 g) was added to 94 ml of a solution of 4.90 g of 2-methyl-2-{6-[5-methyl-2-(p-tolyl)oxazol-4-yl]hexyloxy}propionohydroxamic acid in benzene, and heated to reflux for 4 hours. The reaction solution was cooled, poured into ice-cold water. After addition of saturated aqueous sodium hydrogencarbonate solution, the mixture was extracted with ethyl acetate. The organic layer was washed with water and brine sequentially, dried over anhydrous magnesium sulfate and concentrated. The residue was purified by silica gel column chromatography (Wakogel® C-200, n-hexane: ethyl acetate=9:1) to provide 3.32 g of the objective compound as a colorless crystals. M.p. 36° C.

Elemental analysis for $C_{21}H_{28}N_2O_2 \cdot 1/5H_2O$

Calcd.(%): C, 73.31; H, 8.32; N, 8.14.

Found (%): C, 73.21; H, 8.27; N, 7.88.

EXAMPLE 86

5-[1-Methyl-1-{6-[5-methyl-2-(p-tolyl)oxazol-4-yl]hexyloxy}ethyl]tetrazole

Sodium azide (4.12 g) and 2.97 g of ammonium chloride were added to 27 ml of a solution of 2.70 g of 2-methyl-2-{6-[5-methyl-2-(p-tolyl)oxazol-4-yl]hexyloxy}-propiononitrile in N,N-dimethylformamide, and stirred for 1.5 hours at 120° C. To the reaction solution was added ice-cold water, and extracted with ethyl acetate, washed with water and brine sequentially, dried over anhydrous magnesium sulfate and concentrated. The residue was purified by silica gel column chromatography (Wakogel® C-200, chloroform: methanol=100:1 to 50:1) and recrystallized from isopropyl ether to provide 1.69 g of the objective compound as colorless crystals. M.p. 87° C.

Elemental analysis for $C_{21}H_{29}N_5O_2$

Calcd.(%): C, 65.77; H, 7.62; N, 18.26.

Found (%): C, 65.67; H, 7.65; N, 17.97.

EXAMPLE 87

2-Methyl-c-5-{4-[5-methyl-2-(p-tolyl)oxazol-4-yl]butyl}-1,3-dioxane-r-2-carboxyamide Under argon atmosphere, 45 ml of a solution of 3.00 g of 2-methyl-c-5-{4-[5-methyl-2-(p-tolyl)oxazol-4-yl]butyl}-1,3-dioxane-r-2-carboxylic acid in tetrahydrofuran was cooled with ice and 1.12 ml of triethylamine, and then 5 ml of a solution of 959 mg of ethyl chloroformate in tetrahydrofuran were added dropwise. After 45-minute-stirring, 45 ml of ammonia-saturated tetrahydrofuran was added dropwise, and stirred for additional 1 hour. To the reaction solution was added water, and extracted with ethyl acetate, washed with saturated sodium hydrogencarbonate and water sequentially and dried over anhydrous magnesium sulfate. The solvent was distilled off under reduced pressure and the resulting crystals were washed with diethyl ether to provide 2.81 g of the objective compound as colorless crystals. M.p. 146–147° C.

Elemental analysis for $C_{21}H_{28}N_2O_4$

Calcd.(%): C, 67.72; H, 7.58; N, 7.52.

Found (%): C, 67.26; H, 7.54; N, 7.39.

EXAMPLE 88

2-Methyl-c-5-{4-[5-methyl-2-(p-tolyl)oxazol-4-yl]-butyl}-1,3-dioxane-r-2-carbonitrile Under argon atmosphere, 2.04 ml of triethylamine was added dropwise to 34 ml of a solution of 2.27 g of 2-methyl-c-5-{4-[5-methyl-2-(p-tolyl)oxazol-4-yl]butyl}-1,3-dioxane-r-2-carboxyamide in tetrahydrofuran. After 10-minute-stirring under ice-cooling, 5 ml of a solution of 1.53 g of trifluoroacetic anhydride in tetrahydrofuran was added drowse slowly, and stirred additional 1 hour. To the reaction solution was added water, and extracted with diethyl ether, washed with saturated sodium hydrogen carbonate and water sequentially, dried over anhydrous magnesium sulfate. The solvent was distilled off under reduced pressure. The residue was purified by silica gel column chromatography (Wakogel® C-200, n-hexane: ethyl acetate=4:1) to provide 2.07 g of the objective compound as colorless crystals. M.p. 79–80° C.

Elemental analysis for $C_{21}H_{26}N_2O_3$

Calcd.(%): C, 71.16; H, 7.39; N, 7.90.

Found (%): C, 71.01; H, 7.42; N, 7.90.

EXAMPLE 89

Methyl 2-methyl-c-5-14-[5-methyl-2-(p-tolyl)oxazol-4-yl]butyl}-1,3-dithine-r-2-carboxylate To 20 ml of a solution of 635 mg of 4-[5,5-bis(mercaptomethyl)pentyl]-5-methyl-2-(p-tolyl)oxazole in acetonitrile, 0.344 ml of methyl pyruvate and 0.48 ml of boron trifluoride etherate (about 47%) were added, and heated to reflux for 2 hours. The reaction solution was cooled, poured into ice-cold water and extracted with ethyl acetate. The organic layer was washed with brine, dried over anhydrous magnesium sulfate and concentrated. The residue was purified by silica gel column chromatography (Wakogel® C-200, n-hexane: ethyl acetate=9:1) and the fractions eluted earlier were concentrated to provide 124 mg of the objective compound as colorless oil.

$^1$H-NMR (CDCl$_3$) δ: 1.25–1.55 (4H, m), 1.69 (3H, s), 1.70–1.90 (3H, m), 2.31 (3H, s), 2.38 (3H, s), 2.40–2.60 (4H, m), 3.54 (2H, m), 3.77 (3H, s), 7.22 (2H, s), 7.86 (2H, s).

EXAMPLE 90

Methyl 2-methyl-t-5-{4-[5-methyl-2-(p-tolyl)oxazol-4-yl]butyl}-1,3-dithiane-r-2-carboxylate The latter fractions of Example 89 were collected and concentrated to provide 124 mg of the objective compound as colorless oil.

$^1$H-NMR (CDCl$_3$) δ: 1.30–1.50 (4H, m), 1.55–1.90 (7H, m), 2.31 (3H, s), 2.38 (3H, s), 2.47 (2H, t), 2.58 (2H, dd), 3.07 (2H, dd), 3.11 (2H, s), 7.23 (2H, d), 7.87 (2H, d).

EXAMPLE 91

2-Methyl-2-{6-[5-methyl-2-(p-tolyl)oxazol-4-yl]hexyloxy}propionohydroxamic Acid

To 20 ml of a solution of 4.84 g of ethyl 2-methyl-2-{6-[5-methyl-2-(p-tolyl)oxazol-4-yl]hexyloxy}propionate in methanol, 3.47 g of hydroxylammonium chloride was added, and then 12.5 ml of solution of 5 M potassium hydroxide in methanol was added dropwise slowly under ice-cooling with stirring. The ice-bath was removed and the mixture was stirred for 36 hours at room temperature. The reaction solution was concentrated. The residue was acidified with 50% aqueous acetic acid solution, water was added thereto and extracted with ethyl acetate. The organic layer was washed with water and brine serially, dried over anhydrous magnesium sulfate and concentrated. The residue was concentrated after addition of toluene, and again concentrated after addition of ethanol to provide 4.90 g of the objective compound as pale yellow oil.

$^1$H-NMR (CDCl$_3$) δ: 1.36–1.41 (4H, m), 1.38 (6H, s), 1.53–1.70 (4H, m), 2.31 (3H, s), 2.38 (3H, s), 2.48 (2H, t), 3.37 (2H, t), 7.23 (2H, d), 7.87 (2H, d).

EXAMPLE 92

Methyl 2-methyl-c-5-{4-[1,5-dimethyl-2-(p-tolyl)imidazol-4-yl]butyl}-1,3-dioxane-r-2-carboxylate To 20 ml of a solution of 0.80 g of methyl c-5-[5-acetyl-5-(p-toluoylamino)pentyl]-2-methyl-1,3-dioxane-r-2-carboxylate in xylene, 1.5 ml of a solution of 2 M methylamine in tetrahydrofuran and 0.84 ml of acetic acid were added. The mixture was subjected to azeotropic dehydration with Dean-Stark apparatus for 2 hours. The reaction solution was cooled, poured into aqueous sodium hydrogen carbonate, extracted with ethyl acetate, dried over anhydrous magnesium sulfate and concentrated. The residue was purified by silica gel column chromatography (Wakogel® C-200, chloroform: methanol=100:1) to provide 634 mg of the objective compound as pale yellow oil.

$^1$H-NMR (CDCl$_3$) δ: 0.97–1.10 (2H, m), 1.20–1.40 (2H, m), 1.50 (3H, s), 1.54–1.70(2H, m), 1.90–2.15 (1H, m), 2.18 (3H, s), 2.38 (3H, s), 2.51 (2H, t), 3.38 (2H, t), 3.53 (3H, s), 3.83 (3H, s), 3.95 (2H, dd), 7.23 (2H, dd), 7.45 (2H, dd).

EXAMPLE 93

Methyl 2-methyl-c-5-{4-[5-methyl-2-(p-tolyl)thiazol-4-yl]butyl}-1,3-dioxane-r-2-carboxylate To 10 ml of tetrahydrofuran, 1.01 g of methyl c-5-[5-acetyl-5-(p-toluoylamino)pentyl]-2-methyl-1,3-dioxane-r-2-carboxylate was dissolved. After addition of 1.42 g of 2,4-bis(methylthio)-1,3-dithia-2,4-diphosphetane-2,4-disulfide (Davy reagent methyl), the mixture was stirred for 3 hours at 50–55° C. and additional 3 hours at 70–75° C. To the reaction solution was added ethyl acetate, and washed with 10% hydrochloric acid, water and 10% sodium hydroxide sequentially, dried over magnesium sulfate and concentrated. The residue was purified by silica gel column chromatography (Wakogel® C-200, n-hexane: ethyl acetate= 5:1) to provide 384 mg of the objective compound as pale yellow oil.

$^1$H-NMR (CDCl$_3$) δ: 1.00–1.15 (2H, m), 1.23–1.40 (2H, m), 1.51 (3H, s), 1.60–1.77 (2H, m), 1.92–2.14 (1H, m), 2.37 (6H, s), 2.66 (2H, t), 3.39 (2H, t), 3.83 (3H, s), 3.95 (2H, dd), 7.20 (2H, d), 7.75 (2H, d).

EXPERIMENTAL EXAMPLE 1

Effects on carbohydrate and lipid metabolism in KK-A$^y$ Mouse

The experiment was conducted using the compounds described in the Examples as test compounds and Troglitazone (5-[4-(6-hydroxy-2,5,7,8-tetramethylchroman-2-ylmethoxy)benzyl]-2,4-thiazolidinedione) as a control compound.

Each test compound was orally administered to KK-A$^y$ mice (10 week old, male), NIDDM model animal, for 4 days at a given dosage. On the next day of the last administration, blood was collected from tail end blood vessels under non-fasting conditions to prepare heparinized plasma. Thereafter, blood was collected from an abdominal large vein under pentobarbital anesthesia to prepare serum. The glucose level (BG), triglyceride level (TG) and insulin level (Ins) in plasma were measured using a glucose CII-test Wako (Wako Pure Chemical Industries, Ltd), CLINTECH TG-S (IATORON LABORATORIES, INC.) or triglyceride E-test WAKO (Wako Pure Chemical Industries, Ltd), and a rat insulin measurement kit (Morinaga Biochemistry Research Institute) or REBIS-insulin-mouse-T (Mouse Insulin ELISA (TMB) KIT, Shibayagi Co., Ltd), respectively. Also, the sum of VLDL-C level and LDL-C level in serum (hereinafter, referred to as "(V)LDL-C"), total cholesterol level (TC) and HDL-C level were measured using a high performance liquid chromatography system for the measurement of lipoprotein cholesterol (TOSOH CORPORATION). (V)LDL-C level was measured because VLDL-C and LDL-C cannot be measured separately. Atherogenic Index (AI) was calculated according to the following formula:

$$AI=[(TC\ level)-(HDL\text{-}C\ level)]/(HDL\text{-}C\ level).$$

The results are shown in Table 1.

TABLE 1

Effects on carbohydrate and lipid metabolism of KK-A$^y$ mice

| Test compound | Dose (mg/kg) | Percent change of each parameter compared to control group (%) | | | | | |
|---|---|---|---|---|---|---|---|
| | | TG | BG | Ins | (V)LDL-C | HDL-C | AI |
| Example 39 | 1 | −56 | −14 | −20 | −53 | 36 | −73 |
| Example 14 | 1 | −29 | −22 | −67 | −38 | 19 | −45 |
| Example 9 | 1 | −46 | −12 | −36 | −29 | 36 | −49 |
| Example 54 | 1 | −72 | −24 | −14 | −77 | 24 | −83 |
| Example 38 | 1 | −50 | −21 | −39 | −38 | 38 | −65 |
| Example 21 | 3 | −52 | −18 | −26 | −26 | 5 | −38 |
| Example 20 | 1 | −31 | −15 | −44 | −33 | 30 | −44 |
| Example 53 | 3 | −51 | −46 | −37 | −49 | 3 | −62 |
| Example 18 | 3 | −43 | −12 | −1 | −20 | 76 | −65 |
| Example 55 | 10 | −45 | −22 | 2 | −44 | 62 | −72 |
| Example 37 | 3 | −51 | −5 | −27 | −54 | 33 | −70 |
| Example 11 | 3 | −83 | −36 | −16 | −89 | 11 | −91 |
| Example 81 | 1 | −62 | −8 | −21 | −76 | 32 | −83 |
| Example 64 | 1 | −53 | −12 | −20 | −63 | 21 | −72 |
| Example 70 | 3 | −37 | −15 | 5 | −33 | 41 | −53 |
| Example 71 | 3 | −89 | −51 | −61 | −90 | 1 | −90 |
| Example 73 | 3 | −92 | −53 | −68 | −90 | −8 | −85 |
| Example 74 | 3 | −46 | −18 | −33 | −58 | 55 | −72 |
| Example 75 | 3 | −47 | −23 | −29 | −50 | 37 | −61 |
| Troglitazone | 300 | −11 | −9 | −22 | −26 | −8 | −7 |

The present compounds showed excellent blood triglyceride lowering effect and (V)LDL-C lowering effect. Furthermore, the present compounds showed blood glucose lowering effect, blood insulin lowering effect or HDL-C increasing effect or atherogenic index lowering effect. It is clear that the present compounds are useful as a preventive or therapeutic agent for arteriosclerosis, and the like.

FORMULATION EXAMPLE 1

| Tablet (for oral administration) | |
|---|---|
| Formulation per a tablet (200 mg) | |
| Compound of Example 71 | 20 mg |
| Cornstarch | 88 mg |
| Crystalline cellulose | 80 mg |
| Carboxymethyl cellulose calcium | 10 mg |
| Light silicic acid anhydride | 1 mg |
| Magnesium stearate | 1 mg |

A mixture containing the ingredients of the ratio above is compressed to form a tablet for oral administration.

FORMULATION EXAMPLE 2

| Tablet (for oral administration) | |
|---|---|
| Formulation per a tablet (120 mg) | |
| Compound of Example 11 | 1 mg |
| Lactose | 60 mg |
| Cornstarch | 30 mg |
| Crystalline cellulose | 20 mg |
| Hydroxypropylcellulose | 7 mg |
| Magnesium stearate | 2 mg |

A mixture containing the ingredients of the ratio above is compressed to form a tablet for oral administration.

FORMULATION EXAMPLE 3

| Tablet (for oral administration) | |
|---|---|
| Formulation per a tablet (180 mg) | |
| Compound of Example 73 | 100 mg |
| Lactose | 45 mg |
| Cornstarch | 20 mg |
| Low-substituted hydroxypropylcellulose | 9 mg |
| Polyvinyl alcohol (partially saponified) | 5 mg |
| Magnesium stearate | 1 mg |

A mixture containing the ingredients of the ratio above is compressed to form a tablet for oral administration.

INDUSTRIAL APPLICABILITY

The present compounds have excellent blood triglyceride lowering effect, (V)LDL-C lowering effect, and blood glucose lowering effect, blood insulin lowering effect, or HDL-C increasing effect or atherogenic index lowering effect all together, and hence is useful in the prevention or treatment of coronary artery diseases, cerebral infarction, hyperlipidemia, arteriosclerosis, diabetes mellitus, hypertension, obesity, and the like.

What is claimed is:

1. A therapeutic pharmaceutical composition for hyperlipidemia, comprising as an active ingredient a heterocyclic compound of the formula [1], or a pharmaceutically acceptable salt thereof:

$$R^1\text{-Het-D-E} \quad [1]$$

wherein:

R$^1$ is aryl; said aryl being optionally substituted by the same or different one to three groups selected from alkyl, haloalkyl, trihaloalkyl, alkoxy, halogen and nitro;

Het is an oxazole which is optionally substituted by alkyl or trihaloalkyl;

D is alkylene, alkenylene, or alkynylene, and

E is a group of the formula [3]:

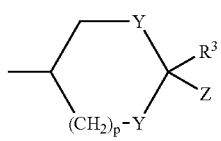

[3]

wherein Y is oxygen or sulfur; R$^3$ is hydrogen or alkyl; p is an integer of 0–2; Z is carboxy, alkoxycarbonyl, hydroxymethyl, carbamoyl, N-hydroxycarbamoyl, N-alkylcarbamoyl, N,N'-dialkylcarbamoyl, cyano, 1H-5-tetrazolyl, 1-alkyl-5-tetrazolyl, or 2-alkyl-5-tetrazolyl; and a pharmaceutically acceptable carrier.

2. The therapeutic pharmaceutical composition for hyperlipidemia of claim 1, wherein D is alkylene, alkenylene or alkynylene having 3–10 carbon atoms.

3. The therapeutic pharmaceutical composition for hyperlipidemia of claim 1, wherein Het is a divalent aromatic heterocyclic group of the formula [5]:

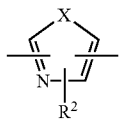

wherein X is oxygen; and R² is hydrogen, alkyl or trihaloalkyl; and D is alkylene, alkenylene or alkynylene having 3–10 carbon atoms.

4. The therapeutic pharmaceutical composition for hyperlipidemia of claim 3, wherein R¹ is phenyl optionally substituted by one to two groups selected from alkyl, halogen, trihaloalkyl and alkoxy; Het is a divalent aromatic heterocyclic group of the formula [5a]:

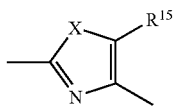

wherein X is oxygen and R¹⁵ is alkyl or trihaloalkyl; and D is alkylene or alkenylene having 3–7 carbon atoms.

5. The therapeutic pharmaceutical composition for hyperlipidemia of claim 4, wherein R¹ is phenyl optionally substituted by one to two groups selected from alkyl, halogen, trihaloalkyl and alkoxy; Het is a divalent aromatic heterocyclic group of the formula [5a]; X is oxygen R¹⁵ is alkyl or trihaloalkyl, D is alkylene or alkenylene having 3–5 carbon atoms; B is a group of the formula [3] wherein p is 1, Y is oxygen, R³ is hydrogen or alkyl, and Z is carboxy or alkoxycarbonyl.

6. The therapeutic pharmaceutical composition for hyperlipidemia of claim 4, wherein R¹ is phenyl optionally substituted by one to two groups selected from alkyl, halogen and alkoxy; Het is a divalent aromatic heterocyclic group of the formula [5a]; X is oxygen; R¹⁵ is alkyl or trihaloalkyl; D is alkylene, alkenylene or alkynylene having 5–7 carbon atoms.

7. The therapeutic pharmaceutical composition for hyperlipidemia of claim 5, wherein R¹ is phenyl optionally substituted by one to two groups selected from alkyl and alkoxy, Het is a divalent aromatic heterocyclic group of the formula [5a] wherein X is oxygen, R¹⁵ is alkyl; D is alkylene having 3–5 carbon atoms; E is a group of the formula [3] wherein p is 1, Y is oxygen, R³ is alkyl, and Z is carboxy.

8. The therapeutic pharmaceutical composition for hyperlipidemia of claim 6, wherein R¹ is phenyl optionally substituted by one to two groups selected from alkyl, halogen and alkoxy; Het is a divalent aromatic heterocyclic group of the formula [5a] wherein X is oxygen, R¹⁵ is alkyl; D is alkylene, alkenylene or alkynylene having 5–7 carbon atoms.

9. The therapeutic pharmaceutical composition for hyperlipidemia of claim 1, wherein the active ingredient is selected from the group consisting of compounds (1) to (10) below:

(1) c-5-[4-(5-Methyl-2-phenyloxazol-4-yl)butyl]-1,3-dioxane-r-2-carboxylic acid,
(2) 2-Isobutyl-c-5-[4-(5-methyl-2-phenyloxazol-4-yl)butyl]-1,3-dioxane-r-2-carboxylic acid,
(3) 2-Ethyl-c-5-[4-(5-methyl-2-phenyloxazol-4-yl)butyl]-1,3-dioxane-r-2-carboxylic acid,
(4) 2-Methyl-c-5{4-[5-methyl-2-(4-trifluoromethylphenyl)oxazol-4-yl]butyl}-1,3-dioxane-r-2-carboxylic acid,
(5) 2-Methyl-c-5-[4-(5-methyl-2-phenyloxazol-4-yl)-(E)-3-butenyl]-1,3-dioxane-r-2-carboxylic acid,
(6) c-5-{4-[2-(4-tert-Butylphenyl)-5-methyloxazol-4-yl]butyl}-2-methyl-1,3-dioxane-r-2-carboxylic acid,
(7) 2-Methyl-c-5-{4-[5-methyl-2-(p-tolyl)oxazol-4-yl]butyl}1,3-dioxane-r-2-carboxylic acid,
(8) 2-Methyl-c-5-{4-[5-methyl-2-(3-fluoro-4-methylphenyl)oxazol-4-yl]butyl}-1,3-dioxane-r-2-carboxylic acid,
(9) 2-Methyl-c-5-{4-[5-methyl-2-(m-tolyl)oxazol-4-yl]butyl}-1,3-dioxane-r-2-carboxylic acid, and
(10) 2-Methyl-c-5-{4-[5-methyl-2-(3,4-dimethylphenyl)oxazol-4-yl]butyl}-1,3-dioxane-r-2-carboxylic acid or a pharmaceutically acceptable salt thereof.

10. A heterocyclic compound of the formula [1], or a pharmaceutically acceptable salt thereof:

$$R^1\text{-HET-D-E} \qquad [1]$$

wherein:

R¹ is aryl; said aryl being optionally substituted by the same or different one to three groups selected from alkyl haloalkyl, trihaloalkyl alkoxy, halogen and nitro;

Het is an oxazole which is optionally substituted by alkyl or trihaloalkyl;

D is alkylene, alkenylene, or alkynylene: and

E is a group of the formula [3]:

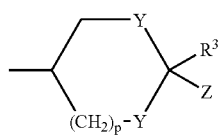

wherein Y is oxygen or sulfur; R³ is hydrogen or alkyl; p is an integer of 0–2; Z is carboxy, alkoxycarbonyl, hydroxymethyl, carbamoyl, M-hydroxycarbamoyl, N-alkylcarbamoyl, N,N-dialkylcarbamoyl, cyano, 1H-5-tetrazoyl, 1-alkyl-5-tetrazoyl, or 2-alkyl-5 tetrazolyl.

11. The heterocyclic compound of claim 10, wherein D is alkylene, alkenylene or alkynylene having 3–10 carbon atoms, or a pharmaceutically acceptable salt thereof.

12. The heterocyclic compound of claim 10, wherein Het is a divalent aromatic heterocyclic group of the formula [5]:

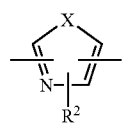

wherein X is oxygen; and R² is hydrogen, alkyl or trihaloalky; and D is alkylene, alkenylene or alkynylene having 3–10 carbon atoms; or a pharmaceutically acceptable salt thereof.

13. The heterocyclic compound of claim 12, wherein R¹ is phenyl optionally substituted by one to two groups selected from alkyl, halogen, trihaloalkyl and alkoxy; Het is a divalent aromatic heterocyclic group of the formula [5a]:

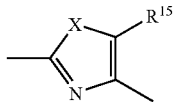

wherein X is oxygen; and $R^{15}$ is alkyl or trihaloalkyl; and D is alkylene or alkenylene having 3–7 carbon atoms, or a pharmaceutically acceptable salt thereof.

14. The heterocyclic compound of claim 13, wherein $R^1$ is phenyl optionally substituted by one to two groups selected from alkyl, halogen, trihaloalkyl and alkoxy; Het is a divalent aromatic heterocyclic group of the formula [5a] wherein X is oxygen; $R^{15}$ is alkyl or trihaloalkyl; and D is alkylene or alkenylene having 3–5 carbon atoms; E is a group of the formula [3] wherein p is 1, Y is oxygen, $R^3$ is hydrogen or alkyl, and Z is carboxy or alkoxycarbonyl; or a pharmaceutically acceptable salt thereof.

15. The heterocyclic compound of claim 13, wherein $R^1$ is phenyl optionally substituted by one to two groups selected from alkyl, halogen and alkoxy; Het is a divalent aromatic heterocyclic group of the formula [5a] wherein X is oxygen; $R^{15}$ is alkyl or trihaloalkyl; and D is alkylene, alkenylene or alkynylene having 7 carbon atoms; or a pharmaceutically acceptable salt thereof.

16. The heterocyclic compound of claim 14, wherein $R^1$ is phenyl optionally substituted by one to two groups selected front alkyl and alkoxy; Het is a divalent aromatic heterocyclic group of the formula [5a] wherein X is oxygen, is alkyl; and D is alkylene having 3–5 carbon atoms; E is a group of the formula [3] wherein p is 1, Y is oxygen, $R^3$ is alkyl, and Z is carboxy, or a pharmaceutically acceptable salt thereof.

17. The heterocyclic compound of claim 15, wherein $R^4$ is phenyl optionally substituted by one to two groups selected from alkyl, halogen and alkoxy; Het is a divalent aromatic heterocyclic group of the formula [5a] wherein X is oxygen, $R^{15}$ is alkyl; and D is alkylene, alkenylene or alkynylene having 7 carbon atoms; or a pharmaceutically acceptable salt thereof.

18. The heterocyclic compound of claim 10, which is selected front the group consisting of compounds (1) to (10) below:

(1) c-5-[4-(5-Methyl-2-phenyloxazol-4-yl)butyl]-1,3-dioxane-r-2-carboxylic acid, (2) 2-Isobutyl-c-5-[4-(5-methyl-2-phenyloxazol-4-yl) butyl]-1,3-dioxane-r-2-carboxylic acid, (3) 2-Ethyl-c-5-[4-(5-methyl-2-phenyloxazol-4-yl)butyl]-1,3-dioxane-r-2-carboxylic acid, (4) 2-Methyl-c-5{4-[5-methyl-2-(4-trifluoromethylphenyl)oxazol-4-yl]butyl}-1,3-dioxane-r-2-carboxylic acid, (5) 2-Methyl-c-5-[4-(5-methyl-2-phenyloxazol-4-yl)-(E)-3-butenyl]-1,3-dioxane-r-2-carboxylic acid, (6) c-5-{4-[2-(4-tert-Butylphenyl)-5-methyloxazol-4-yl] butyl}-2-methyl-1,3-dioxane-r-2-carboxylic acid, (7) 2-Methyl-c-5-{4-[5-methyl-2-(p-tolyl)oxazol-4-yl] butyl}1,3-dioxane-r-2-carboxylic acid, (8) 2-Methyl-c-5-{4-[5-methyl-2-(3-fluoro-4-methylphenyl)oxazol-4-yl]butyl}-1,3-dioxane-r-2-carboxylic acid, (9) 2-Methyl-c-5-{4-[5-methyl-2-(m-tolyl)oxazol-4-yl] butyl}-1,3-dioxane-r-2-carboxylic acid, and

(10) 2-Methyl-c-5-{4-[5-methyl-2-(3,4-dimethylphenyl) oxazol-4-yl]butyl}-1,3-dioxane-r-2-carboxylic acid or a pharmaceutically acceptable salt thereof.

19. A method for treating arteriosclerosis, comprising administering to a subject an effective amount of a composition comprising as an active ingredient a heterocyclic compound as set forth in claim 10, or a pharmaceutically acceptable salt thereof.

20. A method for treating ischemic heart disease, comprising administering to a subject an effective amount of a composition comprising as an active ingredient a heterocyclic compound as set forth in claim 10, a pharmaceutically acceptable salt thereof.

21. A method for treating cerebral infarction, comprising administering to a subject an effective amount of a composition comprising as an active ingredient a heterocyclic compound as set forth in claim 10, or a pharmaceutically acceptable salt thereof.

22. A method for treating reocclusion after PTCA, comprising administering to a subject an effective amount of a composition comprising as an active ingredient a hetercyclic compound as set forth in claim 10, or a pharmaceutically acceptable salt thereof.

23. A method for treating diabetes mellitus, comprising administering to a subject an effective amount of a composition comprising as an active ingredient a heterocyclic compound as set forth in claim 10, or a pharmaceutically acceptable salt thereof.

24. A method for treating obesity, comprising administering to a subject an effective amount of a composition comprising as an active ingredient a heterocyclic compound as set forth in claim 10, or a pharmaceutically acceptable salt thereof.

\* \* \* \* \*

UNITED STATES PATENT AND TRADEMARK OFFICE
CERTIFICATE OF CORRECTION

PATENT NO. : 7,144,906 B2 Page 1 of 1
APPLICATION NO. : 10/276670
DATED : December 5, 2006
INVENTOR(S) : Kuwabara et al.

It is certified that error appears in the above-identified patent and that said Letters Patent is hereby corrected as shown below:

On the Title page, item 75, left side, after the inventor Kuwabara, delete "Otsu" and insert --Otsu-shi--.

On the Title page, item 75, left side, after the inventor Aoki, delete "Mori Yama" and insert therefore --Moriyama-shi--.

On the Title page, item 56, left side, under the heading "Foreign Patent Documents", delete "WO 99/231056 6/1999" and "WO 02/580048 6/2001".

On the Title page, item 56, right side, under the heading "Other Publications", delete the citation to Self, S.R. et al, second occurrence, and the citation to Yokoyama, M. et al., second occurrence.

Column 72, line 58, delete the "N' " and insert therefore --N--.

Column 74, line 43, delete "M" and insert therefore --N--.

Column 75, line 31, before the phrase "is alkyl;" insert --$R^{15}$--.

Column 75, line 35, delete "$R^4$" and insert therefore --$R^1$--

Signed and Sealed this

Twentieth Day of February, 2007

JON W. DUDAS
*Director of the United States Patent and Trademark Office*